(12) United States Patent
Azuma

(10) Patent No.: US 12,349,974 B2
(45) Date of Patent: Jul. 8, 2025

(54) OPHTHALMIC IMAGING APPARATUS AND OPHTHALMIC IMAGE PROCESSING APPRATUS

(71) Applicant: Topcon Corporation, Tokyo (JP)

(72) Inventor: Shinnosuke Azuma, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 603 days.

(21) Appl. No.: 17/842,787

(22) Filed: Jun. 17, 2022

(65) Prior Publication Data

US 2022/0409046 A1 Dec. 29, 2022

(30) Foreign Application Priority Data

Jun. 24, 2021 (JP) .................................. 2021-104547

(51) Int. Cl.
*A61B 3/135* (2006.01)
*A61B 3/10* (2006.01)
(Continued)

(52) U.S. Cl.
CPC .............. *A61B 3/135* (2013.01); *A61B 3/102* (2013.01); *A61B 3/12* (2013.01); *G01B 9/02091* (2013.01)

(58) Field of Classification Search
CPC ........... A61B 3/135; A61B 3/102; A61B 3/12; A61B 3/113; A61B 3/0025; A61B 3/14; G01B 9/02091
(Continued)

(56) References Cited

U.S. PATENT DOCUMENTS

2014/0063460 A1* 3/2014 Borycki .................. G06T 7/337
351/208
2015/0085252 A1* 3/2015 Fujimura ............. A61B 3/0083
351/208
(Continued)

FOREIGN PATENT DOCUMENTS

JP 2013-248376 A 12/2013
JP 2016-159073 A 9/2016
(Continued)

OTHER PUBLICATIONS

Jiang et al., "Super SloMo: High Quality Estimation of Multiple Intermediate Frames for Video Interpolation", arXiv:1712.00080v2 [cs.CV], Jul. 13, 2018, 12 pages.
(Continued)

*Primary Examiner* — Mohammed A Hasan
(74) *Attorney, Agent, or Firm* — XSENSUS LLP

(57) ABSTRACT

In the ophthalmic imaging apparatus of an aspect example, the first image collecting unit collects a series of Scheimpflug images by performing scanning of a three dimensional region of a subject's eye with slit light. The second image collecting unit collects a series of time series images by performing repetitive photography of the subject's eye in parallel with the scanning of the three dimensional region performed by the first image collecting unit. The first image analyzing unit analyzes the series of time series images to determine time series shifts of the slit light during the scanning of the three dimensional region performed by the first image collecting unit. The image interpolating unit performs interpolation of the series of Scheimpflug images based on the time series shifts of the slit light determined by the first image analyzing unit.

29 Claims, 20 Drawing Sheets

(51) Int. Cl.
 *A61B 3/12* (2006.01)
 *G01B 9/02091* (2022.01)

(58) Field of Classification Search
 USPC .......................................................... 351/206
 See application file for complete search history.

(56) References Cited

U.S. PATENT DOCUMENTS

| | | | |
|---|---|---|---|
| 2016/0345822 A1 | 12/2016 | Fujimura et al. | |
| 2018/0028056 A1* | 2/2018 | Kubota | G06T 7/12 |
| 2020/0390330 A1* | 12/2020 | Fukuma | A61B 3/10 |
| 2021/0153740 A1* | 5/2021 | Oomori | A61B 3/135 |
| 2022/0280036 A1 | 9/2022 | Liu et al. | |

FOREIGN PATENT DOCUMENTS

| | | |
|---|---|---|
| JP | 2016-179004 A | 10/2016 |
| JP | 2018000685 A | 1/2018 |
| JP | 2018033693 A | 3/2018 |
| JP | 2019-213733 A | 12/2019 |
| WO | 2019240151 A1 | 12/2019 |
| WO | 2021049104 A1 | 3/2021 |

OTHER PUBLICATIONS

Japanese Office Action issued Nov. 19, 2024, in corresponding Japanese Patent Application No. JP 2021-104547, 9pp.

\* cited by examiner

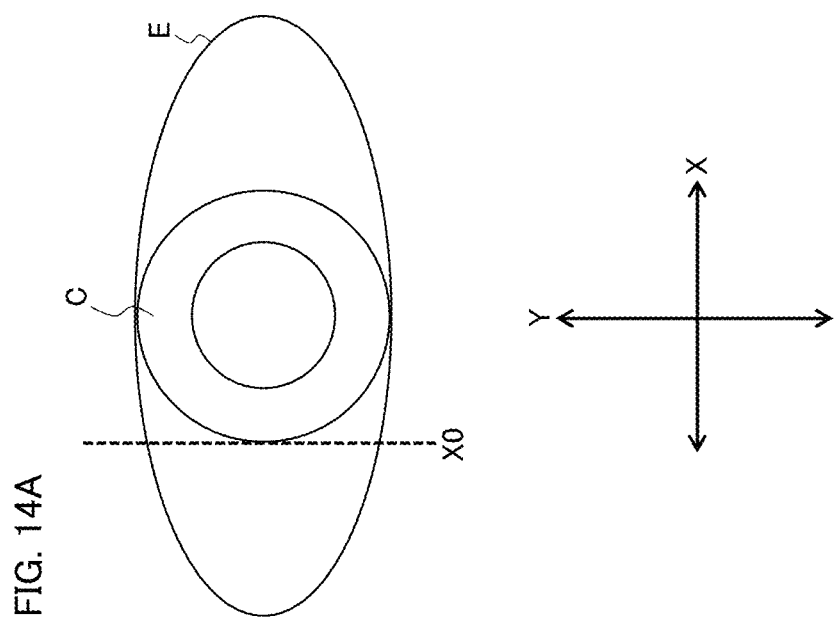

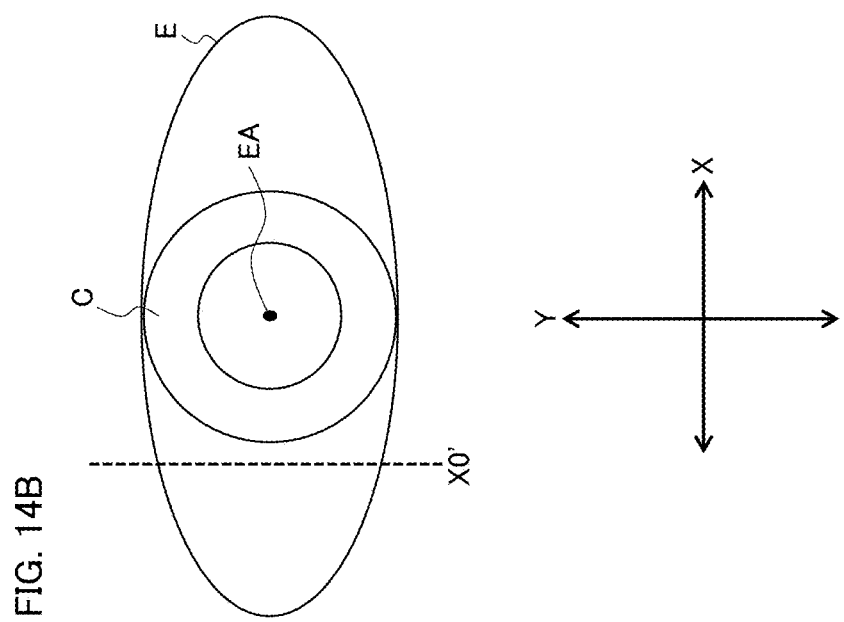

OPHTHALMIC IMAGING APPARATUS AND OPHTHALMIC IMAGE PROCESSING APPRATUS

CROSS-REFERENCE TO RELATED APPLICATION

This application is based upon and claims the benefit of priority from Japanese Patent Application No. 2021-104547, filed Jun. 24, 2021; the entire contents of which are incorporated herein by reference.

TECHNICAL FIELD

The present disclosure relates to an ophthalmic imaging apparatus and an ophthalmic image processing apparatus.

BACKGROUND OF THE INVENTION

Diagnostic imaging serves an important role in the field of ophthalmology. Diagnostic imaging uses various kinds of ophthalmic imaging apparatuses. Examples of the types of ophthalmic imaging apparatuses include a slit lamp microscope, a fundus camera, a scanning laser ophthalmoscope (SLO), an optical coherence tomography (OCT) apparatus, and the like. In addition, various kinds of ophthalmic examination apparatuses and various kinds of ophthalmic measurement apparatuses, such as a refractometer, a keratometer, a tonometer, a specular microscope, a wavefront analyzer, and a microperimeter, are generally equipped with a function of imaging anterior eye segment, eye fundus, etc.

A slit lamp microscope is one of the most widely and frequently utilized apparatuses among such various kinds of ophthalmic imaging apparatuses. A slit lamp microscope is used for illuminating a subject's eye with slit light and observing and/or photographing the illuminated cross section from an oblique or side position with a microscope (see, for example, Japanese Unexamined Patent Application Publication No. 2016-159073, Japanese Unexamined Patent Application Publication No. 2016-179004). Further, also known is a slit lamp microscope that is capable of performing scanning of a three dimensional region of a subject's eye at a relatively high speed by employing an optical system configured to satisfy the Scheimpflug condition (Scheimpflug principle) (see, for example, Japanese Unexamined Patent Application Publication No. 2019-213733 (PCT International Publication No. 2019/240149)). In addition to the slit lamp microscope, ophthalmic imaging modalities configured to perform scanning of an object with slit light include a rolling shutter camera and the like.

BRIEF SUMMARY OF THE INVENTION

An ophthalmic imaging apparatus of an example embodiment includes a first image collecting unit, a second image collecting unit, a first image analyzing unit, and an image interpolating unit. The first image collecting unit is configured to collect a series of Scheimpflug images by performing scanning of a three dimensional region of a subject's eye with slit light. The second image collecting unit is configured to collect a series of time series images by performing repetitive photography of the subject's eye in parallel with the scanning of the three dimensional region performed by the first image collecting unit. The first image analyzing unit is configured to analyze the series of time series images to determine time series shifts of (a projection position of) the slit light during the scanning of the three dimensional region. The image interpolating unit is configured to perform interpolation of the series of Scheimpflug images based on the time series shifts of (the projection position of) the slit light.

An ophthalmic imaging apparatus of an example embodiment includes a first image collecting unit, a second image collecting unit, a second image analyzing unit, and an identifier assigning unit. The first image collecting unit is configured to collect a series of Scheimpflug images by performing scanning of a three dimensional region of a subject's eye with slit light, The second image collecting unit is configured to collect a series of time series images by performing repetitive photography of the subject's eye in parallel with the scanning of the three dimensional region performed by the first image collecting unit. The second image analyzing unit is configured to analyze the series of time series images to detect a series of images of the slit light. The identifier assigning unit is configured to perform assignment of an identifier to each of the series of Scheimpflug images based on the series of images of the slit light detected from the series of time series images. Here, the identifier represents an ocular tissue onto which the slit light is being projected when a corresponding Scheimpflug image is acquired.

An ophthalmic image processing apparatus of an example embodiment includes a receiver, a first image analyzing unit, and an image interpolating unit. The receiver receives a series of images acquired by performing scanning of a three dimensional region of a subject's eye with scan light and a series of time series images collected by performing repetitive photography of the subject's eye in parallel with the scanning of the three dimensional region. The first image analyzing unit is configured to analyze the series of time series images to determine time series shifts of (a projection position of) the scan light. The image interpolating unit is configured to perform interpolation of the series of images based on the time series shifts of (the projection position of) the scan light.

An ophthalmic image processing apparatus of an example embodiment includes a receiver, a second image analyzing unit, and an identifier assigning unit. The receiver receives a series of images acquired by performing scanning of a three dimensional region of a subject's eye with scan light and a series of time series images collected by performing repetitive photography of the subject's eye in parallel with the scanning of the three dimensional region. The second image analyzing unit is configured to analyze the series of time series images to detect a series of images of the scan light. The identifier assigning unit is configured to perform assignment of an identifier to each of the series of images acquired by performing the scanning of the three dimensional region with the scan light based on the series of images of the scan light detected from the series of time series images. Here, the identifier represents an ocular tissue onto which the scan light is being projected when a corresponding image is acquired.

BRIEF DESCRIPTION OF THE SEVERAL VIEWS OF THE DRAWING

FIG. 14A is a diagram illustrating an operation executed by an ophthalmic imaging apparatus according to an aspect example.

FIG. 14B is a diagram illustrating an operation executed by an ophthalmic imaging apparatus according to an aspect example.

DETAILED DESCRIPTION OF THE INVENTION

Figure 1:
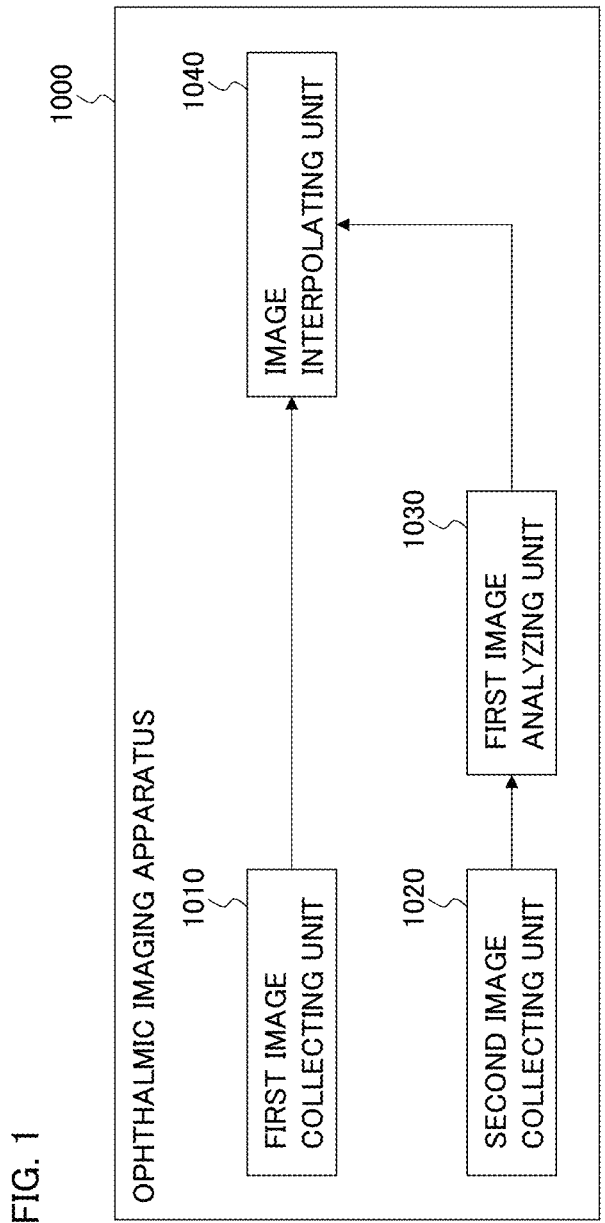
FIG. 1 is a diagram of a configuration of an ophthalmic imaging apparatus according to an aspect example.

Several aspect examples (i.e., non-limiting aspects) of embodiment examples will be described in detail with reference to the drawings. Any known technologies or techniques may be incorporated with the embodiment examples. For example, any known technologies or techniques in this technical field, such as any matters and items disclosed in the literature cited herein, may be incorporated with the embodiment examples. For example, all the content disclosed in Japanese Unexamined Patent Application Publication No. 2019-213733 (PCT International Publication No. 2019/240149) pertaining to a patent application filed by the applicant of the present application is incorporated herein by reference. The same applies to any of the contents of other documents (patent applications, papers, articles, reports, etc.) relating to the technologies or techniques that are disclosed by the applicant of the present application. It is also allowed to combine, at least in part, any two or more of the various aspects disclosed herein.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case in which the hardware is a processor, which may be considered as a certain type of circuitry, then circuitry, a unit, a means, or a term similar to these is a combination of hardware and software. In this case, the software is used to configure the hardware and/or the processor.

One non-limiting object of the embodiment examples according to the present disclosure is to improve the performance of an ophthalmic imaging apparatus configured to perform scanning of a three dimensional region of a subject's eye with slit light.

An ophthalmic imaging apparatus of the first aspect example includes a first image collecting unit, a second image collecting unit, a first image analyzing unit, and an image interpolating unit. The first image collecting unit is configured to collect a series of Scheimpflug images by performing scanning of a three dimensional region of a subject's eye with slit light. The second image collecting unit is configured to collect a series of time series images by performing repetitive photography of the subject's eye in parallel with the scanning of the three dimensional region performed by the first image collecting unit. The first image analyzing unit is configured to analyze the series of time series images to determine time series shifts of (a projection position of) the slit light during the scanning of the three dimensional region. The image interpolating unit is configured to perform interpolation of the series of Scheimpflug images on the basis of the time series shifts of (the projection position of) the slit light.

The second aspect example is the ophthalmic imaging apparatus of the first aspect, wherein the first image analyzing unit is further configured to analyze the series of time series images to detect a series of images of the slit light, and determine the time series shifts of (the projection position of) the slit light on the basis of the series of images of the slit light.

The third aspect example is the ophthalmic imaging apparatus of the first or second aspect example, wherein the scanning of the three dimensional region performed by the first image collecting unit and the repetitive photography of the subject's eye performed by the second image collecting unit are performed in synchronization with each other. In addition, the image interpolating unit is further configured to perform the interpolation of the series of Scheimpflug images based further on a correspondence between the series of Scheimpflug images and the series of time series images, the correspondence being determined on the basis of the synchronization between the scanning of the three dimensional region and the repetitive photography of the subject's eye.

The fourth aspect example is the ophthalmic imaging apparatus of any of the first to third aspect examples, wherein the first image collecting unit includes a first photography system and a second photography system that are configured to perform photography of the subject's eye from mutually different directions for the scanning of the three dimensional region. The first photography system is configured to collect a first Scheimpflug image group, and the second photography system is configured to collect a second Scheimpflug image group. In addition, the series of Scheimpflug images includes the first Scheimpflug image group and the second Scheimpflug image group.

The fifth aspect example is the ophthalmic imaging apparatus of the fourth aspect example, wherein photography performed by the first photography system and photography performed by the second photography system are performed in synchronization with each other.

The sixth aspect example is the ophthalmic imaging apparatus of the fifth aspect example that further includes an image selecting unit. The image selecting unit is configured to perform selection of another series of Scheimpflug images corresponding to the scanning of the three dimensional region from the first Scheimpflug image group and the second Scheimpflug image group on the basis of a correspondence between the first Scheimpflug image group and the second Scheimpflug image group, the correspondence being determined on the basis of the synchronization between the photography performed by the first photography system and the photography performed by the second photography system. In addition, the image interpolating unit is further configured to perform interpolation of the another series of Scheimpflug images.

The seventh aspect example is the ophthalmic imaging apparatus of the sixth aspect example, wherein the first image collecting unit further includes an illumination system configured to project the slit light onto the three dimensional region. In addition, an optical axis of the first photography system and an optical axis of the second photography system are arranged in an oblique manner in mutually opposite directions relative to an optical axis of the illumination system. Furthermore, the image selecting unit is further configured to perform the selection of the another series of Scheimpflug images by selecting a plurality of Scheimpflug images containing no corneal reflection artifact from the first Scheimpflug image group and the second Scheimpflug image group on the basis of the correspondence between the first Scheimpflug image group and the second Scheimpflug image group.

The eighth aspect example is the ophthalmic imaging apparatus of any of the first to seventh aspect examples, wherein the image interpolating unit is further configured to perform the interpolation of the series of Scheimpflug images using an optical flow that represents a shift of the subject's eye depicted in the series of Scheimpflug images as a vector.

The ninth aspect example is the ophthalmic imaging apparatus of any of the first to eighth aspect examples, wherein the image interpolating unit is further configured to perform the interpolation of the series of Scheimpflug images using an inference model constructed in advance. The inference model is constructed in advance by applying machine learning with training data including at least a Scheimpflug image of an eye to a neural network. In addition, the inference model is configured to receive an input of two or more Scheimpflug images representing two or more different locations of a same eye, and to generate an output of a spatially interpolated image of the two or more Scheimpflug images.

The tenth aspect example is the ophthalmic imaging apparatus of any of the first to ninth aspect examples, wherein the image interpolating unit includes a first interpolation quantity determining unit. The first interpolation quantity determining unit is configured to determine an interpolation quantity on the basis of one or both of operation information of the first image collecting unit and the time series shifts of (the projection position of) the slit light. In addition, the image interpolating unit is further configured to perform the interpolation of the series of Scheimpflug images with images of the interpolation quantity.

The eleventh aspect example is the ophthalmic imaging apparatus of any of the first to tenth aspect examples, wherein the first image analyzing unit is further configured to analyze the series of time series images collected by the second image collecting unit to determine time series shifts of (the projection position of) the subject's eye. In addition, the image interpolating unit further includes a second interpolation quantity determining unit. The second interpolation quantity determining unit is configured to determine an interpolation quantity on the basis of one or both of operation information of the first image collecting unit and the time series shifts of (the projection position of) the subject's eye. Furthermore, the image interpolating unit is further configured to perform the interpolation of the series of Scheimpflug images with images of the interpolation quantity.

An ophthalmic imaging apparatus of the twelfth aspect example includes a first image collecting unit, a second image collecting unit, a second image analyzing unit, and an identifier assigning unit. The first image collecting unit is configured to collect a series of Scheimpflug images by performing scanning of a three dimensional region of a subject's eye with slit light. The second image collecting unit is configured to collect a series of time series images by performing repetitive photography of the subject's eye in parallel with the scanning of the three dimensional region performed by the first image collecting unit. The second image analyzing unit is configured to analyze the series of time series images to detect a series of images of the slit light. The identifier assigning unit is configured to perform assignment of an identifier to each of the series of Scheimpflug images on the basis of the series of images of the slit light detected from the series of time series images. Here, the identifier is information that represents an ocular tissue onto which the slit light is being projected when a corresponding Scheimpflug image is acquired by the first image collecting unit.

The thirteenth aspect example is the ophthalmic imaging apparatus of the twelfth aspect example, wherein the scanning of the three dimensional region performed by the first image collecting unit and the repetitive photography of the subject's eye performed by the second image collecting unit are performed in synchronization with each other. In addition, the identifier assigning unit is further configured to perform the assignment of the identifier based further on a correspondence between the series of Scheimpflug images and the series of time series images. Here, the correspondence is determined on the basis of the synchronization between the scanning of the three dimensional region and the repetitive photography of the subject's eye.

The fourteenth aspect example is the ophthalmic imaging apparatus of the thirteenth aspect example, wherein the identifier assigning unit is further configured to perform assignment of a series of identifiers to the series of time series images on the basis of the series of images of the slit light. In addition, the identifier assigning unit is further configured to perform the assignment of the identifier to each of the series of Scheimpflug images on the basis of the series of identifiers assigned to the series of time series images and the correspondence.

The fifteenth aspect example is the ophthalmic imaging apparatus of any of the twelfth to fourteenth aspect examples, wherein the second image analyzing unit is further configured to analyze the series of Scheimpflug images to detect a series of images of the slit light. In addition, the identifier assigning unit is further configured to perform the assignment of the identifier on the basis of the series of images of the slit light detected from the series of Scheimpflug images.

The sixteenth aspect example is the ophthalmic imaging apparatus of any of the twelfth to fifteenth aspect examples, wherein the second image analyzing unit is further configured to analyze the series of Scheimpflug images to perform detection of an image of a site of interest of the subject's eye. In addition, the identifier assigning unit is further configured to perform assignment of an identifier representing the site of interest to one or more of the series of time series images collected by the second image collecting unit on the basis of a result of the detection of the image of the site of interest from the series of Scheimpflug images.

The seventeenth aspect example is the ophthalmic imaging apparatus of any of the twelfth to sixteenth aspect examples, wherein the identifier assigning unit is further configured to perform the assignment of the identifier in such a manner as to assign the identifier to a partial region of a Scheimpflug image corresponding to the ocular tissue.

The eighteenth aspect example is the ophthalmic imaging apparatus of any of the twelfth to seventeenth aspect examples, wherein the first image collecting unit includes a first photography system and a second photography system. The first photography system and the second photography system are configured to perform photography of the subject's eye from mutually different directions for the scanning of the three dimensional region. In addition, the first photography system is configured to collect a first Scheimpflug image group, and the second photography system is configured to collect a second Scheimpflug image group. Furthermore, the series of Scheimpflug images includes the first Scheimpflug image group and the second Scheimpflug image group.

The nineteenth aspect example is the ophthalmic imaging apparatus of the eighteenth aspect example, wherein photography performed by the first photography system and photography performed by the second photography system are performed in synchronization with each other.

The twentieth aspect example is the ophthalmic imaging apparatus of the nineteenth aspect example that further includes an image selecting unit. The image selecting unit is configured to perform selection of another series of Scheimpflug images corresponding to the scanning of the three dimensional region from the first Scheimpflug image group and the second Scheimpflug image group on the basis of a correspondence between the first Scheimpflug image group and the second Scheimpflug image group. Here, the correspondence is determined on the basis of the synchronization between the photography performed by the first photography system and the photography performed by the second photography system. In addition, the image assigning unit is further configured to perform assignment of the identifier to each of the another series of Scheimpflug images.

The twenty-first aspect example is the ophthalmic imaging apparatus of the twentieth aspect example, wherein the first image collecting unit further includes an illumination system. The illumination system is configured to project the slit light onto the three dimensional region. In addition, an optical axis of the first photography system and an optical axis of the second photography system are arranged in an oblique manner in mutually opposite directions relative to an optical axis of the illumination system. Furthermore, the image selecting unit is further configured to perform the selection of the another series of Scheimpflug images by selecting a plurality of Scheimpflug images containing no corneal reflection artifact from the first Scheimpflug image group and the second Scheimpflug image group on the basis of the correspondence between the first Scheimpflug image group and the second Scheimpflug image group.

The twenty-second aspect example is the ophthalmic imaging apparatus of any of the first to twenty-first aspect examples, wherein the first image collecting unit performs the scanning of the three dimensional region by performing translation of the slit light in a direction perpendicular to a longitudinal direction of the slit light.

The twenty-third aspect example is the ophthalmic imaging apparatus of the twenty-second aspect example, wherein the longitudinal direction of the slit light is oriented to coincide with a body axis direction of a subject.

The twenty-fourth aspect example is the ophthalmic imaging apparatus of the twenty-third aspect example, wherein a size of the slit light in the longitudinal direction is equal to or greater than a corneal diameter in the body axis direction. In addition, a distance of the translation of the slit light performed by the first image collecting unit is equal to or greater than a corneal diameter in a direction perpendicular to the body axis direction.

An ophthalmic image processing apparatus of the twenty-fifth aspect example includes a receiver, a first image analyzing unit, and an image interpolating unit. The receiver receives a series of images and a series of time series images. The series of images is acquired by performing scanning of a three dimensional region of a subject's eye with scan light, and the series of time series images is collected by performing repetitive photography of the subject's eye in parallel with the scanning of the three dimensional region. The first image analyzing unit is configured to analyze the series of time series images to determine time series shifts of (a projection position of) the scan light. The image interpolating unit is configured to perform interpolation of the series of images on the basis of the time series shifts of (the projection position of) the scan light.

An ophthalmic image processing apparatus of the twenty-sixth aspect example includes a receiver, a second image analyzing unit, and an identifier assigning unit. The receiver receives a series of images and a series of time series images. The series of images is acquired by performing scanning of a three dimensional region of a subject's eye with scan light, and a series of time series images is collected by performing repetitive photography of the subject's eye in parallel with the scanning of the three dimensional region. The second image analyzing unit is configured to analyze the series of time series images to detect a series of images of the scan light. The identifier assigning unit is configured to perform assignment of an identifier to each of the series of images acquired by performing the scanning of the three dimensional region with the scan light on the basis of the series of images of the scan light detected from the series of time series images. Here, the identifier is information that represents an ocular tissue onto which the scan light is being projected when a corresponding image is acquired.

These aspect examples allow the performance of an ophthalmic imaging apparatus configured to perform scanning of a three dimensional region of a subject's eye with slit light to be improved. It should be noted that aspect examples of embodiment examples pertaining to the present disclosure are not limited to the aspect examples described above.

Any matters and items that can be incorporated with the ophthalmic imaging apparatus of the first or twelfth aspect example, such as the matters and items according to one or more of the second to eleventh and the thirteenth to twenty-fourth aspect examples, may be at least in part incorporated with the ophthalmic image processing apparatus of the twenty-fifth or twenty-sixth aspect example. Furthermore, any of the matters and items described and/or suggested in the present disclosure and any matters and items equivalent thereto may be at least in part incorporated with one or more of the first to twenty-sixth aspect examples. In addition, any matters and items described and/or suggested in any disclosure (e.g., any patent application, any paper, any article, any report, etc.) made by the applicant of the present application and any matters and items equivalent thereto may be at least in part incorporated with one or more of the first to twenty-sixth aspect examples.

Outline of Several Embodiment Examples

The embodiment examples disclosed herein relate to a technique or technology of processing a series of images collected by scanning a three dimensional region of a subject's eye with slit light. Several aspect examples of the embodiment examples relate to a technique or technology of spatially interpolating a series of images collected by scanning the three dimensional region of the subject's eye with slit light, that is, relate to a spatial image interpolation technique or technology. Several other aspect examples relate to a technique or technology of assigning an identifier representing an ocular tissue to a series of images collected by scanning the three dimensional region of the subject's eye with slit light, that is, relate to an ocular tissue identifier assignment technique or technology. Yet several other aspect examples relate to both the spatial image interpolation technique or technology and the ocular tissue identifier assignment technique or technology. Scanning using slit light is sometimes referred to as slit scanning in the present disclosure.

The embodiment examples in the present disclosure mainly describe aspect examples in which slit scanning is applied to the anterior segment of the subject's eye. However, the sites or tissues to which slit scanning is applied are not limited to anterior segments or part thereof. Note that examples of the part of anterior segments include: ocular tissues such as the cornea, the iris, the anterior chamber, the corner angle, the ciliary body, the zonule of Zinn, the crystalline lens, a nerve, and a blood vessel; lesions; treatment scars; and artificial objects such as an intraocular lens and a minimally invasive glaucoma surgery device (MIGS device). In some aspect examples, slit scanning may be applied to a posterior eye segment of part thereof. Examples of the part of posterior eye segments include: ocular tissues such as the vitreous body, the retina, the choroid, the sclera, the optic nerve head, the lamina cribrosa, the macula, a nerve, a blood vessel; lesions; treatment scars; and artificial objects such as an artificial retina. Further, in some aspect examples, slit scanning may be applied to a tissue located in the vicinity of or close to the eyeball of the subject's eye such as the eyelids, the meibomian glands, etc. Furthermore, in some aspect examples, slit scanning may be applied to a three dimensional region of the subject that includes any two or all of the followings: at least part of the anterior segment of the subject's eye; at least part of the posterior segment of the subject's eye; and at least part of the tissue located in the vicinity of or close to the eyeball of the subject's.

Spatial Image Interpolation

This section describes the background, motivation, and overview of the embodiment examples regarding spatial image interpolation. In typical conventional techniques or technologies of anterior segment slit scanning, scanning is applied to a three dimensional region that includes the cornea which is a region between the sclera on the temporal side and the sclera on the nasal side. The number of frames collected by a Scheimpflug camera through such slit scanning is about several hundred, and the vertical dimension (vertical size, vertical length) of each frame (each Scheimpflug image) is about 1,000 to 3,000 pixels.

In the case of constructing a three dimensional image (volume image) from such collected images (collected frames), it is necessary to make intervals between adjacent frames small (that is, it is necessary to decrease the density of the arrangement of the collected frames) in order to provide a three dimensional image constructing processor with a group of images arranged at sufficiently small intervals. Therefore, an aspect ratio of the resulting three dimensional image becomes significantly different from an aspect ratio of the actual anterior segment. Here, an aspect ratio is a ratio between the size in the x direction and the size in the y direction, as will be described later. The significantly large difference between the aspect ratio of the resulting three dimensional image and the aspect ratio of the actual anterior segment, brings about a problem, for instance, making it difficult to carry out tasks such as medical observation and medical diagnosis, and making it difficult to perform data processing such as data analysis.

The inventors of the present disclosure have focused on these problems and developed the spatial image interpolation techniques or technologies according to several embodiment examples described herein in order to solve the non-limiting problems. In some embodiment examples, a computer-generated frame is inserted between an adjacent pair of frames by applying spatial image interpolation to the collected frames in order to perform three dimensional image construction without narrowing the intervals between the collected frames. This makes it possible to acquire a series of images (a series of frames) arranged at sufficiently narrow intervals and to construct a three dimensional image without narrowing the intervals between the collected frames. Consequently, these embodiment examples described herein allow a three dimensional image with an aspect ratio corresponding to the actual morphology (e.g., shape, form) of the anterior eye segment to be obtained.

The same applies to a rendered image obtained from a three dimensional image constructed in this way. For example, in the case in which rendering is performed in order to construct a front image (an enface image, an image defined in the XY coordinate system) from a three dimensional image with an aspect ratio corresponding to the actual morphology of the anterior segment, the resulting front image also has an aspect ratio corresponding to the actual morphology of the anterior segment. In addition, the same applies to the case in which a rendered image of another type is constructed such as a corner angle image (cross sectional image of a slow-axis scan).

Providing an image having an aspect ratio corresponding to the actual morphology of the anterior segment not only allows tasks such as medical observation and medical diagnosis and data processing such as data analysis to be carried out in an easier manner than before, but also allows the quality (e.g., accuracy, precision, reliability, reproducibility, etc.) of these tasks and this data processing to be improved. Accordingly, it becomes possible to improve the performance of slit scanning of a three dimensional region of the subject's eye.

In some embodiment examples, the number of frames (the quantity of frames) interpolated between individual pairs of adjacent frames may or may not be constant. For example, in the case in which the first frame and the second frame are adjacent to each other and the third frame and the fourth frame are adjacent to each other, the number of frames interpolated between the first frame and the second frame, and the number of frames interpolated between the third frame and the fourth frame may be equal to or different from each other.

In some aspect examples, the number of frames interpolated between adjacent frames can be determined. Determination of the number of frames interpolated may be carried out by referring to any information that affects the intervals of adjacent frames (i.e., the distances between adjacent frames), such as the distance by which slit light is moved during slit scanning, the eye movement of the subject's eye, and the photographing intervals (e.g., frame rate, frame acquisition rate) of a Scheimpflug camera. This makes it possible to perform correction of deviations in the intervals of adjacent frames caused by eye movements and correction of unevenness (ununiformity, variance) in the intervals of adjacent frames caused by scanning with non-constant speed.

The method and technique of spatial image interpolation may be freely selected. Some aspect examples may employ a method of deforming (stretching) an original image by using the resize function of open source computer vision library (OpenCV) or similar software. Here, the original image is, for example, an original three dimensional image constructed only from collected frames, or a rendered image of this original three dimensional image. However, this method is not suitable for representation of a tissue whose boundary (contour) is clear such as the cornea with clear corneal ring and whose positional change between frames is large. According to a test actually carried out by the inventors of the present disclosure, it was verified that the boundary of the cornea became discontinuous in an image generated by interpolation of this conventional method.

One known method of frame interpolation for a moving image is optical flow (optic flow), which obtains a vector representation of the movement of an object by analyzing the movement (motion) of a feature point(s) between frames. Examples of methods of optical flow include phase correlation, block-based methods, differential methods, and discrete optimization methods. Examples of the differential methods include Lucas-Kanade method, Horn-Schunck method, Buxton-Buxton method, Black-Jepson method, and general variational methods.

In addition, one known method of a newer optical flow uses a convolutional neural network (CNN). This method is disclosed, for example, in the following document: Huaizu Jiang et al., "Super SloMo: High Quality Estimation of Multiple Intermediate Frames for Video Interpolation", Proceedings of the IEEE Conference on Computer Vision and Pattern Recognition (CVPR), 2018, pp. 9000-9008 (arXiv: 1712.00080).

The inventors of the present disclosure conducted a test comparison between a frame interpolation method based on simple linear interpolation and a frame interpolation method with a CNN (a comparison of front images), and found that the latter method represents a corneal boundary more smoothly. In some aspect examples, spatial image interpolation may be performed using a freely selected optical flow technique. Further, in some aspect examples, spatial image interpolation may be performed using any neural network to which a freely selected training (a freely selected machine learning) has been applied. Furthermore, in some aspect examples, spatial image interpolation may be performed using a freely selected optical flow technique on the basis of a CNN to which a freely selected training (a freely selected machine learning) has been applied. For example, in some aspect examples, the frame interpolation method described in the above-mentioned document by Huaizu Jiang et al. may be applied to spatial image interpolation. Here, it should be noted that there are some differences between the frame interpolation method described in the above-mentioned document by Huaizu Jiang et al. and an aspect example to which this method is applied. More specifically, they are different from one another at least in that, while the former performs interpolation of a group of frames temporally arranged (i.e., a group of frames arranged in a time axis or in a chronological order, a group of frames constituting a moving image), the latter performs interpolation of a series of images spatially arranged (i.e., a series of frames arranged in a space or in a spatial coordinate system).

The matters and items described in the present section are only a part of spatial image interpolation according to the embodiment examples disclosed herein. Various kinds of matters and items of the spatial image interpolation according to the embodiment examples will be described and technically specified in the aspect examples described below. Any image processing technique or technology such as image analysis and image interpolation may be combined with or incorporated in the spatial image interpolation according to the embodiment examples. Further, any image acquisition technique or technology, any imaging (photographing) technique or technology, any image processing technique or technology (e.g., pre-processing such as image correction), or the like may be applied to an image that is subject to the spatial image interpolation according to the embodiment examples.

Ocular Tissue Identifier Assignment

This section describes the background, motivation, and overview of the embodiment examples regarding ocular tissue identifier assignment. A series of images collected from a three dimensional region of an anterior segment by slit scanning and/or processed images of this series of images (e.g., a three dimensional image, a rendered image) are/is provided for tasks such as medical observation and medical diagnosis, and/or data processing such as data analysis. In these applications, the capability of recognizing the type or the kind of an ocular tissue depicted in each image important. However, since each image acquired by slit scanning represents a cross section of an anterior segment, there may be cases in which it is difficult to identify (determine, judge, recognize, specify) an ocular tissue a cross section of which is depicted in an image on the basis of this image itself (on the basis of this image alone).

Likewise, there may be cases in which it is difficult to identify from each image a feature site of the subject's eye such as the corneal apex, or there may be cases in which it is difficult to find from each image a feature location of an imaging protocol in use such as a turnaround point (turning point, turning back point) in a round-trip scan (reciprocating scan).

The inventors of the present disclosure focused on these problems and developed the ocular tissue identifier assigning techniques or technologies according to several embodiment examples in order to solve the non-limiting problem. In some embodiment examples, collection of a series of time series images is performed in parallel with collection of a series of images performed by slit scanning, and an ocular tissue depicted in each image obtained by the slit scanning is determined by analyzing a corresponding time series image. This makes it possible to perform the assignment of an identifier to each image acquired by the slit scanning. Here, the identifier includes information that represents an ocular tissue to which slit light is being projected at the time of acquisition of that image. Such an identifier is referred to as an ocular tissue identifier. With this identifier assignment, it becomes possible to (for example, easily and/or correctly) recognize the type or the kind of an ocular tissue depicted in an image that is used for conducting tasks such as medical observation and medical diagnosis, and/or for executing data processing such as data analysis.

The number of ocular tissue identifiers assigned to one image may be freely determined, and may be one, or two or more, for example. If none of the ocular tissues contained in an ocular tissue set determined in advance are detected from an image, then no information may be assigned to that image. As an alternative, information representing that none of the ocular tissues contained in the ocular tissue set have been depicted, may be assigned to that image.

In some aspect examples, an ocular tissue identifier may be assigned to an image acquired by slit scanning, by analyzing this image. Further, in some aspect examples, an ocular tissue identifier may be assigned to a time series image corresponding to an image acquired by slit scanning, by analyzing this image acquired by the slit scanning. These aspect examples are considered to be useful in the case in which an ocular tissue (ocular site) that can only be detected from an image acquired by slit scanning is dealt with, or in the case in which an ocular tissue can be detected more suitably or favorably (e.g., detected with a higher degree of accuracy, detected with a higher degree of precision) from an image acquired by slit scanning. For example, these aspect examples may be useful in the case in which an identifier for the corneal apex is assigned, in the case in which an identifier for a tissue inside an eyeball is assigned, or the like.

The matters and items described in the present section are merely a part of ocular tissue identifier assignment according to the embodiment examples disclosed herein. Various kinds of matters and items of the ocular tissue identifier assignment according to the embodiment examples will be described and technically specified in the aspect examples described below. It is possible to incorporate any image processing techniques such as image analysis and segmentation with the ocular tissue identifier assignment according to the embodiment examples. Further, any image acquisition technique or technology, any imaging (photographing) technique or technology, any image processing technique or technology (e.g., pre-processing such as image correction) or the like may be applied to an image that is subject to the ocular tissue identifier assignment according to the embodiment examples.

Non-Limiting First Aspect Example

The first aspect example provides an aspect example of an ophthalmic imaging apparatus configured to be capable of performing spatial image interpolation. Several specific examples (several non-specific embodiment examples) of an ophthalmic imaging apparatus according to the present aspect example will be described later.

FIG. 1 shows the configuration of an ophthalmic imaging apparatus according to the present aspect example. The ophthalmic imaging apparatus 1000 includes the first image collecting unit 1010, the second image collecting unit 1020, the first image analyzing unit 1030, and the image interpolating unit 1040.

A plurality of Scheimpflug images obtained through spatial image interpolation performed by the image interpolating unit 1040 is used in various kinds of post-processing such as three dimensional image construction, rendered image construction, image analysis, and diagnostic imaging (image diagnosis). Here, the plurality of Scheimpflug images obtained through the spatial image interpolation performed by the image interpolating unit 1040 includes a series of Scheimpflug images collected by the first image collecting unit 1010 and a Scheimpflug image group interpolated into the series of Scheimpflug images by the image interpolating unit 1040. Elements for performing the post-processing such as one or more processors, one or more user interface, and the like, may be provided in the ophthalmic imaging apparatus 1000 or may be provided in an apparatus or a device different from the ophthalmic imaging apparatus 1000.

The first image collecting unit 1010 is configured to collect a series of Scheimpflug images by performing scanning of a three dimensional region of a subject's eye with slit light. More specifically, the first image collecting unit 1010 is configured to collect the series of Scheimpflug images by performing repetitive photography while moving the projection position of the slit light relative to the three dimensional region of the subject's eye. The first image collecting unit 1010 includes an optical system configured to satisfy the condition described by the Scheimpflug principle (Scheimpflug condition). The first image collecting unit 1010 functions as a Scheimpflug camera.

In some aspect examples, the first image collecting unit 1010 may be configured to perform scanning of the three dimensional region of the subject's eye by translating the slit light in a direction perpendicular to the longitudinal direction of the slit light. This scanning mode is different from that is executed by a conventional and existing anterior segment imaging apparatus that performs scanning of an anterior segment by rotating slit light.

Here, the longitudinal direction of the slit light may be defined to be the longitudinal direction of the cross section of the light beam used as the slit light at the projected position on the subject's eye. In other words, the longitudinal direction of the slit light may be defined to be the longitudinal direction of a projection image of the slit light formed on the subject's eye. The longitudinal direction of the slit light may substantially coincide with the body axis direction of the subject which is a direction along the body axis of the subject. Further, the size (length, dimension) of the slit light in the longitudinal direction may be equal to or greater than a corneal diameter in the body axis direction of the subject. In addition, the distance of the translation (distance of the movement) of the slit light may be equal to or greater than a corneal diameter in the direction perpendicular to the body axis direction of the subject.

The series of Scheimpflug images collected by the first image collecting unit 1010 is a group of images (frame group) collected continuously in terms of time. This group of images are collected respectively from a plurality of different positions in the three dimensional region of the subject's eye. Therefore, the series of Scheimpflug images collected by the first image collecting unit 1010 is different from a general moving image consisting of images temporally distributed (images temporally arranged, images temporally disposed, images arranged in a chronological order), but is a group of images spatially distributed (a group of images spatially arranged, a group of images spatially disposed, a group of images arranged in a positional order).

The optical system of the first image collecting unit 1010 includes an illumination system and a photography system. The illumination system is configured to project slit light onto a three dimensional region of the subject's eye, and the photography system is configured to perform photography of the three dimensional region of the subject's eye onto which the slit light from the illumination system is being projected. The photography system includes an image sensor. The illumination system and the photography system are configured to satisfy the Scheimpflug condition. More specifically, the illumination system and the photography system are configured in such a manner that the plane passing through the optical axis of the illumination system (the plane contains the subject plane), the principal plane of the photography system, and the light detecting plane of the image sensor all intersect on the same straight line. As a result of this, the photography system is in focus at all positions in the subject plane. In other words, the photography system is in focus at all positions in the direction along the optical axis of the illumination system.

The photography system of the first image collecting unit 1010 may include at least two photography systems. The photography system of the first image collecting unit 1010 according to some aspect examples includes the first photography system and the second photography system. The first photography system and the second photography system are configured to perform photography of the three dimensional region of the subject's eye in the slit scanning from mutually different directions. For example, consider a case in which the first image collecting unit 1010 is configured in such a manner that the longitudinal direction of the cross section of the light beam used as the slit light at the position of incidence on the subject's eye is the vertical direction (the up and down directions, the Y direction) and that the moving direction of the slit light is the horizontal direction (the left and right directions, the X direction). In this case, the first photography system and the second photography system may be disposed (arranged, configured) in such a manner that one of the first photography system and the second photography system performs photography of the subject's eye from a left oblique direction and the other performs photography of the subject's eye from a right oblique direction. A series of Scheimpflug images collected by the first photography system is referred to as the first Scheimpflug image group, and a series of Scheimpflug images collected by the second photography system is referred to as the second Scheimpflug image group. A series of Scheimpflug images collected by the first image collecting unit 1010 configured in this way includes the first Scheimpflug image group and the second Scheimpflug image group.

The second image collecting unit 1020 is configured to collect a series of time series images by performing repetitive photography of the subject's eye in parallel with the scanning of the three dimensional region of the subject's eye performed by the first image collecting unit 1010. Consequently, a series of Scheimpflug images and a series of time series images are collected during the same period of time by the first image collecting unit 1010 and the second image collecting unit 1020, respectively. A series of time series images collected by the second image collecting unit 1020 is a plurality of images arranged in a chronological order. Each of the time series images is a single image. In some examples, the second image collecting unit 1020 performs moving image photography of the three dimensional region of the subject's eye, a series of time series images is a moving image (a set of a plurality of frames arranged in a chronological order), and each of the time series images is a single frame.

In some aspect examples, slit scanning of a three dimensional region of the subject's eye performed by the first image collecting unit 1010 and repetitive photography of the subject's eye performed by the second image collecting unit 1020 may be performed in synchronization with each other. This yields a correspondence between a series of Scheimpflug images collected by the first image collecting unit 1010 and a series of time series images collected by the second image collecting unit 1020. This correspondence is a correspondence between the series of Scheimpflug images that are spatially arranged and the series of time series images that are temporally (chronologically) arranged, and defines a plurality of pairs of a Scheimpflug image and a time series image acquired substantially simultaneously (acquired at substantially the same time point). The synchronization between the first image collecting unit 1010 and the second image collecting unit 1020 may be implemented by means of a freely selected known synchronization technique. In some examples, the synchronization may be implemented by sending a synchronization signal to the first image collecting unit 1010 and the second image collecting unit 1020 from a control processor that operates based on a synchronization control program.

In some other aspect examples, post-processing may be executed to determine a correspondence between a series of Scheimpflug images collected by the first image collecting unit 1010 and a series of time series images collected by the second image collecting unit 1020. For example, a correspondence between a series of Scheimpflug images and a series of time series images may be created by comparing predetermined processing timings of Scheimpflug images sequentially acquired by the first image collecting unit 1010 and predetermined processing timings of time series images sequentially acquired by the second image collecting unit 1020 with each other.

In some examples, the predetermined processing timings for determining a correspondence between a series of Scheimpflug images and a series of time series images may be a series of combinations of the followings: a timing at which a Scheimpflug image is input from the first image collecting unit 1010 to a control processor (not shown in the drawings); and a timing at which a time series image is input from the second image collecting unit 1020 to the control processor. In other words, the predetermined processing timing for determining a correspondence between a series of Scheimpflug images and a series of time series images may be a series of combinations of the followings: a timing at which the control processor receives a Scheimpflug image; and a timing at which the control processor receives a time series image. In some other examples, the predetermined processing timings may be a series of combinations of the followings: a timing at which the control processor transfers a Scheimpflug image to a storage device (not shown in the drawings); and a timing at which the control processor transfers a time series image to the storage device. In yet some other examples, the predetermined processing timings may be a series of combinations of the followings: a timing at which a Scheimpflug image acquired by the first image collecting unit 1010 is stored in a buffer memory (not shown in the drawings); and a timing at which a time series image acquired by the second image collecting unit 1020 is stored in the buffer memory. In further some other examples, the predetermined processing timings may be a series of combinations of the followings: a timing at which a Scheimpflug image is read out from the buffer memory; and a timing at which a time series image is read out from the buffer memory.

The second image collecting unit 1020 according to some aspect examples may be configured to perform photography of the subject's eye from a position on the front side relative to the subject's eye, that is, from either a position located in the front direction relative to the subject's eye or a position located in an oblique direction relative to the front direction. In some aspect examples, in the case where the illumination system of the first image collecting unit 1010 is arranged in such a manner as to project illumination light to the subject's eye from the front direction relative to the subject's eye, then an optical system and/or an image sensor of the second image collecting unit 1020 may be disposed in an optical path branching off from the optical path of the illumination system. For example, the optical system of the second image collecting unit 1020 in the present example may be arranged coaxially with the illumination system of the first image collecting unit 1010. The second image collecting unit 1020 of the present example can acquire a front image of the subject's eye as a time series image.

In some aspect examples in which the second image collecting unit 1020 is configured to perform photography of the subject's eye from an oblique direction, the photography system of the first image collecting unit 1010 may be configured to project illumination light from an oblique direction relative to the subject's eye, and an optical system and/or an image sensor of the second image collecting unit 1020 may be disposed in an optical path branching off from the optical path of the photography system of the first image collecting unit 1010. For example, the optical system of the second image collecting unit 1020 of the present example may be arranged coaxially with the photography system of the first image collecting unit 1010. In some other aspect examples, the orientation of the optical axis of the second image collecting unit 1020 may differ from not only the orientation of the optical axis of the illumination system of the first image collecting unit 1010 but also the orientation of the optical axis of the photography system.

The second image collecting unit 1020 according to some aspect examples may be configured to perform photography of the subject's eye from two or more different directions. Specific examples of such a configuration and technique are disclosed by Japanese Unexamined Patent Application Publication No. 2013-248376 of the applicant of the present disclosure. The second image collecting unit 1020 of the present example includes two anterior segment cameras arranged in mutually different directions relative to the subject's eye. Each of the anterior segment cameras is, for example, a video camera. The two anterior segment cameras acquire two moving images, respectively, of the anterior segment of the subject's eye from mutually different directions.

The ophthalmic imaging apparatus 1000 (e.g., the first image analyzing unit 1030 thereof) may be configured to select (to perform pairing of) two frames (two photographed images) acquired substantially simultaneously (acquired at substantially the same time point), from two moving images acquired by the two anterior segment cameras respectively. In addition, the ophthalmic imaging apparatus 1000 may further be configured to analyze the two selected frames (the paired frames) to determine a three dimensional position of the subject's eye. The three dimensional position of the subject's eye may be a three dimensional position of a specific site of the anterior segment. Here, the specific site of the anterior segment may be the pupil. More specifically, the specific site of the anterior segment may be the center of the pupil, the center of gravity of the pupil, the contour of the pupil, or the like.

The first image analyzing unit 1030 is configured to analyze a series of time series images collected by the second image collecting unit 1020, thereby determining time series shifts of (a projection position of) the slit light during the scanning of the three dimensional region of the subject's eye performed by the first image collecting unit 1010. The time series shift of the slit light is a time series change in the projection position of the slit light on the subject's eye. In other words, the time series shift of the slit light represents (indicates) a movement state of the projection position of the slit light relative to the subject's eye. The first image analyzing unit 1030 includes the first image analyzing processor that operates on the basis of the first image analysis program.

In some aspect examples, the first image analyzing unit 1030 may be configured to perform the following processes: a process of analyzing the series of time series images collected by the second image collecting unit 1020 to detect a series of images of the slit light; and a process of determining time series shifts of the slit light based on the series of images of the slit light detected.

The processing of detecting a series of images of the slit light may include a process of analyzing each time series image in the series of time series images to detect an image of the slit light (a slit light image) depicted in this time series image. The detection of a slit light image from a time series image corresponds to determination of a projection position of a slit light in this time series image. By performing this slit light image detection process (i.e., slit light position determination process) on (part or all of) a series of time series images (on one or more time series images), time series shifts of the slit light during the period of time in which the series of time series images are collected, can be obtained.

Figure 2:
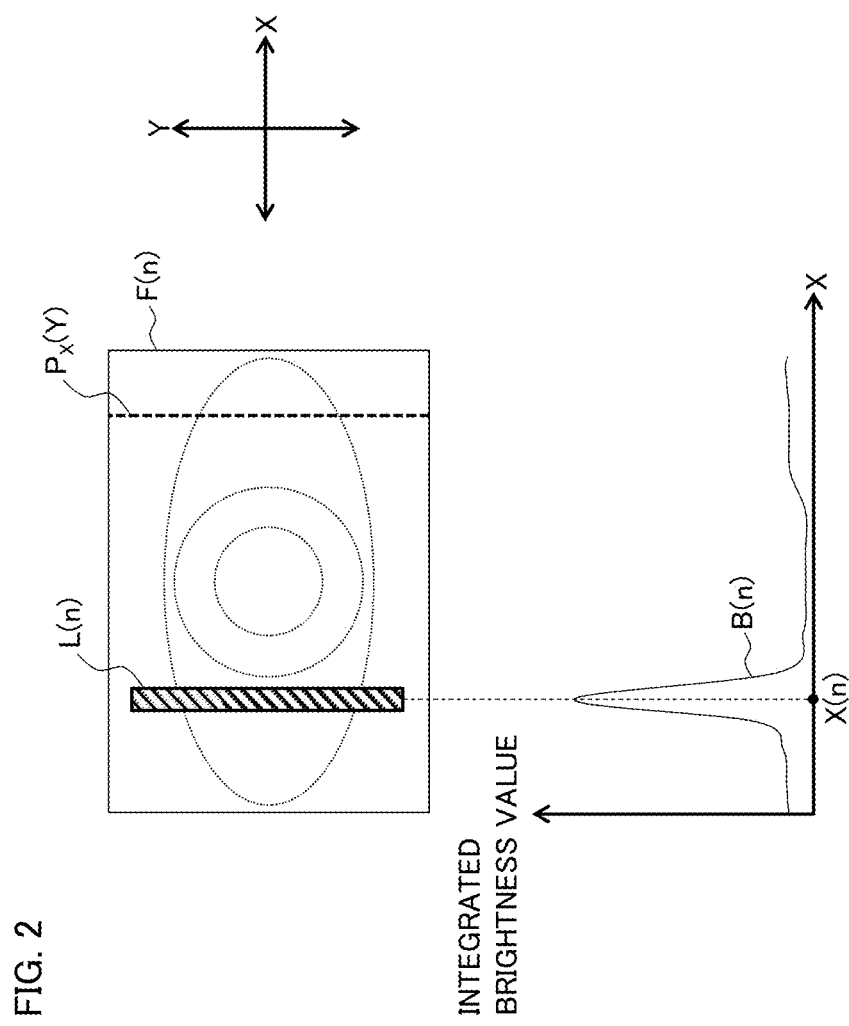
FIG. 2 is a diagram illustrating processing executed by an ophthalmic imaging apparatus according to an aspect example.

A specific example of processing executed by the first image analyzing unit 1030 will be now described with referring to FIG. 2. In the present example, the longitudinal direction of the cross section of the light beam of the slit light at the projection position on the subject's eye is oriented along the Y direction, and the slit light is moved in the X direction during slit scanning. The reference character F(n) denotes a single time series image (a single frame) acquired by the second image collecting unit 1020. Here, the index "n" is an integer equal to or greater than 1, and F(n) denotes the n-th time series image acquired in the order of acquisition sequence of the series of time series images. The slit light image L(n) is depicted in the time series image F(n).

When the time series image F(n) is input to the first image analyzing unit 1030, the first image analyzing unit 1030 executes the process of integrating (adding) the brightness values of the pixels of the time series image F(n) in the Y direction. More specifically, the first image analyzing unit 1030 divide the pixel group P(X, Y) constituting the time series image F(n) into a plurality of partial pixel groups $P_X(Y)$ corresponding to a plurality of X coordinates respectively, that is, into the plurality of partial pixel groups $P_X(Y)$ arranged (arrayed) in the Y direction. For each $P_X(Y)$, X is fixed and Y is defined over the range (the domain of definition) of the Y coordinates (the Y direction) of the time series image F(n). In this way, the plurality of partial pixel groups $P_X(Y)$ respectively corresponding to the plurality of X coordinates of the time series image F(n), is defined.

Next, the first image analyzing unit 1030 performs the integration of the brightness values of a plurality of pixels included in the corresponding partial pixel group $P_X(Y)$ for each X coordinate. By associating the X coordinate values with the integrated values of brightness (integrated brightness values), a graph B(n) showing a distribution of the integrated brightness values in the domain of definition of the time series image F(n) in the X direction. The graph B(n) is referred to as an integrated brightness value distribution.

In the time series image F(n), the slit light image L(n) is depicted brighter than other regions of this image. The first image analyzing unit 1030 detects the peak of the integrated brightness value distribution B(n), that is, detects the maximum value in the integrated brightness value distribution B(n), and then identifies the X coordinate X(n) corresponding to the peak detected. The X coordinate X(n) identified in this manner is recorded as the position (the X coordinate) of the slit light image L(n) in the time series image F(n).

By performing the series of processes described above for each time series image F(n), changes in the projection position of the slit light that is moved in the X direction during the slit scanning can be obtained. In other words, by performing the series of processes described above for each time series image F(n), time series shifts of the slit light during the slit scanning can be obtained. Since the data processing in the present example involves only arithmetic processing relating to brightness values, it has advantages such as high processing speed, short processing time, and requiring few processing resources. Another example of processing for the same purpose is to detect slit light images by applying segmentation to time series images. It should be noted that processing for the same purpose may include a freely selected or designed process for identifying a partial region of an image and/or a freely selected or designed process for identifying a position (location) in an image.

Some application examples of such slit light position detection will now be described. In some aspect examples in which an imaging protocol is of round-trip scanning, the projection position of the slit light at the X coordinate farthest from the X coordinate of the scan start position may be set to be a turnaround position (turnaround point, turning point, turning back point) of this round-trip scanning.

The difference between the X coordinate of the scan start position and the X coordinate of the turnaround position corresponds to the size of the scan area in the X direction. This size of the scan area in the X direction is the moving distance of the projection position of the slit light or the scan length. Similarly, the difference between the X coordinate of the scan start position and the X coordinate of the slit light farthest from the scan start position corresponds to the scan length also in the case in which an imaging protocol is not of round-trip scanning.

Further, some aspect examples may be configured to perform classification of a series of Scheimpflug images collected by round-trip scanning into the first group and the second group. The first group includes a series of Scheimpflug images collected during outward scanning. Here, the outward scanning is, for example, slit scanning from the left-most position (left edge, left end) to the right-most position (right edge, right end) of the scan area, that is, slit scanning from the scan start position to the turnaround position. The second group is a series of Scheimpflug images collected during return scanning. Here, the return scanning is, for example, slit scanning from the right-most position to the left-most position of the scan area, that is, slit scanning from the turnaround position to the scan end position. Note that a Scheimpflug image corresponding to the turnaround position may be included in both the first group and the second group.

In addition, some aspect examples may be configured to perform a process of constructing a three dimensional image on the basis of the first group (and a group of images used for interpolation of the first group), and a process of constructing a three dimensional image on the basis of the second group (and a group of images used for interpolation of the second group). Some other aspect examples may be configured to perform a process of selecting, from the first group and the second group, a series of Scheimpflug images corresponding to the area from the right-most position to the left-most position of the scan area, and a process of constructing a three dimensional image on the basis of this selected series of Scheimpflug images (and a group of images used for interpolation of this series of Scheimpflug images).

In spatial image interpolation for constructing a three dimensional image and a rendered image, time series shifts of (a projection position of) slit light may be used to determine the number (quantity) of images interpolated, that is, the number (quantity) of frames interpolated mentioned above. This will be described in detail in the description of the image interpolating unit 1040.

As described above, the first image analyzing unit 1030 is configured to execute analysis of a series of time series images collected by the second image collecting unit 1020 to determine time series shifts of the slit light during the slit scanning performed by the first image collecting unit 1010. In addition to this, the first image analyzing unit 1030 may be configured to execute analysis of a series of time series images collected by the second image collecting unit 1020 to determine time series shifts (time series displacements, time series movements) of the subject's eye during the period of time in which the slit scanning is being carried out. The time series shifts of the subject's eye is a time series change (chronological change, temporal change, time-dependent change) in the position of the subject's eye relative to the ophthalmic imaging apparatus 1000, more specifically, relative to the first image collecting unit 1010, for example. By using the time series shifts of the subject's eye obtained in this way, it becomes possible to detect, with a higher degree of accuracy and a higher degree of precision, a relative position between the subject's eye and the slit light during the period of time in which the slit scanning is being performed, that is, a time series change in this relative position during the slit scanning.

The first image analyzing unit 1030 may be configured to analyze each of the time series images collected by the second image collecting unit 1020 to determine the position of the subject's eye at a time point corresponding to this time series image. Further, the first image analyzing unit 1030 may be configured to arrange, in chronological (time series) order, a series of positions of the subject's eye obtained from the series of time series images in this manner, thereby determining time series shifts of the subject's eye during the period of time while the series of time series images are being collected, that is, during the period of time while the series of Scheimpflug images are being collected in parallel with the collection of the series of time series images.

Figure 3:
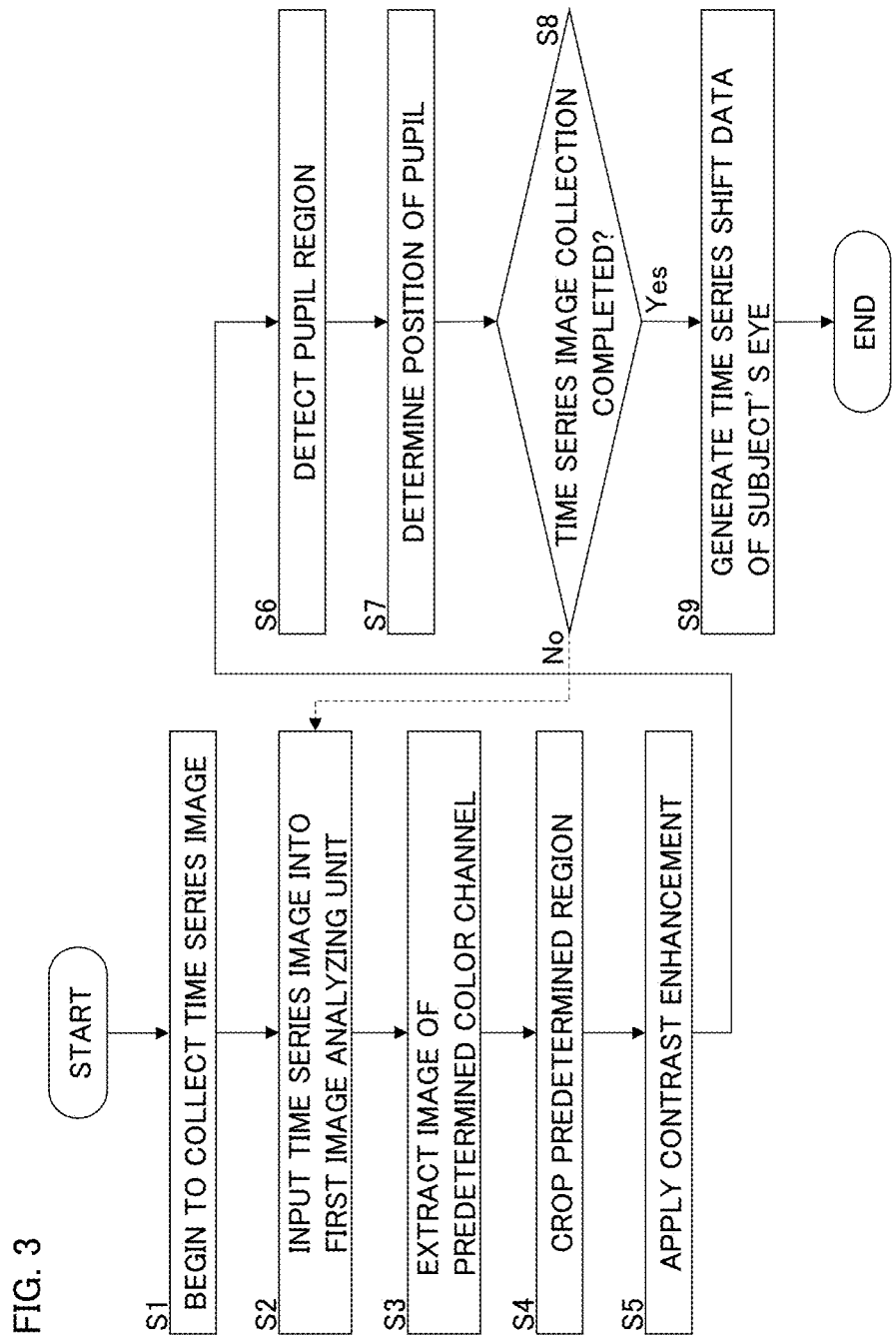
FIG. 3 is a flowchart illustrating processing executed by an ophthalmic imaging apparatus according to an aspect example.

An example of processing executed by the first image analyzing unit 1030 for determination of time series shifts of the subject's eye will now be described with reference to FIG. 3. A position of the subject's eye in the present example is defined with reference to a feature point of the pupil such as the center of the pupil, the center of gravity of the pupil, or a predetermined position on the contour of the pupil. Further, let a time series image of the present example be a color image (RGB image). Note that a time series image of some other examples may be a grayscale image; if this is the case, the step S3 in FIG. 3 is omitted, for example.

After the commencement of collection of time series images by the second image collecting unit 1020 in parallel with collection of Scheimpflug images by the first image collecting unit 1010 (S1), the time series images sequentially acquired by the second image collecting unit 1020 are input into the first image analyzing unit 1030 sequentially and in real time (S2).

The first image analyzing unit 1030 extracts an image of a predetermined color channel from each of the time series images inputted (each of the RGB images) (S3). According to the studies by the inventors of the present disclosure, it is found that a red channel image (an image of the red channel, a red component image, an R image) exhibits the clearest pupil boundary (pupil contour). On the basis of this finding, the first image analyzing unit 1030 of the present example extracts the red channel image from the three color channel images of each of the time series images inputted.

Next, the first image analyzing unit 1030 crops a predetermined region from the R image extracted in the step S3 (S4). This predetermined region (cropped region) in the present example is a region in which the image of the pupil fits. The cropped region may be a region of a predetermined size. For example, the cropped region may be a region with a size of 512 pixels by 512 pixels. The preset size of the cropped region may be determined based on, for example, any one or more of design data of the optical system of the second image collecting unit 1020, the working distance of the ophthalmic imaging apparatus 1000 (the working distance of the second image collecting unit 1020), a standard pupil size (standard pupil diameter), and other parameters. Also, based on the time series images (or an image(s) of the subject's eye acquired in advance by the second image collecting unit 1020), a custom-made cropped region size for this subject's eye may be determined Next, the first image analyzing unit 1030 applies contrast enhancement to the cropped region obtained in the step S4 (S5). This contrast enhancement may be, for example, histogram equalization. More specifically, the contrast enhancement may be any of the following techniques: adaptive histogram equalization; contrast limited adaptive histogram equalization (CLAHE); multipeak histogram equalization (MPHE); and multipurpose beta optimized bihistogram equalization (MBOBHE). Any contrast enhancement technique other than histogram equalization may also be used.

Next, the first image analyzing unit 1030 detects a pupil image (pupil region) from the cropped region whose contrast has been enhanced in the step S5 (S6). The technique for detecting the pupil region may be freely determined. In some examples, any of the following image segmentation techniques may be used: image segmentation using CNN trained by machine learning to input an ocular image and to output a detection result of a pupil region; and graph-based image segmentation using Dijkstra's algorithm.

Next, the first image analyzing unit 1030 determines the position of the pupil based on the pupil region detected in the step S6 (S7). The position of the pupil determined in the present step may be the position (coordinates) of the above-mentioned feature point of the pupil determined in advance, and be treated as the position of the subject's eye at a time point when a corresponding time series image is acquired. The information obtained as the position of the pupil, which is treated as the position of the subject's eye, in the present step may include at least an X coordinate and may further include a Y coordinate. Here, the X coordinate represents a position in the moving direction of the scan light during the slit scanning and the Y coordinate represents a position in the longitudinal direction of the cross section of the slit light. As described above, in the case in which the second image collecting unit 1020 includes the two anterior segment cameras, the first image analyzing unit 1030 may be configured to generate three dimensional position information, which includes an X coordinate, a Y coordinate, and a Z coordinate, as a position of the pupil (a position of the subject's eye). In some examples, the position information of the subject's eye obtained in the present step is associated with order information (sequence information) of a corresponding time series image or with information representing a time point (time information) of a corresponding time series image, and then stored in a storage device (not shown in the drawings).

The series of processes of the steps S3 to S7 is repeatedly applied to time series images sequentially acquired by the second image collecting unit 1020 until the collection of time series images performed by the second image collecting unit 1020 is completed, and/or, until the collection of Scheimpflug images performed by the first image collecting unit 1010 is completed or until the user instructs the completion of the series of processes of the steps S3 to S7 (S8: No). In some aspect examples, the series of processes of the steps S3 to S7 is applied to each and every time series image acquired by the second image collecting unit 1020. In some other aspect examples, on the other hand, the series of processes of the steps S3 to S7 is applied only to a proper subset of the set of all time series images collected by the second image collecting unit 1020. In other words, in some other aspect examples, the series of processes of the steps S3 to S7 is applied only to a time series image group selected or extracted from all time series images collected by the second image collecting unit 1020.

When the collection of time series images performed by the second image collecting unit 1020 is completed (and/or, when the collection of Scheimpflug images performed by the first image collecting unit 1010 is completed or when the user instructs the completion of the series of processes), the process moves on to the step S9. (S8: Yes).

At the stage when the process has moved to the step S9, a series of position information of the subject's eye corresponding to the series of time series images collected by the second image collecting unit 1020, is stored. More generally, at the stage when the process has moved to the step S9, a series of position information of the subject's eye corresponding to at least part of the series of time series images collected by the second image collecting unit 1020, is stored. Each position information of the series of position information of the subject's eye is associated with order information of a corresponding time series image or with time information of a corresponding time series image. The first image analyzing unit 1030 may arrange (dispose) the series of position information of the subject's eye on the time axis based on the series of order information or the series of time information, thereby generating data representing time series shifts of the subject's eye (S9). Note that this time series shift data of the subject's eye may include information representing a correspondence between the series of position information of the subject's eye and one of the series of order information and the series of time information which have already been acquired by the time the process has moved on to the step S9. Also note that the time series shift data of the subject's eye may include any data obtained from this correspondence. The time series shift data of the subject's eye generated in the step S9 is stored in a storage device (not shown in the drawings) (END).

In spatial image interpolation for constructing a three dimensional image and a rendered image, time series shifts of the subject's eye may be used to determine the number of images interpolated (the number of frames interpolated described above). This will be described in detail in the description of the image interpolating unit 1040.

The image interpolating unit 1040 is configured to perform interpolation of the series of Scheimpflug images collected by the first image collecting unit 1010, on the basis of the time series shifts of the slit light acquired by the first image analyzing unit 1030. This makes it possible to construct an image of the three dimensional region (three dimensional image) of the subject's eye to which the slit scanning is applied, based on a plurality of images including the series of Scheimpflug images collected and a group of images interpolating the series of Scheimpflug images collected, without narrowing the intervals between the series of Scheimpflug images collected. The aspect ratio of the three dimensional image constructed in this way corresponds to the actual morphology of the anterior segment of the subject's eye. The same applies to a rendered image constructed from this three dimensional image.

As described above, in some aspect examples, the slit scanning performed by the first image collecting unit 1010 and the repetitive photography of the subject's eye performed by the second image collecting unit 1020 may be performed in synchronization with each other.

In such an aspect example, the image interpolating unit 1040 may be configured to perform association between a series of Scheimpflug images obtained by the slit scanning and a series of time series images obtained by the repetitive photography based on the synchronization between the slit scanning and the repetitive photography. In some examples, this association may be performed based on the synchronization control between the first image collecting unit 1010 and the second image collecting unit 1020. This association of some examples may be performed in such a manner as to make a correspondence between a Scheimpflug image and a time series image that have a small difference in acquisition time points from each other.

Furthermore, the image interpolating unit 1040 may perform the interpolation of the series of Scheimpflug images based further on the correspondence (the association) between the series of Scheimpflug images and the series of time series images obtained in the manner described above. In other words, the image interpolating unit 1040 may perform the interpolation of the series of Scheimpflug images based on the correspondence (the association) as well as the time series shifts of the slit light.

According to the aspect examples configured in this manner, image interpolation can be performed with a higher degree of accuracy and a higher degree of precision from chronological point of view, through the utilization of the synchronization between the slit scanning and the repetitive photography. As a result, it becomes possible to perform image interpolation with a higher degree of accuracy and a higher degree of precision from spatial point of view.

Several examples of the configuration, several examples of the functions, several examples of modifications, and other matters and items pertaining to the image interpolating unit 1040 will be given later.

As mentioned above, the first image collecting unit 1010 in some aspect examples includes the first photography system and the second photography system that are configured to perform photography of the three dimensional region of the subject's eye in the slit scanning from mutually different directions. A plurality of Scheimpflug images collected by the first photography system in this slit scanning is referred to as the first Scheimpflug image group, and a plurality of Scheimpflug images collected by the second photography system in this slit scanning is referred to as the second Scheimpflug image group. A series of Scheimpflug images collected by this slit scanning includes the first Scheimpflug image group and the second Scheimpflug image group.

In the slit scanning executed by the first image collecting unit 1010 of such aspect examples, the photography of the subject's eye by the first photography system and the photography of the subject's eye by the second photography system are performed in parallel with each other. In other words, the first image collecting unit 1010 of such aspect examples performs photography by means of the first photography system and photography by means of the second photography system in parallel with one another while moving the projection position of the slit light relative to a three dimensional region of the subject's eye.

Further, the first image collecting unit 1010 may be configured to perform photography by means of the first photography system (collection of Scheimpflug images by means of the first photography system) and photography by means of the second photography system (collection of Scheimpflug images by means of the second photography system) in synchronization with each other. By referring to this synchronization relationship (synchronization correspondence), association between the first Scheimpflug image group and the second Scheimpflug image group can be easily achieved without using data processing such as image processing. This association is performed, for example, in such a manner as to associate Scheimpflug images that have a small difference in acquisition time points with each other.

In such aspect examples, the ophthalmic imaging apparatus 1000 may be configured to perform reconstruction of a series of Scheimpflug images corresponding to the slit scanning from the first Scheimpflug image group and the second Scheimpflug image group by referring to the synchronization relationship between the photography performed by the first photography system and the photography performed by the second photography system.

Figure 4:
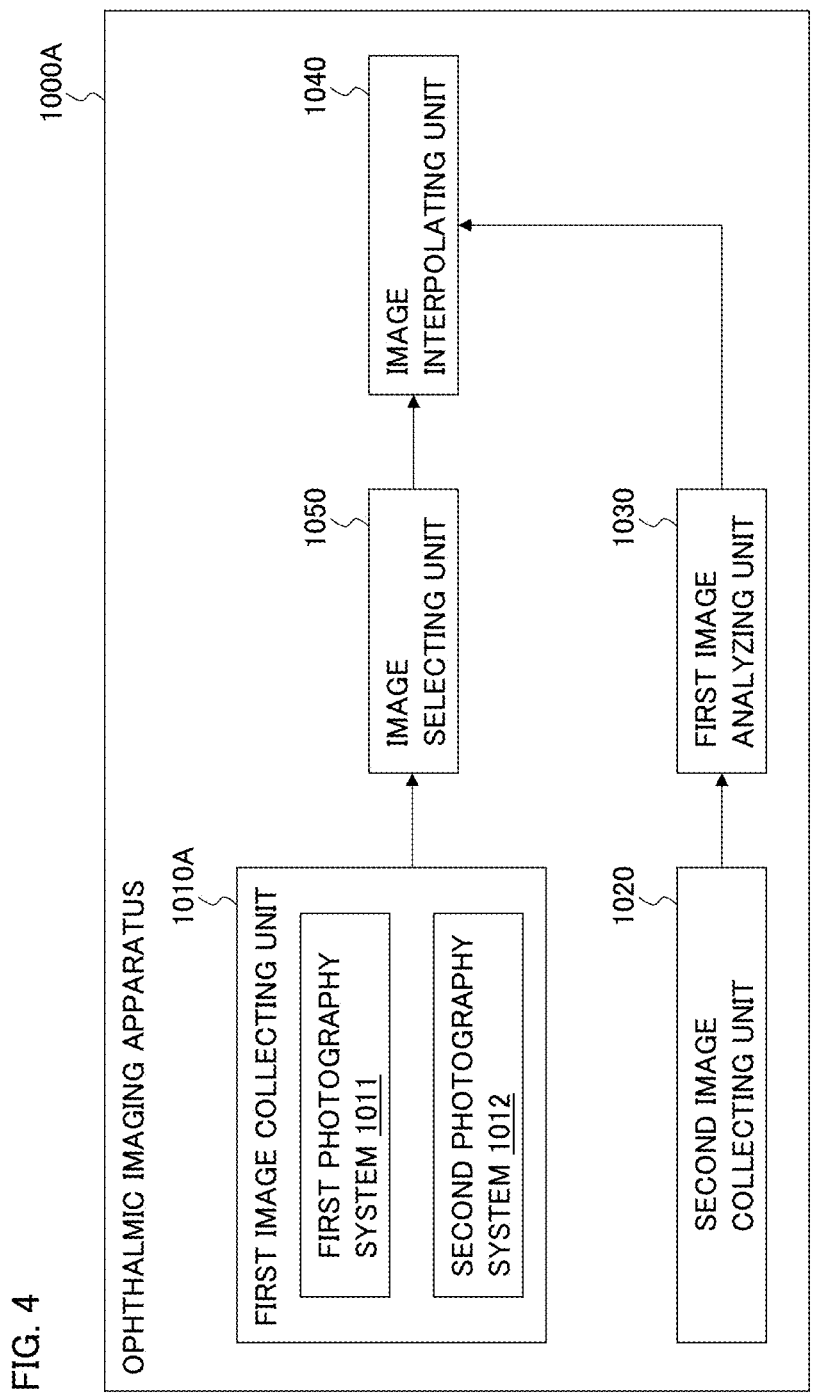
FIG. 4 is a diagram of a configuration of an ophthalmic imaging apparatus according to an aspect example.

FIG. 4 shows the configuration of a modification example of the ophthalmic imaging apparatus 1000 having a function of reconstructing a series of Scheimpflug images. The first image collecting unit 1010A of the ophthalmic imaging apparatus 1000A of the present example includes the first photography system 1011 and the second photography system 1012. The first image collecting unit 1010A is configured to perform photography by means of the first photography system 1011 and photography by means of the second photography system 1012 in a mutually synchronized manner.

The ophthalmic imaging apparatus 1000A further includes the image selecting unit 1050. The image selecting unit 1050 is disposed between the first image collecting unit 1010A and the image interpolating unit 1040. The image selecting unit 1050 is configured to perform selection of another series of Scheimpflug images corresponding to the slit scanning, by which the first Scheimpflug image group and the second Scheimpflug image group have been collected, from the first Scheimpflug image group and the second Scheimpflug image group, on the basis of a correspondence between the first Scheimpflug image group and the second Scheimpflug image group determined based on the synchronization between the photography performed by the first photography system 1010A and the photography performed by the second photography system 1020A. In short, the image selecting unit 1050 is configured to execute reconstruction of a series of Scheimpflug images from the first Scheimpflug image group and the second Scheimpflug image group that are collected by the first photography system 1011 and the second photography system 1012 respectively. The image interpolating unit 1040 of the present example is configured to perform interpolation of the series of Scheimpflug images obtained by the reconstruction carried out by the image selecting unit 1050.

The technique of this image selection processing executed by the image selecting unit 1050 may be freely determined or designed. In some examples, the technique of the image selection processing may be determined and/or selected based on a predetermined condition and/or a predetermined parameter. Examples of the predetermined condition and the predetermined parameter include the configurations and/or the arrangements of the first photography system 1011 and the second photography system 1012, the purpose and/or the use of image selection, and the configuration and/or the function of the image interpolating unit 1040.

Figure 5:
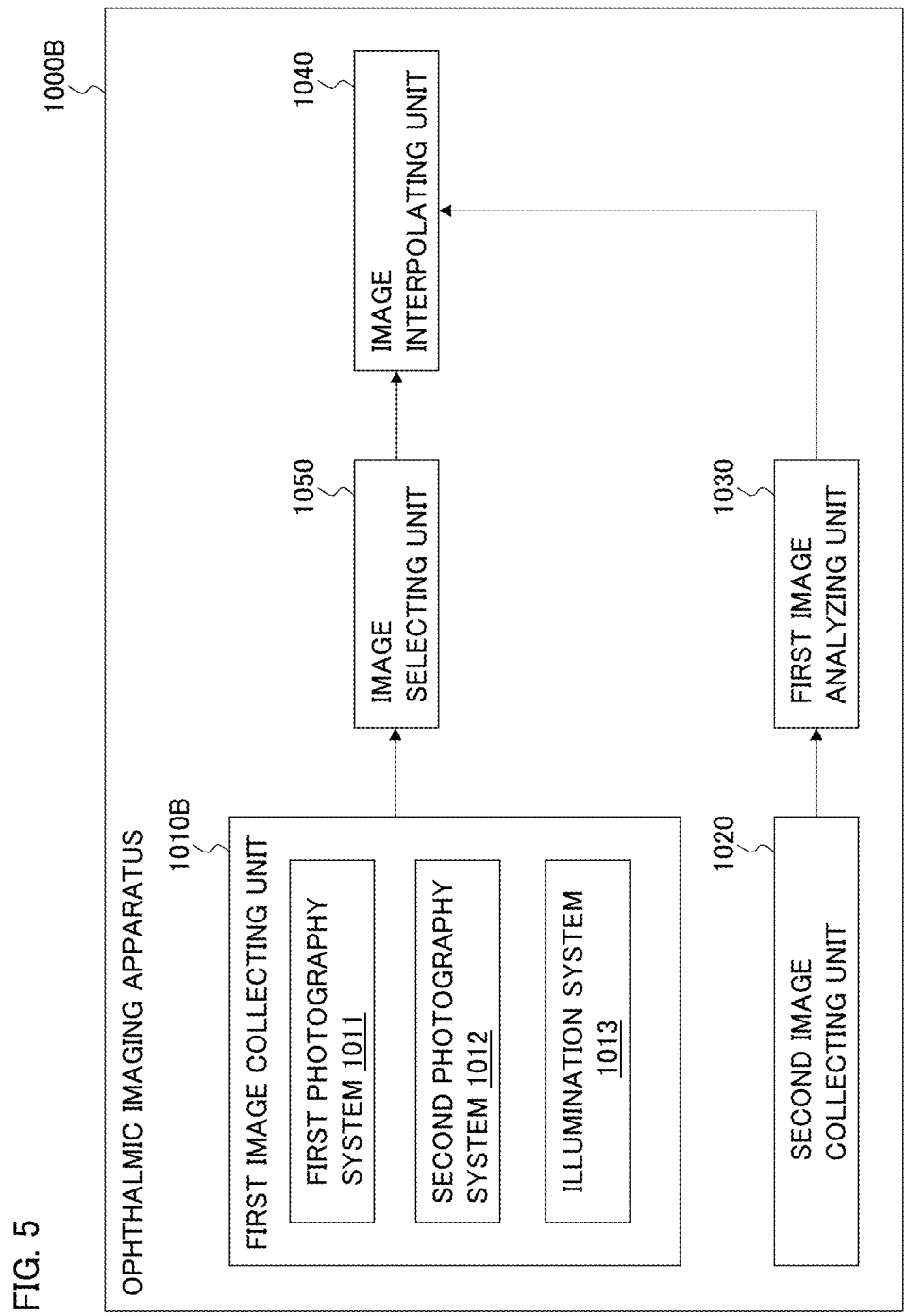
FIG. 5 is a diagram of a configuration of an ophthalmic imaging apparatus according to an aspect example.

FIG. 5 shows the configuration of a modified example of the ophthalmic imaging apparatus 1000A that has an image selection function. The first image collecting unit 1010B of the ophthalmic imaging apparatus 1000B of the present example includes the illumination system 1013 in addition to the first photography system 1011 and the second photography system 1012. The first photography system 1011 and the second photography system 1012 are the same as those of the first image collecting unit 1010A of FIG. 4. The illumination system 1013 is configured to project slit light onto a three dimensional region of the subject's eye. The image selecting unit 1050 in the present example is disposed between the first image collecting unit 1010B and the image interpolating unit 1040.

The first image collecting unit 1010B performs the photography performed by the first photography system 1011 and the photography performed by the second photography system 1012 in synchronization with each other. Further, in the present example, the optical axis of the first photography system 1011 and the optical axis of the second photography system 1012 are arranged (oriented) in an oblique manner toward mutually opposite directions relative to the optical axis of the illumination system 1013. In some examples, the optical axis of the first photography system 1011 is oriented in an oblique manner toward the left direction relative to the optical axis of the illumination system 1013 while the optical axis of the second photography system 1012 is oriented in an oblique manner toward the right direction relative to the optical axis of the illumination system 1013. The first photography system 1011 and the second photography system 1012 arranged in this way are sometimes referred to as a left photography system and a right photography system, respectively.

The oblique angle of the optical axis of the first photography system 1011 relative to the optical axis of the illumination system 1013 and the oblique angle of the optical axis of the second photography system 1012 relative to the optical axis of the illumination system 1013, may be equal to or different from each other. Further, these oblique angles may be fixed or variable.

The illumination system 1013 of the present example is configured and disposed to project slit light to the subject's eye from the front direction. Here, the longitudinal direction of the cross section of the slit light is oriented in the Y direction. In addition, the first image collecting unit 1010B of the present example is configured to move the illumination system 1013, the first photography system 1011, and the second photography system 1012 in an integrated manner in the X direction, thereby applying slit scanning to a three dimensional region of the anterior segment of the subject's eye.

The image selecting unit 1050 in the present example is configured to perform selection of a plurality of Scheimpflug images containing no artifact from the first Scheimpflug image group and the second Scheimpflug image group based on the correspondence between the first Scheimpflug image group collected by the first photography system 1011 and the second Scheimpflug image group collected by the second photography system 1012, thereby performing selection of another series of Scheimpflug images corresponding to slit scanning by which the first Scheimpflug image group and the second Scheimpflug image group are collected. This artifact may be any kind of artifact. In the case in which anterior segment scanning is executed as in the present example, the artifact may be an artifact caused by corneal reflection (corneal reflection artifact). Some examples of processing executed by the image selecting unit 1050 will now be described.

Projection positions of the slit light at which corneal reflection artifacts occur differ between the left photography system and the right photography system. That is, Scheimpflug images (frames) in which corneal reflection artifacts occur differ between a Scheimpflug image group acquired by the left photography system and a Scheimpflug image group acquired by the right photography system. For example, consider the case in which the longitudinal direction of the cross section of slit light is oriented in the Y direction, this slit light is projected onto the subject's eye from the front direction, and slit scanning is performed by moving the illumination system 1013, the first photography system 1011, and the second photography system 1012 in an integrated manner in the x direction simultaneously with the slit light projection. In this case, the corneal reflection light of the slit light tends to enter the left photography system when the slit light is projected onto a position located on the left side of the corneal apex (a position off to the left relative to the corneal apex), while the corneal reflection light of the slit light tends to enter the right photography system when the slit light is projected onto a position located on the right side of the corneal apex (a position off to the right relative to the corneal apex).

Taking this fact (phenomenon) into account, the image selecting unit 1050 in some aspect examples may first perform the following processes: a process of identifying a Scheimpflug image corresponding to the corneal apex (referred to as the first corneal apex image) from among the first Scheimpflug image group collected by the first photography system 1011 in the role of the left photography system; and a process of identifying a Scheimpflug image corresponding to the corneal apex (referred to as the second corneal apex image) from among the second Scheimpflug image group collected by the second photography system 1012 in the role of the right photography system.

In some aspect examples, the processing of identifying a corneal apex image may include the following processes: a process of detecting an image corresponding to the corneal surface from each Scheimpflug image included in the first Scheimpflug image group; a process of identifying a pixel closest to the ophthalmic imaging apparatus 10006 based on the Z coordinates of the pixels of the images corresponding to the corneal surface detected from the first Scheimpflug image group; and a process of selecting, from the first Scheimpflug image group, a Scheimpflug image that includes the pixel identified, and setting the selected Scheimpflug image to be the first corneal apex image. The same applies to the determination of the second corneal apex image.

Next, the image selecting unit 1050 selects a Scheimpflug image group located to the right of the first corneal apex image from the first Scheimpflug image group, and selects a Scheimpflug image group located to the left of the second corneal apex image from the second Scheimpflug image group. Then, the image selecting unit 1050 constructs a series of Scheimpflug images consisting of the two Scheimpflug image groups selected from the first and second Scheimpflug image groups (and also consisting of the first corneal apex image and/or the second corneal apex image). This processing yields a series of Scheimpflug images not only that represents an area covering the three dimensional region of the anterior segment to which the slit scanning has been applied and but also that do not contain (or unlikely contain) a corneal reflection artifact.

Another example of the processing of identifying the corneal apex image will now be described. The image selecting unit 1050 in some aspect examples may be configured to execute judgement whether a corneal reflection artifact is contained in one or both of two images acquired at substantially the same time point (substantially simultaneously) by the first photography system 1011 (e.g., the left photography system) and the second photography system 1012 (e.g., the right photography system). This corneal reflection artifact determination processing (artifact detection processing) may include a freely determined, selected, or designed image analysis. In some examples, the corneal reflection artifact determination processing includes thresholding of brightness information assigned to pixels. The processing of determining two images acquired at substantially the same time point may be executed on the basis of a synchronization relationship between photography performed by the first photography system 1011 and photography performed by the second photography system 1012.

In some examples, the thresholding used for the artifact determination processing may include a process of identifying one or more pixels to which brightness values exceeding a preset threshold value have been assigned. In some typical examples, this threshold value is set to a value higher than a brightness value of a slit light image (an image corresponding to a region onto which the slit light is projected) in an image. By employing a threshold value set in this way, the image selecting unit 1050 is configured to be capable of determining an image brighter than a slit light image as an artifact without determining the slit light image as an artifact. An image brighter than a slit light image in a Scheimpflug image is likely to be caused by specular reflection at the cornea. Therefore, an artifact detected by the image selecting unit 1050 of the present example is likely to be a corneal reflection artifact.

The image selecting unit 1050 may be configured to perform any image analysis applicable to the artifact determination processing other than thresholding, such as pattern recognition, segmentation, or edge detection. In general, any information processing techniques or technologies such as image analysis, image processing, artificial intelligence, or cognitive computing, can be applied to the artifact determination processing.

If a result of the artifact determination processing shows that one of two images acquired substantially simultaneously by the first photography system 1011 and the second photography system 1012 contains an artifact, the image selecting unit 1050 selects the other image that contains no artifact, in other words, the image selecting unit 1050 selects the image of the two images that is not the image determined to contain the artifact.

If a result of the artifact determination shows that both of two images acquired substantially simultaneously by the first photography system 1011 and the second photography system 1012 contain an artifact, the image selecting unit 1050 may, for example, perform estimation (evaluation, assessment) of the magnitude (impact, degree, extent, scale) of the adverse effect this artifact has on medical observation or medical diagnosis, and selection of an image with the smaller adverse effect. This estimation may be performed based on, for example, one or more of the following conditions: the size of an artifact; the intensity of an artifact; the shape of an artifact; and the position of an artifact. Typically, artifacts that are large in size, artifacts that are high in intensity, artifacts that are located in a region of interest such as a slit light image, and artifacts that are located in the vicinity of a region of interest, are evaluated as having large adverse effects.

Note that in the case in which both of two images contain artifacts, the artifact removal technique disclosed in Japanese Unexamined Patent Application Publication No. 2019-213733 (PCT International Publication No. 2019/240149) pertaining to a patent application filed by the applicant of the present application, may be employed.

These modification examples are capable of providing an image of a three dimensional region of the subject's eye that does not contain artifacts being hindrance to medical activities and medical processing such as medical observation, medical analysis, and medical diagnosis. Some examples may be capable of constructing a three dimensional image of the subject's eye based on an image group that does not contain artifacts.

Even if two images are obtained by performing photography of substantially the same region of the subject's eye, there are cases in which the size of a predetermined ocular site depicted in an image obtained by the left photography system and the size of the same predetermined ocular site depicted in an image obtained by the right photography system differ from each other. For example, there are cases in which the thicknesses of the cornea depicted may be different from each other in a left image and a right image obtained by performing photography of substantially the same region of the subject's eye with the left photography system and the right photography system, respectively. Even in such a case, it is possible, by the present aspect example, to adjust (equalize) the sizes of the same ocular site by using the image selecting unit 1050.

Next, several configuration examples, several functional examples, and several modification examples of the image interpolating unit 1040 will be described.

In some aspect examples, the image interpolating unit 1040 may be configured to perform spatial image interpolation using the optical flow described above. More specifically, the image interpolating unit 1040 of some aspect examples may be configured to receive a series of Scheimpflug images collected by the first image collecting unit 1010 (or a series of Scheimpflug images reconstructed by the image selecting unit 1050), to represent a shift of the subject's eye as a vector by applying the optical flow to the series of Scheimpflug images received, and to perform interpolation of the series of Scheimpflug images based on this vector representation.

According to the present example, the optical flow technique, which is used in general for analyzing the movement (motion, temporal change) of an object, can be used to acquire the spatial change of the object, thereby making it possible to implement spatial image interpolation of a series of Scheimpflug images.

In some aspect examples, the image interpolating unit 1040 may be configured to perform spatial image interpolation using an inference model constructed in advance. More specifically, the image interpolating unit 1040 of some aspect examples may be configured to receive a series of Scheimpflug images collected by the first image collecting unit 1010 (or a series of Scheimpflug images reconstructed by the image selecting unit 1050), to input the series of Scheimpflug images into the inference model, and to perform interpolation of the series of Scheimpflug images based on an output from the inference model.

The inference model used for spatial image interpolation in some examples is constructed in advance by applying, to a neural network, machine learning with training data that includes at least a Scheimpflug image of an eye. The inference model constructed in such a manner is configured to receive an input of two or more Scheimpflug images respectively representing two or more different locations (sites, places, parts, positions, cross sections) of the same eye, and to output an interpolated image obtained by spatial interpolation of the two or more Scheimpflug images. This interpolated image (spatially interpolated image) output from the inference model may only include one or more images added to the two or more Scheimpflug images inputted (that is, may only include one or more images created by the image interpolating unit 1040), or may include both the one or more added images and the two or more Scheimpflug images inputted.

Figure 6A:
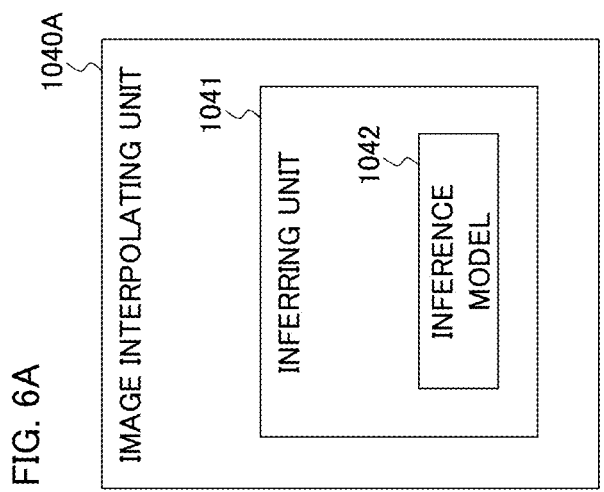
FIG. 6A is a diagram of a configuration of an ophthalmic imaging apparatus according to an aspect example.

FIG. 6A shows an example of the image interpolating unit 1040 configured to perform spatial image interpolation using an inference model. The image interpolating unit 1040A of the present example includes the inferring unit 1041 configured to perform spatial image interpolation using the inference model 1042.

The inference model 1042 is constructed by applying, to a neural network, machine learning with training data including at least a Scheimpflug image of an eye. The device for constructing the inference model 1042 (inference model construction device) may be disposed in the ophthalmic imaging apparatus 1000 (1000A, 1000B), or in a peripheral device (a peripheral computer or the like) of the ophthalmic imaging apparatus 1000 (1000A, 1000B). Alternatively, the inference model construction device may be a computer other than the peripheral computer.

Figure 6B:
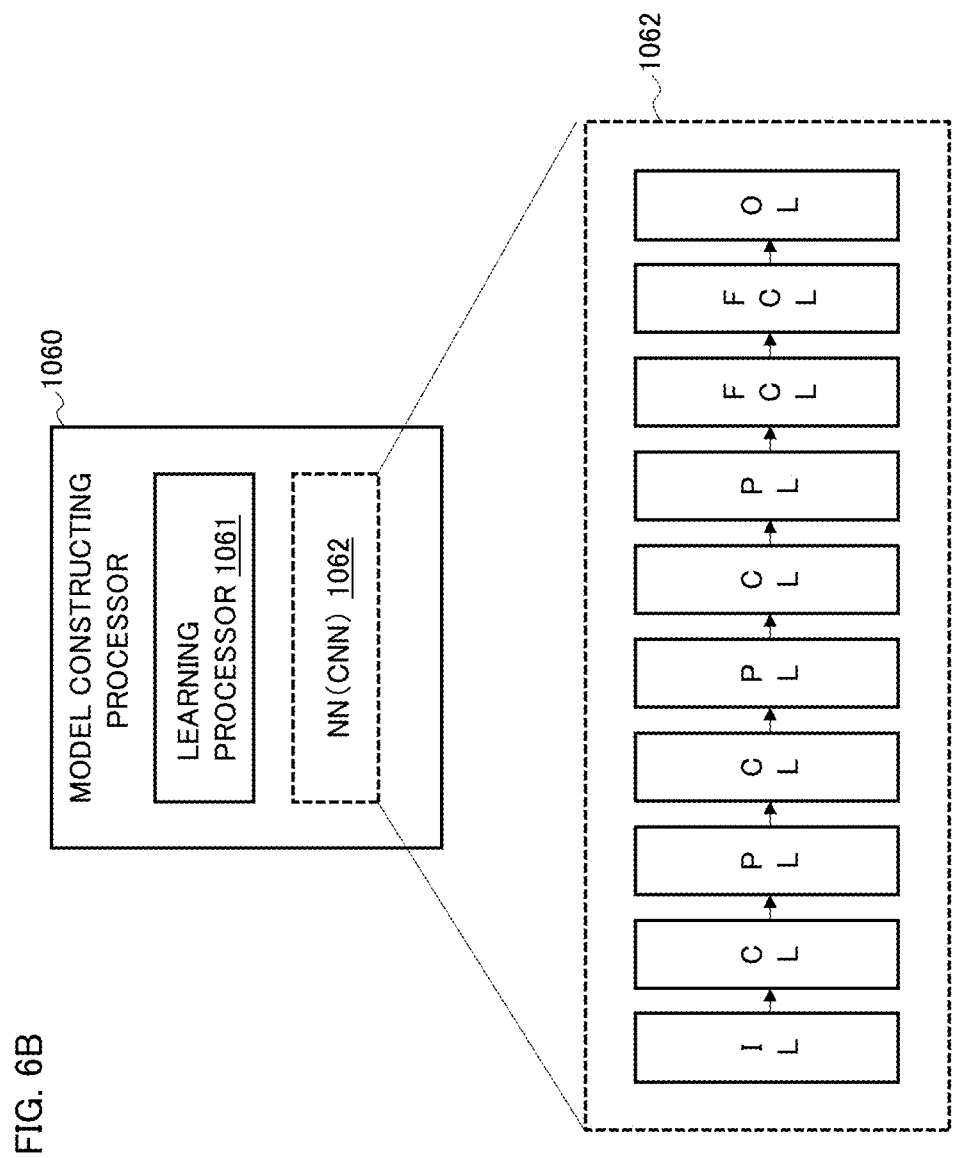
FIG. 6B is a diagram of a configuration of an ophthalmic imaging apparatus according to an aspect example.

The model constructing processor 1060 shown in FIG. 6B is an example of an inference model construction device, and includes the learning processor 1061 and the neural network 1062.

In some typical examples, the neural network 1062 includes a convolutional neural network (CNN). FIG. 6B shows an example of the structure of this convolutional neural network.

An image is input to the input layer of the neural network 1062. Behind the input layer, a plurality of pairs of a convolutional layer and a pooling layer is disposed. While three pieces of pairs of a convolution layer and a pooling layer are provided in the neural network 1062 shown in FIG. 6B, the number of the pairs may be freely determined.

In the convolutional layer, a convolution operation is performed to detect or extract a feature (e.g., contour) from the input image. This convolution operation is a multiply-accumulate operation (a multiply-add operation, a product-sum operation) on the input image. This multiply-accumulate operation is performed with a filter function (a weight coefficient, a filter kernel) having the same dimension as the input image. In the convolutional layer, the convolution operation is applied to individual parts (individual sections, individual portions) of the input image. More specifically, the convolutional layer is configured to calculate a product by multiplying the value of each pixel in a partial image, to which the filter function has been applied, by the value (weight) of the filter function corresponding to this pixel, and then calculate the sum of the products over a plurality of pixels in this partial image. The sum of products obtained in this way is substituted for the corresponding pixel in an image to be output from the convolutional layer. By repetitively performing such multiply-accumulate operation in parallel with moving sites (parts) to which the filter function is applied (that is, in parallel with changing or switching partial images of the input image), a result of the convolution operation for the entire input image is obtained. The convolution operation performed in this way gives a large number of images in which various features have been extracted using a large number of weight coefficients. This means that a large number of filtered images, such as smoothed images and edge images, are obtained. The large number of images generated by the convolutional layer are referred to as feature maps (or activation maps).

The pooling layer executes data compression (e.g., data thinning) of the feature maps generated by the convolutional layer disposed at the immediately preceding position. More specifically, the pooling layer calculates statistical values in predetermined neighboring pixels of a predetermined pixel of interest in an input feature map at each predetermined pixel intervals, and outputs an image having a size smaller than the input feature map. The statistical values applied to the pooling operation may be maximum values (max pooling) or average values (average pooling), for example. The value of the pixel intervals applied to the pooling operation is referred to as a stride.

In general, a convolutional neural network extracts many features from an input image by executing processing using a plurality of pairs of a convolutional layer and a pooling layer.

A fully connected layer is disposed behind the most downstream pair of a convolutional layer and a pooling layer. While two pieces of fully connected layers are provided in the structural example shown in FIG. 6B, the number of fully connected layers may be freely determined.

The fully connected layer executes processing such as image classification, image segmentation, or regression using the features compressed by the combination of convolution and pooling. An output layer is disposed behind the most downstream fully connected layer. The output layer gives an output result.

Some aspect examples may employ a convolutional neural network including no fully connected layer. For example, some aspect examples may employ a fully convolutional network (FCN). Some aspect examples may include a support vector machine, a recurrent neural network (RNN), or any other models. Further, machine learning applied to the neural network 1062 may include transfer learning. In other words, the neural network 1062 may include a neural network that has already been trained using other training data (training images) and whose parameters have been adjusted. Further, the model constructing processor 1060 (the learning processor 1061) may be configured in such a manner that fine tuning can be applied to a trained neural network (at least part of the neural network 1062). The neural network 1062 may be constructed, for example, using a known open source neural network architecture.

The learning processor 1061 applies machine learning with training data to the neural network 1062. In the case in which the neural network 1062 includes a convolutional neural network, parameters adjusted by the learning processor 1061 include, for example, filter coefficients of one or more convolutional layers therein and connection weights and offsets of one or more fully connected layers therein.

The training data of the present example may include one or more Scheimpflug images acquired from one or more eyes, as described above. Since the one or more Scheimpflug images of the one or more eyes are of the same type as an image inputted to the inferring unit 1041, using such training data allows the quality (accuracy, precision, etc.) of an output of the inferring unit 1041 to be improved more significantly in comparison to the case in which machine learning is performed using training data consisting only of images of the types other than an image inputted to the inferring unit 1041.

The training data may include two or more Scheimpflug images that respectively represents two or more different locations (sites, places, parts, positions, cross sections) of the same eye. Machine learning usable in this case may be executed, for example, in such a manner as to optimize an output in response to an input of such two or more Scheimpflug images, more specifically, to optimize an interpolated image (spatially interpolated image) obtained by spatial interpolation of the two or more Scheimpflug images. Since a Scheimpflug image group of the present example consists of images of the same type as a series of Scheimpflug images inputted to the inferring unit 1041, the quality of an output of the inferring unit 1041 can be further improved.

The types of images included in training data are not limited to Scheimpflug images. In some examples, images of any of the following types may be included in training data: an image acquired using other kinds of ophthalmic modalities (e.g., fundus camera, OCT apparatus, SLO, surgical microscope); an image acquired using any kinds of diagnostic imaging modalities of any clinical departments other than ophthalmology (e.g., ultrasonic diagnostic apparatus, X-ray diagnostic apparatus, X-ray computed tomography (CT) apparatus, magnetic resonance imaging (MRI) apparatus); an image generated by processing an actual image (image acquired from a living body); and a pseudo image.

Further, the number of images included in training data may be increased by using any technique such as data augmentation.

The method and technique of training (method and technique of machine learning) employed for constructing the inference model 1042 may be freely selected from among any known method and technique, or may be freely designed based on any known method and technique. In some examples, the method and technique of the training may be any of supervised learning, unsupervised learning, and reinforcement learning. In some alternative examples, the method and technique of the training may be any combination of any two or more of supervised learning, unsupervised learning, and reinforcement learning.

In some aspect examples, supervised learning is conducted on the basis of training data in which a label as a final output is assigned to each input image. For example, to each set of Scheimpflug images contained in the training data (e.g., for each set of two or more Scheimpflug images respectively representing two or more different locations (sites, places, parts, positions, cross sections) of the same eye), a pre-acquired interpolated image may be assigned in advance as a label. Labels may be generated by, for example, any one or more of a doctor, a computer, and other inference models. The learning processor 1061 may be configured to construct the inference model 1042 by applying supervised learning using such training data to the neural network 1062.

The inference model 1042 of the present example constructed in this way is a trained model (learned model) configured to receive an input of two or more Scheimpflug images respectively representing two or more different locations (sites, places, parts, positions, cross sections) of the same eye, and to generate an output of a spatially interpolated image of these two or more Scheimpflug images.

In order to prevent the overconcentration of processes in a specific unit of the neural network 1062, the learning processor 1061 may randomly select and invalidate one or more units and execute learning using the remaining units. Such a function is referred to as dropout.

The methods or techniques used for inference model creation are not limited to the examples shown above. In some examples, any methods or techniques such as the followings may be employed for creating an inference model: support vector machine, Bayes classifier, boosting, k-means clustering, kernel density estimation, principal component analysis, independent component analysis, self-organizing map (or self-organizing feature map), random forest (or randomized trees, random decision forests), and generative adversarial network (GAN).

Using the inference model 1042 as described above, the inferring unit 1041 shown in FIG. 6A performs spatial image interpolation of a series of Scheimpflug images collected by slit scanning from a three dimensional region of the subject's eye, or, spatial image interpolation of a series of Scheimpflug images reconstructed by the image selecting unit 1050. More specifically, first, the inferring unit 1041 inputs a series of Scheimpflug images to the inference model 1042. In response to this input, the inference model 1042 outputs an interpolated image (spatially interpolated image) on the basis of the series of Scheimpflug images inputted.

Figure 7:
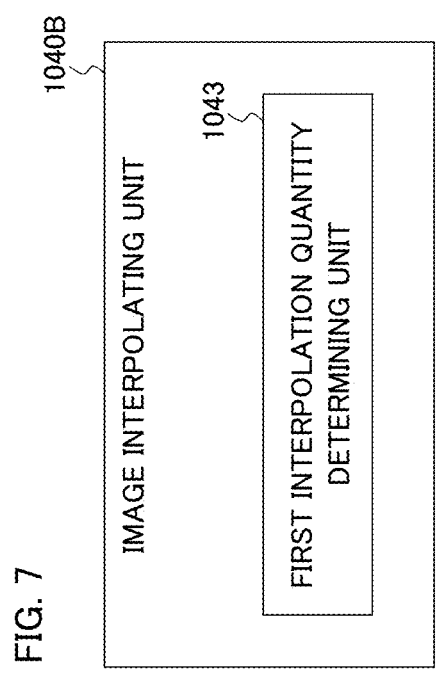
FIG. 7 is a diagram of a configuration of an ophthalmic imaging apparatus according to an aspect example.

In some aspect examples, the image interpolating unit 1040 may be configured to use the time series shifts of the slit light acquired by the first image analyzing unit 1030 in order to determine the number of images to be interpolated into a series of Scheimpflug images inputted, that is, in order to determine an interpolation quantity for a series of Scheimpflug images inputted. FIG. 7 shows an example of the image interpolating unit 1040 of the present embodiment example. The image interpolating unit 1040B of the present example includes the first interpolation quantity determining unit 1043.

The first interpolation quantity determining unit 1043 is configured to determine an interpolation quantity based on any one or both of operation information of the first image collecting unit 1010 and the time series shifts of the slit light acquired by the first image analyzing unit 1030. The interpolation quantity is the number (of pieces) of images added or interpolated, by spatial image interpolation, to or into a series of Scheimpflug images collected by the first image collecting unit 1010, or, to or into a series of Scheimpflug images reconstructed by the image selecting unit 1050. The image interpolating unit 1040B is configured to perform interpolation of the series of Scheimpflug images by introducing (adding, inserting, interposing) images of the interpolation quantity (that is, images of the number of pieces shown by the interpolation quantity) determined by the first interpolation quantity determining unit 1043.

The operation information of the first image collecting unit 1010, which can be used for interpolation quantity determination, may include a scanning condition of the slit scanning performed for the collection of the series of Scheimpflug images. The scanning condition may include any kinds of conditions of slit scanning such as a scan length (moving distance of the projection position of the slit light), a scan speed (moving speed of the projection position of the slit light), a scan rate (acquisition rate of the photography system, repetition frequency of photography, frame rate, image collection rate), or other conditions.

In aspect examples in which interpolation quantity determination is conducted on the basis of the operation information of the first image collecting unit 1010, the first interpolation quantity determining unit 1043 may be configured to be capable of calculating the distance (interval between images, image interval, image spacing) between two Scheimpflug images adjacent to each other, based on the operation information as described above.

While image intervals may be considered to be equal in a series of Scheimpflug images in some aspect examples, image intervals may be considered to be unequal in general cases. For example, the moving speed of the projection position of slit light is relatively low in a section immediately after the start position of the slit scanning (acceleration section), a section immediately before the end position of the slit scanning (deceleration section), and a section near the turnaround position of round-trip slit scanning (deceleration section and acceleration section), while the moving speed of the projection position of the slit light is relatively high in a section near the center position of the scanning area. Thus, the image intervals become unequal.

The first interpolation quantity determining unit 1043 determines each image interval in a series of Scheimpflug images by referring to the operation information and compares each image interval with a predetermined value (a predetermined image interval) set as a requirement for three dimensional image construction. By executing these processes, the first interpolation quantity determining unit 1043 determines an interpolation quantity for this series of Scheimpflug images.

In aspect examples in which interpolation quantity determination is conducted on the basis of the time series shifts of the slit light acquired by the first image analyzing unit 1030, the first interpolation quantity determining unit 1043 may be configured to be capable of determining an interpolation quantity in the same manner as the interpolation quantity determination of the basis of the operation information of the first image collecting unit 1010, based on an actual time series shifts (actually detected time series shifts, actually measured time series shifts) of the slit light during the slit scanning. Here, the actual time series shifts of the slit light during the slit scanning may be, for example, a moving distance of the projection position of the slit light, a projection position of the slit light at each time point, a moving speed of the projection position of the slit light at each time point, and a moving acceleration of the projection position of the slit light at each time point.

Figure 8:
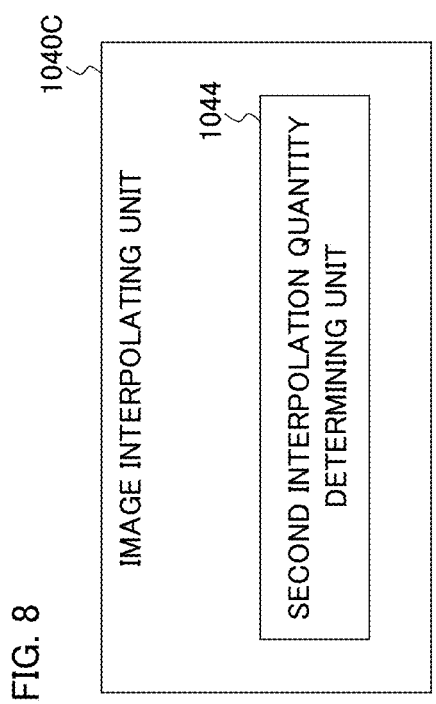
FIG. 8 is a diagram of a configuration of an ophthalmic imaging apparatus according to an aspect example.

In some aspect examples, the image interpolating unit 1040 may be configured to use the time series shifts of the subject's eye acquired by the first image analyzing unit 1030 to determine an interpolation quantity that is the number of images to be interpolated into a series of Scheimpflug images. FIG. 8 shows an example of the image interpolating unit 1040 of the present embodiment example. The image interpolating unit 1040C of the present example includes the second interpolation quantity determining unit 1044.

The second interpolation quantity determining unit 1044 is configured to determine an interpolation quantity, which is the number (of pieces) of images added or interpolated by spatial image interpolation to or into a series of Scheimpflug images collected by the first image collecting unit 1010 or a series of Scheimpflug images reconstructed by the image selecting unit 1050, based on any one or both of operation information of the first image collecting unit 1010 and the time series shifts of the subject's eye acquired by the first image analyzing unit 1030. The image interpolating unit 1040C is configured to perform interpolation of the series of Scheimpflug images by introducing (adding, inserting, interposing) images of the interpolation quantity (that is, images of the number of pieces shown by the interpolation quantity) determined by the second interpolation quantity determining unit 1044.

In aspect examples in which interpolation quantity determination is conducted on the basis of the operation information of the first image collecting unit 1010, the second interpolation quantity determining unit 1044 may executed the same or similar processing as or to the processing executed by the first interpolation quantity determining unit 1043 described above.

In aspect examples in which interpolation quantity determination is conducted on the basis of the time series shifts of the subject's eye acquired by the first image analyzing unit 1030, the influence of eye movement (e.g., fixation error, fixation deviation) of the subject's eye on the slit scanning can be compensated for (cancelled, eliminated). In the present aspect example, the second interpolation quantity determining unit 1044 may be configured to be capable of extracting time series shifts in the X direction from the time series shifts of the subject's eye, and correcting the positions of individual Scheimpflug images in the X direction in such a manner that the shifts of the subject's eye in the X direction at the time points corresponding to individual Scheimpflug images are compensated for. This yields a series of Scheimpflug images in which eliminated are the influence of the image position shifts in the x direction caused by the movement of the subject's eye during the period of time in which the slit scanning is being performed. The second interpolation quantity determining unit 1044 may be configured to compare each image interval of the series of Scheimpflug images rearranged in this way with a predetermined value (a predetermined image interval) set as a requirement for three dimensional image construction. By performing this comparison, the second interpolation quantity determining unit 1044 determines an interpolation quantity for this series of Scheimpflug images.

Further, the second interpolation quantity determining unit 1044 may be configured to be capable of extracting time series shifts in the Y direction from the time series shifts of the subject's eye, and correcting the positions of individual Scheimpflug image in the Y direction on the basis of the shifts of the subject's eye in the Y direction at the time points corresponding to individual Scheimpflug images. As a result, a series of Scheimpflug images adjusted to the image position shifts in the Y direction caused by the movement of the subject's eye during the period of time in which the slit scanning is being performed can be obtained. If there is a positional shift in the Y direction between two adjacent Scheimpflug images, the image interpolating unit 1040C may introduce an image that interpolates these two Scheimpflug images on the basis of the gradient (inclination, tilt, slope, slant) in the Y direction corresponding to the positional shift in the Y direction between these two adjacent Scheimpflug images. The same may be applied in the case in which time series shifts in the Z direction are detected.

Figure 9:
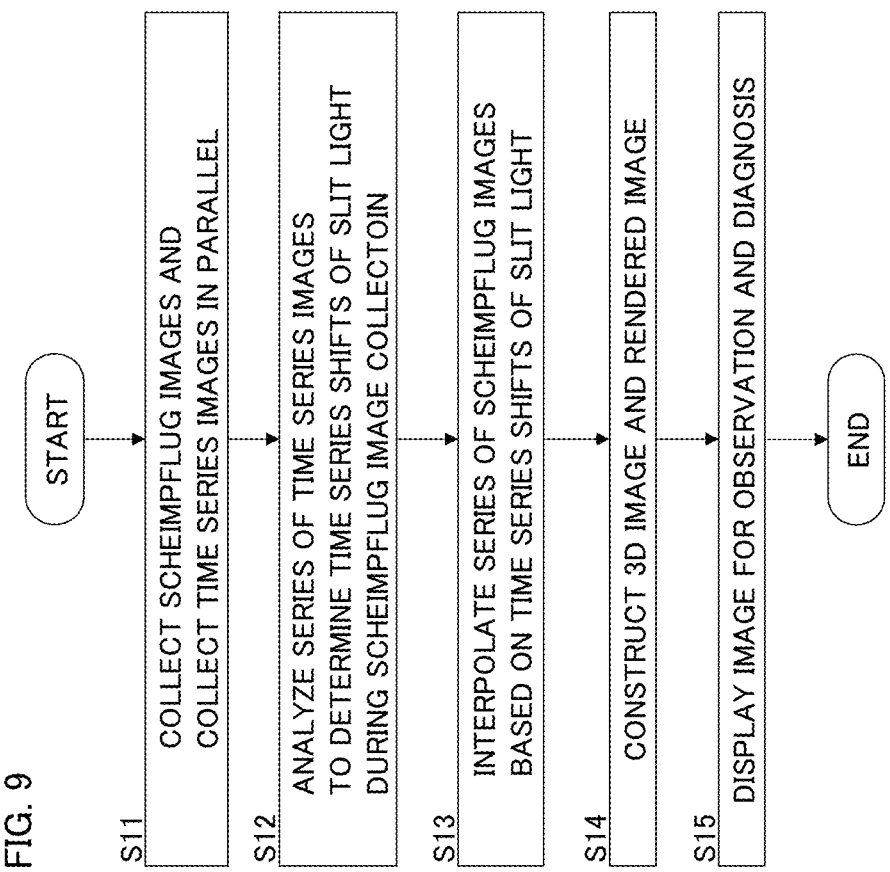
FIG. 9 is a flowchart illustrating a usage mode of an ophthalmic imaging apparatus according to an aspect example.

A usage mode of the ophthalmic imaging apparatus 1000 of the first aspect example will now be described with reference to FIG. 9. The usage mode described below is merely an example. For example, any matters and items described in the outline of the embodiment example as described above, any matters and items described in the first aspect example, and any other matters and items can be combined with or incorporated in the following usage mode.

Various kinds of operations required before performing photography with the ophthalmic imaging apparatus 1000 (preparatory operations) have been completed. The preparatory operations include the followings: adjustment of a table on which the ophthalmic imaging apparatus 1000 is placed; adjustment of a chair on which the subject sits; adjustment of a face support (e.g., chin rest, forehead rest) of the ophthalmic imaging apparatus 1000; alignment of the ophthalmic imaging apparatus 1000 relative to the subject's eye; and adjustment of the light amount (light intensity) of slit light.

In response to the instruction of commencement of photography, the ophthalmic imaging apparatus 1000 performs collection of a series of Scheimpflug images by the first image collecting unit 1010 and collection of a series of time series images by the second image collecting unit 1020 in parallel with each other (S11).

In some examples, the series of Scheimpflug images collected by the first image collecting unit 1010 and the series of time series images collected by the second image collecting unit 1020 are stored in a storage device (not shown in the drawings) provided in the ophthalmic imaging apparatus 1000 and/or in a storage device (not shown in the drawings) connected to the ophthalmic imaging apparatus 1000.

Next, the ophthalmic imaging apparatus 1000 analyzes the series of time series images collected by the second image collecting unit 1020 in the step S11 by the first image analyzing unit 1030, thereby obtaining time series shifts of the slit light during at least part of the period of time in which the series of Scheimpflug images are collected by the first image collecting unit 1010 in the step S11 (S12).

The information on the time series shifts of the slit light acquired by the first image analyzing unit 1030 is stored, for example, in the storage device of the ophthalmic imaging apparatus 1000 and/or in the storage device connected to the ophthalmic imaging apparatus 1000.

Next, the ophthalmic imaging apparatus 1000 performs interpolation of the series of Scheimpflug images collected in the step S11 based on the information on the time series shifts of the slit light acquired in the step S12, by the image interpolating unit 1040 (S13).

An image group created by the image interpolating unit 1040 and added to the series of Scheimpflug images is saved together with the series of Scheimpflug images, for example. This image group is referred to as a supplementary image group, an additional image group, or the like.

In some aspect examples, the image interpolating unit 1040 may be configured to be capable of determining an interpolation quantity based on any one or two or more of the following kinds of information: the operation information of the first image collecting unit 1010 in the step S11, the information on the time series shifts of the slit light obtained in the step 12; and the information on the time series shifts of the subject's eye generated from the series of time series images collected in the step S11.

In some aspect examples in which the first image collecting unit 1010 includes the first photography system 1011 and the second photography system 1012, the ophthalmic imaging apparatus 1000 may be configured to be capable of performing the following two processes. In the first process, the ophthalmic imaging apparatus 1000 constructs, by the image selecting unit 1050, another series of Scheimpflug images (a new series of Scheimpflug images) from the first scheimpflug image group collected by the first photography system 1011 and the second Scheimpflug image group collected by the second photography system 1012. Here, the another series of Scheimpflug images constructed may be, for example, a plurality of Scheimpflug images free of corneal reflection artifacts (a plurality of Scheimpflug images containing no corneal reflection artifacts). In the second process, the ophthalmic imaging apparatus 1000 performs interpolation of the another series of Scheimpflug images by the image interpolating unit 1040. The another series of Scheimpflug images and an image group added to the another series of Scheimpflug images (supplementary image group) are stored, for example, in the storage device of the ophthalmic imaging apparatus 1000 and/or in the storage device connected to the ophthalmic imaging apparatus 1000.

Next, the ophthalmic imaging apparatus 1000 or an image processing apparatus (not shown in the drawings) constructs a three dimensional image (three dimensional volume) based on a plurality of images including the series of Scheimpflug images and the supplementary image group, and further constructs a rendered image based on this three dimensional image (S14).

The three dimensional image and/or the rendered image are/is stored, for example, in the storage device of the ophthalmic imaging apparatus 1000 and/or in the storage device connected to the ophthalmic imaging apparatus 1000.

Next, the ophthalmic imaging apparatus 1000 or a computer (not shown in the drawings) reads out the data stored in the storage device of the ophthalmic imaging apparatus 1000 and/or in the storage device connected to the ophthalmic imaging apparatus 1000, and displays various kinds of images on a display device (not shown in the drawings) for the use of medical observation and medical diagnosis of the subject's eye (S15).

The various kinds of images displayed include, for example, the rendered image constructed in the step S14. The user can issue an instruction for applying a desired rendering to the three dimensional image constructed in the step S14.

The ophthalmic imaging apparatus 1000 may be configured to be capable of displaying the series of Scheimpflug images in a selective manner, or displaying a list of the series of Scheimpflug images. Similarly, the ophthalmic imaging apparatus 1000 may be configured to be capable of displaying the supplementary image group in a selective manner, or displaying a list of the supplementary image group. Here, the mode of displaying a Scheimpflug image and the mode of displaying a supplementary image may be different from each other. For example, in the case in which a supplementary image is displayed, the ophthalmic imaging apparatus 1000 may display supplementary information noting that this supplementary image is an image interpolated, that is, noting that this supplementary image is created by a computer (in other words, this supplementary image is not an image obtained by actually performing photography of the subject's eye). Likewise, in the case in which a Scheimpflug image is displayed, the ophthalmic imaging apparatus 1000 may display supplementary information noting that this Scheimpflug image is obtained by actually performing photography of the subject's eye. Employing any configuration of the present examples allows the user to be easily informed of whether each displayed image is a Scheimpflug image or a supplementary image.

According to the first aspect example that is capable of implementing such a usage mode, interpolation of a series of Scheimpflug images collected from a three dimensional region of the subject's eye can be performed with a supplementary image group. Therefore, three dimensional image construction can be executed without narrowing the intervals between the series of Scheimpflug images collected from the three dimensional region of the subject's eye. With this, it becomes possible to obtain a three dimensional image and a rendered image with an aspect ratio corresponding to the actual morphology of the three dimensional region of the subject's eye to which slit scanning is applied. This makes it possible to perform medical observation of the subject's eye more easily and more accurately as compared to conventional or existing methods, and therefore it is expected that the accuracy and precision of medical diagnosis can be improved. Further, by performing image analysis using a three dimensional image or a rendered image obtained by the technique of the first aspect example, it is expected that an analysis result of higher quality can be obtained as compared to conventional or existing methods. In addition to these advantageous effects, the first aspect example can also achieve various kinds of advantageous effects described in the present disclosure. Those skilled in the art would also be able to understand advantageous effects not explicitly stated in the present disclosure on the basis of the contents of the present disclosure.

Non-Limiting Second Aspect Example

The second aspect example provides an aspect example of an ophthalmic imaging apparatus configured to be capable of performing ocular tissue identifier assignment. Several specific examples (embodiment examples) of the ophthalmic imaging apparatus according to the present aspect example will be described later. Note that detailed descriptions of matters and items in the present section that are the same as or similar to those described in the section of the outline of several embodiment examples are sometimes omitted, and detailed descriptions of matters and items in the present section that are the same as or similar to those described in the section of the non-limiting first aspect example are also sometimes omitted.

Figure 10:
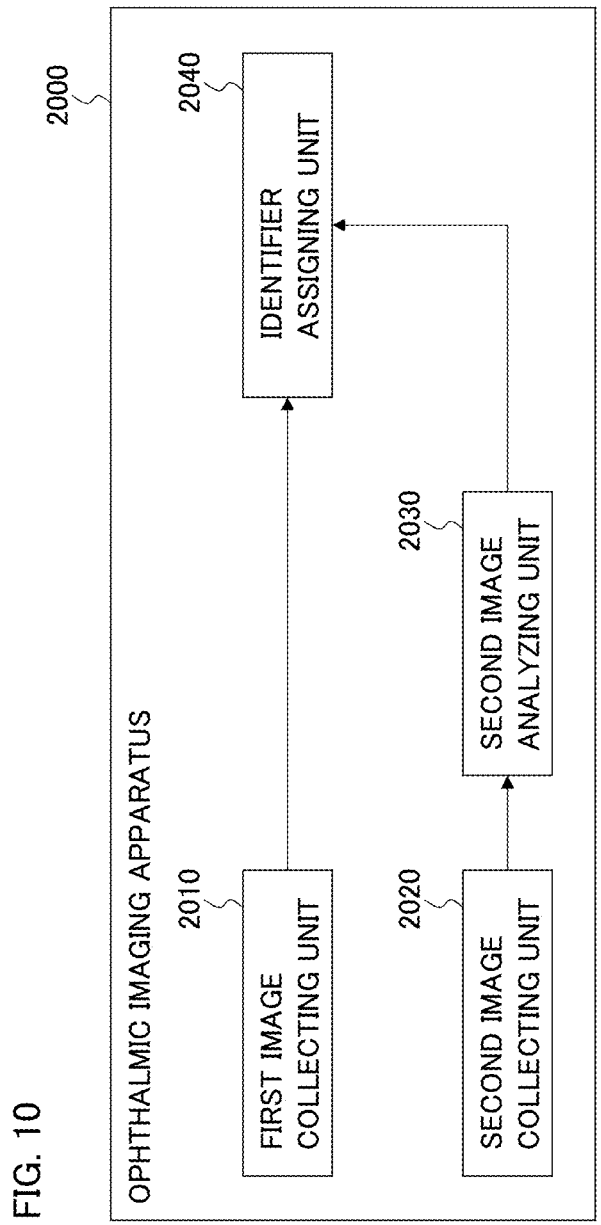
FIG. 10 is a diagram of a configuration of an ophthalmic imaging apparatus according to an aspect example.

FIG. 10 shows the configuration of the ophthalmic imaging apparatus according to the present aspect example. The ophthalmic imaging apparatus 2000 includes the first image collecting unit 2010, the second image collecting unit 2020, the second image analyzing unit 2030, and the identifier assigning unit 2040.

Information obtained through the process of ocular tissue identifier assignment performed by the identifier assigning unit 2040 may be utilized in various kinds of post-processing such as construction of a three dimensional image, construction of a rendered image, image analysis, and diagnostic imaging. Here, the information obtained through the process performed by the identifier assigning unit 2040 includes a plurality of Scheimpflug images, each of which is assigned with an ocular tissue identifier. The elements for performing such post-processing (e.g., processor, user interface) may be provided in the ophthalmic imaging apparatus 2000 or may be provided in an apparatus different from the ophthalmic imaging apparatus 2000.

The first image collecting unit 2010 may have the same or similar function and configuration as or to the first image collecting unit 1010 of the first aspect example, and the second image collecting unit 2020 may also have the same or similar function and configuration as or to the second image collecting unit 1020 of the first aspect.

The second image analyzing unit 2030 is configured to analyze a series of time series images collected by the second image collecting unit 2020 to detect a series of images of slit light (a series of slit light images). The process of detecting a slit light image from a time series image may be executed in the same manner as in the first aspect example (the first image analyzing unit 1030).

The identifier assigning unit 2040 is configured to perform assignment of an identifier to each Scheimpflug image in the series of Scheimpflug images collected by the first image collecting unit 2010, based on the series of slit light images detected from the series of time series images by the second image analyzing unit 2030. Here, each identifier represents an ocular tissue of the subject's eye onto which the slit light is being projected at the time point when a corresponding Scheimpflug image is acquired by the first image collecting unit 2010.

In the present aspect example, slit scanning is applied to a three dimensional region of the anterior segment of the subject's eye. Therefore, an ocular tissue represented by an identifier given to a Scheimpflug image may include a tissue or site of the anterior eye segment and may further include a tissue or site located in the vicinity of or close to the eyeball. Examples of this tissue or site of the anterior eye segment may include any tissue and/or any site such as the following, for example: the cornea; the corneal apex; the anterior surface of the cornea; the posterior surface of the cornea; the corneal ring (corneal limbus); the iris; the anterior surface of the iris; the posterior surface of the iris; the edge of the iris; the pupil; the edge of the pupil; the center of the pupil; the center of gravity of the pupil; the anterior chamber; the corner angle; the ciliary body; the zonule of Zinn; the crystalline lens; a nerve; a blood vessel; a lesion; a treatment scar; and an artificial object (e.g., an intraocular lens, an MIGS device) implanted in the anterior segment of the subject's eye. Further, examples of this tissue or site located in the vicinity of or close to the eyeball may include any tissue and/or any site such as the eyelid, the meibomian gland, eyelashes, and the lacrimal punctum.

In some aspect examples, the slit scanning of a three dimensional region of the subject's eye performed by the first image collecting unit 2010 and the repetitive photography of the subject's eye performed by the second image collecting unit 2020 may be performed in synchronization with each other. This synchronization provides a correspondence between a series of Scheimpflug images collected by the first image collecting unit 2010 and a series of time series images collected by the second image collecting unit 2020. The synchronization between the first image collecting unit 2010 and the second image collecting unit 2020 may be performed in the same manner as in the first aspect example. Further, the correspondence between the series of Scheimpflug images and the series of time series images may be the same as or similar to that of the first aspect example.

In some other aspect examples, post-processing can be executed to determine a correspondence between a series of Scheimpflug images collected by the first image collecting unit 2010 and a series of time series images collected by the second image collecting unit 2020. This post-processing may be performed in the same manner as in the first aspect example.

In some aspect examples in which the slit scanning performed by the first image collecting unit 2010 and the repetitive photography performed by the second image collecting unit 2020 are performed in a synchronized manner, the identifier assigning unit 2040 may be configured to perform the assignment of identifiers based further on a correspondence between a series of Scheimpflug images and a series of time series images determined on the basis of this synchronization between the scanning and the repetitive photography.

More specifically, the identifier assigning unit 2040 in such an aspect example may be configured to perform the assignment of identifiers, each of the identifiers represents an ocular tissue of the subject's eye onto which the slit light is being projected at the time point when a corresponding Scheimpflug image is acquired by the first image collecting unit 2010, to individual Scheimpflug images collected by the first image collecting unit 2010, based on a correspondence between the series of Scheimpflug images and the series of time series images determined based on the synchronization between the slit scanning performed by the first image collecting unit 2010 and the repetitive photography performed by the second image collecting unit 2020 as well as based on the series of slit light images detected from the series of time series images by the second image analyzing unit 2030. The same applies to an aspect example in which a similar correspondence is established by post-processing.

Such an aspect examples is capable of easily and accurately identifying a Scheimpflug image corresponding to each time series image by referring to the correspondence between the series of Scheimpflug images and the series of time series images. This makes it possible to assign an ocular tissue identifier determined from each time series image (from a slit light image depicted in each time series image) accurately to a Scheimpflug image corresponding to this time series image.

The identifier assigning unit 2040 of the aspect example as described above may be configured to execute the following two processes (the first process and the second process). In the first process, the identifier assigning unit 2040 performs, for each of the series of time series images, assignment of an ocular tissue identifier to a time series image based on a slit light image detected from this time series image.

For example, in order to carry out the first process, the identifier assigning unit 2040 may be configured to perform the following series of processes for each of the series of time series images: a process of identifying an image region (ocular tissue image region) corresponding to each of the various kinds of ocular tissues mentioned above by analyzing a time series image; a process of determining a positional relationship between a slit light image detected from this time series image and each ocular tissue image region identified (e.g., a relationship representing overlap between a slit light image and a ocular tissue image region, or a relationship representing intersection between a slit light image and a ocular tissue image region); a process of identifying an ocular tissue onto which the slit light is being projected at the time point when this time series image is acquired by the second image collecting unit 2020, based on the positional relationship determined for an slit light image obtained for each ocular tissue image region; and a process of performing assignment of an identifier representing the identified ocular tissue, to this time series image.

In some examples, in the case in which an image region corresponding to the cornea at least in part overlaps a slit light image, an identifier representing the cornea is assigned to this time series image. The number of ocular tissue identifiers assigned to one time series image may be freely determined and may be one or two or more. In addition, in the case in which no ocular tissue is identified onto which the slit light is being projected at the time point when a time series image is acquired by the second image collecting unit 2020, information representing the result that no ocular tissue is identified may be assigned to this time series image, or error information may be assigned to this time series image.

In the second process, the identifier assigning unit 2040 performs assignment of an ocular tissue identifier to each of the series of Scheimpflug images, based on the series of ocular tissue identifiers assigned to individual time series images in the series of time series images by the first process and based also on a correspondence between the series of Scheimpflug images and the series of time series images.

For example, in order to carry out the second process, the identifier assigning unit 2040 may be configured to perform the following processes for each of the series of time series images: a process to identify a Scheimpflug image corresponding to this time series image based on the above-mentioned correspondence; and a process of assigning an ocular tissue identifier assigned to this time series image in the first process, to the Scheimpflug image identified.

With the first and second processes described above, the identifier assigning unit 2040 is capable of easily and accurately assigning, to each of the series of Scheimpflug images, an identifier that represents an ocular tissue of the subject's eye onto which the slit light is being projected at the time point when that Scheimpflug image is acquired by the first image collecting unit 2010.

Furthermore, a group of Scheimpflug images corresponding to a certain ocular tissue can be selected from the series of Scheimpflug images collected by the first image collecting unit 2010.

In addition, from the series of Scheimpflug images collected by the first image collecting unit 2010, the first group corresponding to the first ocular tissue, the second group corresponding to the second ocular tissue, . . . , the P-th group corresponding to the P-th ocular tissue can be obtained. Here, P is an integer equal to or greater than 2. Note that the $p_1$-th group and the $p_2$-th group may overlap at least in part. Here, $p_1$ and $p_2$ are both integers equal to or greater than 1 and equal to or less than P, and $p_1$ and $p_2$ are different integers from each other.

In addition to the assignment of ocular tissue identifiers to Scheimpflug images based on time series images, some aspect examples may be configured to perform assignment of an ocular tissue identifier(s) to a Scheimpflug image on the basis of a Scheimpflug image(s) and/or assignment of an ocular tissue identifier(s) to a time series images on the basis of a Scheimpflug image(s). These aspect examples make it possible to identify an ocular tissue that is difficult or impossible to detect from a time series image(s) (e.g., a front image) and assign an identifier to the ocular tissue identified. For example, the corneal apex, a tissue in the eyeball or an intraocular tissues (e.g., the crystalline lens, the corner angle), a lesion in the eyeball, and an artificial object implanted in the eyeball are difficult or impossible to be detected from a front image of the subject's eye. However, the present aspect example is capable of detecting these ocular tissues and assign identifiers to them.

Next, an aspect example configured to perform the assignment of an ocular tissue identifier to a Scheimpflug image on the basis of a Scheimpflug image will be described. The second image analyzing unit 2030 of the present aspect example may be configured to analyze a series of Scheimpflug images collected by the first image collecting unit 2010 to detect a series of images of the slit light (a series of slit light images). The second image analyzing unit 2030 analyzes each Scheimpflug image to detect a slit light image depicted in the Scheimpflug image. This processing may be executed in the same manner as the processing of detecting a slit light image from a time series image.

Further, the identifier assigning unit 2040 of the present aspect example may be configured to perform the assignment of ocular tissue identifiers based on the series of slit light images detected from the series of Scheimpflug images collected by the first image collecting unit 2010. For each Scheimpflug image of the series of Scheimpflug images, the identifier assigning unit 2040 assigns an ocular tissue identifier to a Scheimpflug image based on a slit light image detected from this Scheimpflug image. The assignment of an ocular tissue identifier to a Scheimpflug image based on an slit light image in this Scheimpflug image may be performed in the same manner as in the assignment of an ocular tissue identifier to a time series image based on a slit light image in this time series image (described above).

Next, an aspect example configured to perform the assignment of an ocular tissue identifier to a time series image based on a Scheimpflug image will be described. The second image analyzing unit 2030 of the present aspect example may be configured to analyze the series of Scheimpflug images collected by the first image collecting unit 2010 to detect an image of a site of interest of the subject's eye. The site of interest may be any predetermined sites such as the corneal apex, a tissue in the eyeball or an intraocular tissue, a lesion in the eyeball, and an artificial object implanted in the eyeball. The processing of detecting an image of a site of interest from a Scheimpflug image may be executed in the same manner as the processing of detecting an image of an ocular tissue from a time series image.

Further, the identifier assigning unit 2040 of the present aspect may be configured to perform the assignment of an identifier representing the site of interest to one or more of the series of time series images collected by the second image collecting unit 2020, based on the image of the site of interest detected from the series of Scheimpflug images collected by the first image collecting unit 2010. In order to give information obtained from a Scheimpflug image to a time series image, the identifier assigning unit 2040 may refer to a correspondence between the series of Scheimpflug images and the series of time series images obtained by using the above-mentioned synchronization or the above-mentioned post-processing.

The assignment of an ocular tissue identifier to a Scheimpflug image may be any of the followings: assignment of an ocular tissue identifier to a Scheimpflug image itself; assignment of an ocular tissue identifier to a series of Scheimpflug images; assignment of an ocular tissue identifier to an image group selected from a series of Scheimpflug images; and assignment of an ocular tissue identifier to a partial region of a Scheimpflug image. Similarly, the assignment of an ocular tissue identifier to a time series image may be any the followings: assignment of an ocular tissue identifier to a time series image itself; assignment of an ocular tissue identifier to a series of time series images; assignment of an ocular tissue identifier to an image group selected from a series of time series images; and assignment of an ocular tissue identifier to a partial region of a time series image.

In some aspect examples, the identifier assigning unit 2040 may be configured to perform, for each of the series of Scheimpflug images, the assignment of an identifier corresponding to an ocular tissue to a partial region of a Scheimpflug image corresponding to this ocular tissue onto which the slit light is being projected at the time point when this corresponding Scheimpflug image is acquired by the first image collecting unit 1010.

In some examples, in the case in which the cornea is an ocular tissue onto which the slit light is being projected at the time point when a Scheimpflug image is acquired, the identifier assigning unit 2040 may assign an identifier representing the cornea to a partial image corresponding to the cornea (cornea region) in this Scheimpflug image.

In some other examples, in the case in which the cornea and corner angle are ocular tissues onto which the slit light is being projected at the time point when a Scheimpflug image is acquired, the identifier assigning unit 2040 may perform both assignment of an identifier representing the cornea to a cornea region in this Scheimpflug image and assignment of an identifier representing the corner angle to a corner angle region in this Scheimpflug image.

According to such an aspect example, it becomes possible for the user to easily perceive not only which part of a Scheimpflug image the slit light is being projected onto, but also the type, area, shape, etc. of an ocular tissue(s) onto which the slit light is being projected. Likewise, it becomes possible for the user to easily perceive not only which part of a time series image the slit light is being projected onto, but also the type, area, shape, etc. of an ocular tissue(s) onto which the slit light is being projected.

Any matters and items described in the first aspect example may be combined with or incorporated in the second aspect example. Several examples of such combination or incorporation will be described below. Note that aspects of the combination or incorporation between the first aspect example and the second aspect example are not limited to these examples, and any matters and items of the first aspect example and any matters and items of the second aspect example may be combined or incorporated at least in part.

In some aspect examples, the first image collecting unit 2010 may include the first photography system and the second photography system that are configured to perform photography of the subject's eye in the slit scanning from mutually different directions The first photography system is configured to collect the first Scheimpflug image group, and the second photography system is configured to collect the second Scheimpflug image group. The series of Scheimpflug images collected by the first image collecting unit 2010 of the present aspect example includes the first Scheimpflug image group and the second Scheimpflug image group. The illustration of the first photography system and the second photography system according to the present aspect example is omitted. However, those skilled in the art would understand, from the corresponding sections of descriptions of the first aspect example, FIG. 4, FIG. 5, and other parts of the present disclosure, the arrangement, function, and configuration of the first photography system and the second photography system in the present aspect example.

Furthermore, in some aspect examples, photography performed by the first photography system and photography performed by the second photography system may be performed in synchronization with each other.

In addition, some aspect examples may include an image selecting unit that have the same or similar arrangement, function, and configuration as or to those of the image selecting unit 1050 of the first aspect example. The image selecting unit of the present aspect example is configured to perform selection of another series of Scheimpflug images corresponding to the slit scanning performed by the first image collecting unit 2010 from the first Scheimpflug image group and the second Scheimpflug image group, based on a correspondence between the first Scheimpflug image group and the second Scheimpflug image group determined based on the synchronization between the photography performed by the first photography system and the photography performed by the second photography system. The illustration of the image selection unit according to the present aspect example is omitted. However, those skilled in the art would understand, from the corresponding sections of descriptions of the first aspect example, FIG. 4, FIG. 5, and other parts of the present disclosure, the arrangement, function, and configuration of the image selection unit in the present aspect example.

The identifier assigning unit 2040 of the present aspect example may be configured to perform assignment of the ocular tissue identifier to each Scheimpflug image included in the another series of Scheimpflug images constructed by the image selection unit. The assignment of the ocular tissue identifier to each of the Scheimpflug images selected from the first Scheimpflug image group and the second Scheimpflug image group by the image selection unit, may be performed in the same manner as the assignment of the ocular tissue identifier to the series of Scheimpflug images collected by the first image collecting unit 2010.

In some aspect examples, the first image collecting unit 2010 may further include an illumination system configured to project the slit light onto a three dimensional region of the subject's eye. Further, the optical axis of the first photography system and the optical axis of the second photography system may be arranged in an oblique manner in mutually opposite directions relative to the optical axis of the illumination system. In addition, the image selecting unit may be further configured to perform selection of the another series of Scheimpflug images by selecting a plurality of Scheimpflug images containing no corneal reflection artifact from the first Scheimpflug image group and the second Scheimpflug image group, based on the correspondence between the first Scheimpflug image group and the second Scheimpflug image group. It should be noted that although the illustration of the illumination system according to the present aspect example is omitted, those skilled in the art would understand, from the corresponding sections of descriptions of the first aspect example, FIG. 5, and other parts in the present disclosure, the arrangement, function, and configuration of the illumination system in the present aspect example.

In some aspect examples, the first image collecting unit 2010 may be configured to perform the slit scanning of a three dimensional region of the subject's eye by translating the slit light in a direction perpendicular to a longitudinal direction of the slit light. Here, the longitudinal direction of the slit light may substantially coincide with the body axis direction of the subject. Further, the size of the slit light in the longitudinal direction may be equal to or greater than a corneal diameter in the body axis direction of the subject, and a distance of translation of the slit light performed by the first image collecting unit 2010 may be equal to or greater than a corneal diameter in a direction perpendicular to the body axis direction of the subject.

Figure 11:
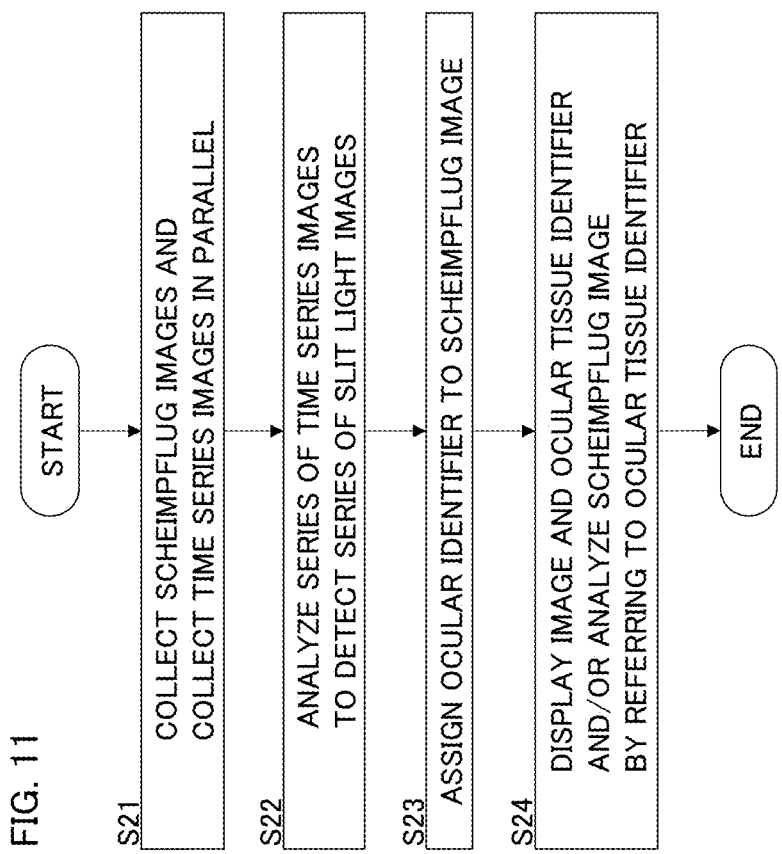
FIG. 11 is a flowchart illustrating a usage mode of an ophthalmic imaging apparatus according to an aspect example.

A usage mode of the ophthalmic imaging apparatus 2000 according to the second aspect example will be described with reference to FIG. 11. The usage mode described below is merely an example. For example, any matters and items described in the above-described outline of the embodiment example, any matters and items described in the first aspect example, or any matters and items described in the second aspect example may be combined with or incorporated in the following usage mode. Note that the preparatory operations have been completed.

In response to the instruction of commencement of photography, the ophthalmic imaging apparatus 2000 performs collection of a series of Scheimpflug images by the first image collecting unit 2010 and collection of a series of time series images by the second image collecting unit 2020 in parallel with each other (S21).

In some examples, the series of Scheimpflug images collected by the first image collecting unit 2010 and the series of time series images collected by the second image collecting unit 2020 are stored in a storage device (not shown in the drawings) provided in the ophthalmic imaging apparatus 2000 and/or in a storage device (not shown in the drawings) connected to the ophthalmic imaging apparatus 2000.

Next, the ophthalmic imaging apparatus 2000 analyzes the series of time series images collected by the second image collecting unit 2020 in the step S21 by the second image analyzing unit 2030, thereby detecting a series of slit light images (S22).

Next, the ophthalmic imaging apparatus 2000 performs, by the identifier assigning unit 2040, assignment of an identifier to each of the series of Scheimpflug images collected in the step S21 based on the series of slit light images detected in the step S22 (S23). Here, an identifier assigned to a Scheimpflug image represents an ocular tissue onto which the slit light is being projected at the time point when this Scheimpflug image is acquired by the first image collecting unit 2010 in the step S21.

Each of the ocular tissue identifiers assigned to respective Scheimpflug images by the identifier assigning unit 2040 is stored in association with a corresponding Scheimpflug image. In some examples, the identifier assigning unit 2040 may be configured to embed an ocular tissue identifier in a corresponding Scheimpflug image as an image or a code. If this is the case, a Scheimpflug image with an ocular tissue identifier embedded is saved. In some other examples in which management of medical images is conducted using a system in conformity with the digital imaging and communications in medicine (DICOM) standard, the identifier assigning unit 2040 may be configured to record an ocular tissue identifier in tag information (DICOM tag) of a corresponding Scheimpflug image. If this is the case, a ocular tissue identifier is saved as a tag information attached to a corresponding Scheimpflug image.

In an aspect example in which the first image collecting unit 2010 includes the first photography system (1011) and the second photography system (1012), the ophthalmic imaging apparatus 2000 may be configured to construct another series of Scheimpflug images from the first Scheimpflug image group collected by the first photography system and the second Scheimpflug images collected by the second photography system by the image selection unit (1050). Here, this another series of Scheimpflug images may be, for example, a plurality of Scheimpflug images containing no corneal reflection artifact. In addition, the ophthalmic imaging apparatus 2000 of the present aspect example may be configured to perform assignment of an ocular tissue identifier to each of this another series of Scheimpflug images by the identifier assigning unit 2040.

In some examples, the another series of Scheimpflug images and the ocular tissue identifiers attached to the Scheimpflug images are stored in a storage device of the ophthalmic imaging apparatus 2000 and/or in a storage device connected to the ophthalmic imaging apparatus 2000.

Some aspect examples may be configured to perform the following series of processes: a process of assigning an ocular tissue identifier to each of the first Scheimpflug image group; a process of assigning an ocular tissue identifier to each of the second Scheimpflug image group; and a process of selecting another series of Scheimpflug images in which an ocular tissue identifier has been assigned to each Scheimpflug image, from a set of Scheimpflug images that includes both the first Scheimpflug image group in which an ocular tissue identifier has been assigned to each Scheimpflug image and the second Scheimpflug image group in which an ocular tissue identifier has been assigned to each Scheimpflug image. Therefore, in the second aspect example, the ocular tissue identifier assignment process may be performed after the image selection process, or the ocular tissue identifier assignment process may be performed before the image selection process. Note that at least part of the image selection process and at least part of the ocular tissue identifier assignment process may be performed in parallel with each other.

Next, the ophthalmic imaging apparatus 2000 or an image processing apparatus (not shown in the drawings) may read out the data stored in the storage device of the ophthalmic imaging apparatus 2000 and/or the storage device connected to the ophthalmic imaging apparatus 2000, and then display a Scheimpflug image together with an ocular tissue identifier on a display device and/or display a Scheimpflug image on the display device on the basis of an ocular tissue identifier (S24).

In some examples, the ophthalmic imaging apparatus 2000 or an image processing apparatus (not shown in the drawings) may display the name (e.g., a character string representing the name) of the ocular tissue represented by an ocular tissue identifier together with a Scheimpflug image. In some other examples, the ophthalmic imaging apparatus 2000 or an image processing apparatus (not shown in the drawings) may select a group of Scheimpflug images with identifiers of the same ocular tissue assigned, from the series of Scheimpflug images, and then display the selected Scheimpflug image group in a selective manner or as a list. In yet some other examples, the ophthalmic imaging apparatus 2000 or an image processing apparatus (not shown in the drawings) may select a group of Scheimpflug images with identifiers of the same ocular tissue assigned, from the series of Scheimpflug images, and then construct a three dimensional image from the Scheimpflug image group selected, and further display a rendered image of this three dimensional image.

In an aspect example in which an ocular tissue identifier is assigned to a partial region of a Scheimpflug image corresponding to an ocular tissue, the ophthalmic imaging apparatus 2000 or an image processing apparatus (not shown in the drawings) may display information indicating a region of an ocular tissue indicated by an ocular tissue identifier, together with a corresponding Scheimpflug image. This information is, for example, an image representing the outline (contour, boundary) of the region of the ocular tissue.

In an aspect example in which an ocular tissue identifier is not assigned to a partial region of a Scheimpflug image corresponding to an ocular tissue, the ophthalmic imaging apparatus 2000 or an image processing apparatus (not shown in the drawings) may execute analysis (segmentation) of a Scheimpflug image by referring to an ocular tissue indicated by an ocular tissue identifier to identify a partial region corresponding to this ocular tissue, and then display information representing the identified partial region together with the Scheimpflug image.

In addition to or in place of displaying a Scheimpflug image, the ophthalmic imaging apparatus 2000 or an image processing apparatus (not shown in the drawings) may execute analysis of a Scheimpflug image by referring to an ocular tissue identifier (S24).

In some examples, the ophthalmic imaging apparatus 2000 or an image processing apparatus (not shown in the drawings) may be configured to select a partial region in a Scheimpflug image based on an ocular tissue identifier and then apply image analysis to the partial region selected. This makes it possible to reduce the size of the region to which the image analysis is applied, which produces advantageous effects of shortening of processing time, reduction of processing resources, and the like. In an aspect example in which an ocular tissue identifier is assigned to a partial region of a Scheimpflug image corresponding to an ocular tissue, the same or similar processing can be easily performed.

In some other examples, the ophthalmic imaging apparatus 2000 or an image processing apparatus (not shown in the drawings) may be configured to select an image analysis program from a computer program library constructed in advance, based on an ocular tissue identifier, and then apply image analysis to a Scheimpflug image using the image analysis program selected. As a result of this, it becomes possible to improve the accuracy of the selection of a program suitable for analysis to be performed on a Scheimpflug image, from various kinds of image analysis programs. With this, the automation of the analysis of Scheimpflug images can be promoted.

According to the second aspect example configured to be capable of implementing the usage modes described above, to each Scheimpflug image acquired by the slit scanning, an identifier of an ocular tissue onto which the slit light is being projected at the time point when this Scheimpflug image is acquired can be assigned. Consequently, the user can easily and correctly perceive the type or kind of an ocular tissue(s) depicted in an image provided to a task such as medical observation or medical diagnosis, or provided to data processing such as data analysis. Furthermore, the second aspect example allow analysis of Scheimpflug images to be performed in a more preferable manner. In addition to these advantageous effects, the second aspect example also produces the various kinds of advantageous effects described in the present disclosure. Further, those skilled in the art would also be able to understand advantageous effects not explicitly stated in the present disclosure on the basis of the contents of the present disclosure.

Non-Limiting Third Aspect Example

Figure 12:
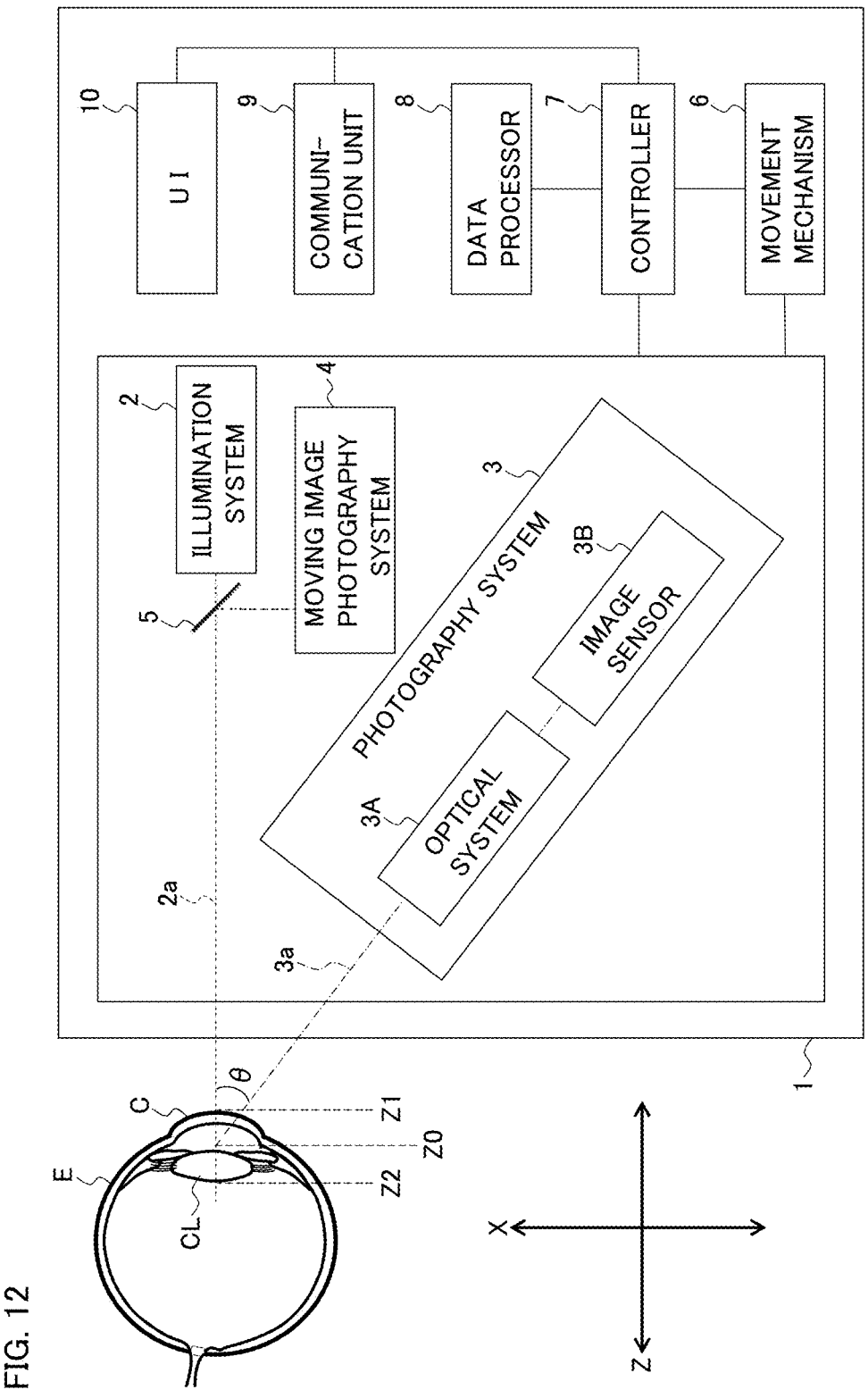
FIG. 12 is a diagram of a configuration of an ophthalmic imaging apparatus according to an aspect example.

The third aspect example provides an embodiment example including a combination of the first aspect example and the second aspect example. FIG. 12 shows an example of the ophthalmic imaging apparatus according to the third aspect example. The ophthalmic imaging apparatus of the present aspect example is a system (the slit lamp microscope system 1) configured as a combination of a slit lamp microscope and a computer (information processing apparatus).

The slit lamp microscope system 1 of the present aspect example is used for photography of the anterior segment of the subject's eye E. The slit lamp microscope system 1 of the present aspect example includes the illumination system 2, the photography system 3, the moving image photography system 4, the optical path coupling element 5, the movement mechanism 6, and the controller 7, the data processor 8, the communication unit 9, and the user interface 10. The reference character C denotes the cornea of the subject's eye E, and the reference character CL denotes the crystalline lens of the subject's eye E.

As a non-limiting example of the arrangement (disposition) of the group of elements of the slit lamp microscope system 1, the slit lamp microscope system 1 of some aspect examples includes a microscope main body, a computer, and a communication device. The communication device is configured to perform data communication between the microscope and the computer. The microscope main body includes the illumination system 2, the photography system 3, the moving image photography system 4, the optical path coupling element 5, and the movement mechanism 6. The computer includes the controller 7, the data processor 8, the communication unit 9, and the user interface 10. The computer may be placed in the vicinity of the microscope main body or may be disposed on a network, for example.

The combination of the illumination system 2, the photography system 3, and the movement mechanism 6 is an example of the first image collecting unit 1010 of the first aspect example and an example of the first image collecting unit 2010 of the second aspect example. The illumination system 2 is an example of the illumination system 1013 of the first aspect example. The moving image photography system 4 is an example of the second image collecting unit 1020 of the first aspect example and an example of the second image collecting unit 2020 of the second aspect example.

The illumination system 2 projects slit light onto the anterior segment of the subject's eye E. The reference character 2a denotes the optical axis of the illumination system 2 that is referred to as the illumination optical axis. The illumination system 2 may have the same or similar configuration as or to the illumination system of a conventional or existing slit lamp microscope. For example, the illumination system 2 includes an illumination light source, a positive lens, a slit forming member, and an objective lens in the order from the side far from the subject's eye E (not shown in the drawings). The illumination light output from the illumination light source passes through the positive lens and is projected onto the slit forming member. The slit forming member passes a part of the illumination light to generate slit light. The slit forming member has a pair of slit blades. The width of the slit light is changed by changing the interval between the slit blades. The interval between the slit blades is referred to as a slit width. Further, by rotating the pair of slit blades, the orientation of the longitudinal direction of the slit light may be changed. Furthermore, the slit forming member may change the size of the slit light in the longitudinal direction. The slit light generated by the slit forming member is refracted by the objective lens and is projected onto the anterior segment of the subject's eye E.

The illumination system 2 may include a focusing mechanism configured for changing the focal position of the slit light. The focusing mechanism of some examples may be configured to move the objective lens along the illumination optical axis 2a. Alternatively, the focusing mechanism of some other examples may be configured to move a focusing lens disposed between the objective lens and the slit forming member.

FIG. 12 is a top view, in which the direction along the axis of the subject's eye E is defined as the Z direction. Of the directions perpendicular to the Z direction, the left-right direction (the lateral direction) relative to the subject is defined as the X direction. Further, the direction perpendicular to both the X direction and the Z direction is defined as the Y direction (the vertical direction, the body axis direction). The slit lamp microscope system 1 according to the present aspect example may perform alignment relative to the subject's eye E in such a manner that the illumination optical axis 2a and the axis of the subject's eye E are brought to coincide with each other. In a broader sense, the alignment may be carried out in such a manner that the illumination optical axis 2a and the axis of the subject's eye E are brought to be disposed in parallel with each other.

The photography system 3 is configured to perform photography of the anterior segment while the slit light from the illumination system 2 is being projected onto the anterior segment. The reference character 3a denotes the optical axis of the photography system 3 that is referred to as the photography optical axis. The photography system 3 includes the optical system 3A and the image sensor 3B. The optical system 3A is configured to direct light coming from the anterior segment of the subject's eye E onto which the slit light is being projected, to the image sensor 3B. The optical system 3A may have, for example, the same or similar configuration as or to the photography system of a conventional or existing slit lamp microscope. For example, the optical system 3A includes an objective lens, a variable magnification optical system, and an imaging lens in the order from the side closer to the subject's eye E. The light coming from the anterior segment of the subject's eye E onto which the slit light is being projected, passes through the objective lens and the variable magnification optical system, and then forms an image on the light detecting plane of the image sensor 3B by the imaging lens. The image sensor 3B includes a light detecting plane that receives the light directed by the optical system 3A. The image sensor 3B includes an area sensor that has a two dimensional image detecting area. The area sensor may be, for example, a charge-coupled device (CCD) image sensor, a complementary metal oxide semiconductor (CMOS) image sensor, or another type of image sensor.

The photography system 3 may include a focusing mechanism configured for changing the focal position of the photography system 3. The focusing mechanism may be configured to move the objective lens along the photography optical axis 3a, for example. Alternatively, the focusing mechanism may be configured to move the focusing lens disposed between the objective lens and the imaging lens along the photography optical axis 3a.

The illumination system 2 and the photography system 3 function as a Scheimpflug camera. More specifically, the illumination system 2 and the photography system 3 are configured in such a manner that the subject plane along the illumination optical axis 2a, the optical system 3A, and the light detecting plane of the image sensor 3B satisfy what is commonly referred to as the Scheimpflug condition. More specifically, the YZ plane passing through the illumination optical axis 2a (the YZ plane contains the subject plane), the principal plane of the optical system 3A, and the light detecting plane of the image sensor 3B intersect on the same straight line. As a result of this, photographing can be performed with all positions in the subject plane in focus. In other words, photographing can be performed with all positions in the direction along the illumination optical axis 2a in focus.

The illumination system 2 and the photography system 3 of the present aspect example are configured in such a manner that at least an area from the anterior surface of the cornea C to the posterior surface of the crystalline lens CL is in focus of the photography system 3. In other words, the slit lamp microscope system 1 is capable of performing photography of the anterior segment of the subject's eye E in a state (in a condition) in which the focus of the photography system 3 is on the entire area from the apex of the anterior surface of the cornea C (Z=Z1) to the apex of the posterior surface of the crystalline lens CL (Z=Z2). Note that the intersection of the illumination optical axis 2a and the photography optical axis 3a is located at the coordinate Z=Z0. The condition described above is realized (achieved, satisfied, met) on the basis of the configuration and arrangement of the elements included in the illumination system 2, the configuration and arrangement of the elements included in the photography system 3, and the relative positions between the illumination system 2 and the photography system 3. A parameter indicating the relative positions of the illumination system 2 and the photography system 3 may include the angle $\theta$ formed by the illumination optical axis 2a and the photography optical axis 3a, for example. The value of the angle $\theta$ may be set to 17.5 degrees, 30 degrees, or 45 degrees, for example. The angle $\theta$ may be variable.

The moving image photography system 4 performs moving image photography of the anterior segment of the subject's eye E in parallel with the photography of the subject's eye performed by the illumination system 2 and the photography system 3. The moving image photography system 4 functions as a video camera.

The optical path coupling element 5 couples the optical path of the illumination system 2 and the optical path of the moving image photography system 4. The optical path of the illumination system is referred to as the illumination optical path and the optical path of the moving image photography system 4 is referred to as the moving image photography optical path. The optical path coupling element 5 may be a beam splitter such as a half mirror or a dichroic mirror, for example.

Figure 13:
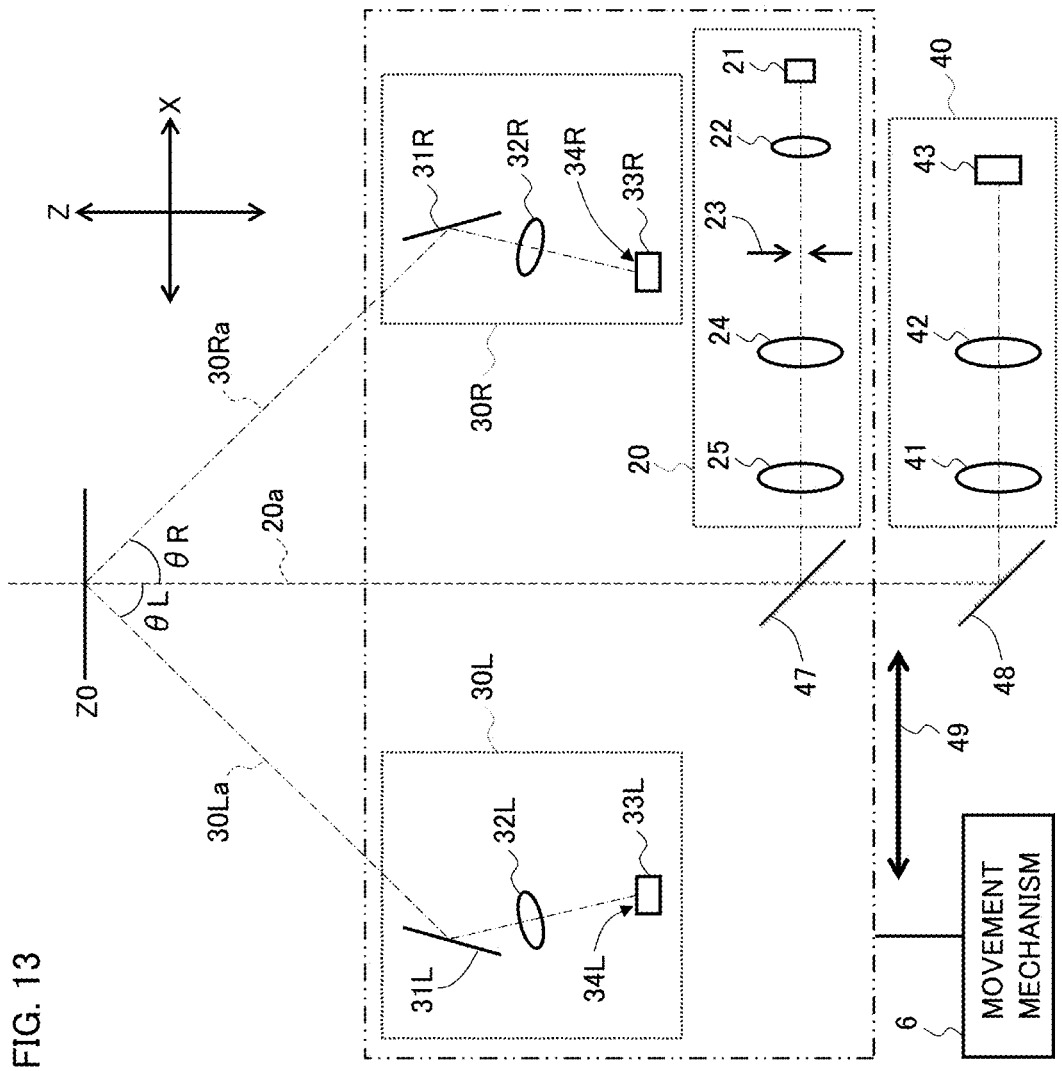
FIG. 13 is a diagram of a configuration of an ophthalmic imaging apparatus according to an aspect example.

FIG. 13 shows a specific example of an optical system including the illumination system 2, the photography system 3, the moving image photography system 4, and the optical path coupling element 5. In the present example, the photography system 3 includes two photography systems that function as the first photography system and the second photography system. In some aspect examples, the optical system of the slit lamp microscope system 1 may also include other elements in addition to the group of elements shown in FIG. 13, or in place of any of these elements. Here, the "other elements" may include, for example, any element in the first aspect example and/or any element in the second aspect example.

The optical system shown in FIG. 13 includes the illumination system 20, the left photography system 30L, the right photography system 30R, and the moving image photography system 40. The illumination system 20 is an example of the illumination system 2. The combination of the left photography system 30L and the right photography system 30R is an example of the photography system 3, and is also an example of the combination of the first photography system 1011 and the second photography system 1012 of the first aspect example. The moving image photography system 40 is an example of the moving image photography system 4. The beam splitter 47 is an example of the optical path coupling element 5.

In FIG. 13, the reference character 20a denotes the optical axis of the illumination system 20 (referred to as the illumination optical axis), the reference character 30La denotes the optical axis of the left photography system 30L (referred to as the left photography optical axis), and the reference character 30Ra denotes the optical axis of the right photography system 30R (referred to as the right photography optical axis). The orientation of the left photography optical axis 30La and the orientation of the right photography optical axis 30Ra are different from each other. The angle formed by the illumination optical axis 20a and the left photography optical axis 30La is denoted by $\theta L$, and the angle formed by the illumination optical axis 20a and the right photography optical axis 30Ra is denoted by $\theta R$. The angle $\theta L$ and the angle $\theta R$ may be equal to each other or may be different from each other. Each of the angle $\theta L$ and the angle $\theta R$ may be variable. The illumination optical axis 20a, the left photography optical axis 30La, and the right photography optical axis 30Ra intersect at one point. As with FIG. 12, the Z coordinate of the intersection is denoted by Z0.

The movement mechanism 6 of the present example is configured to move the illumination system 20, the left photography system 30L, and the right photography system 30R in the direction denoted by the arrow 49 (X direction). In some aspect examples, the illumination system 20, the left photography system 30L, and the right photography system 30R are mounted on a stage that is movable at least in the X direction, and the movement mechanism 6 moves the movable stage in the X direction under a control signal from the controller 7.

The illumination system 20 is configured to project slit light onto the anterior segment of the subject's eye E. Similar to the illumination system of a conventional or existing slit lamp microscope, the illumination system 20 includes the illumination light source 21, the positive lens 22, the slit forming member 23, and the group of objective lenses 24 and 25 in the order from the side far from the subject's eye E.

The illumination light output from the illumination light source 21 (e.g., visible light) is refracted by the positive lens 22 and projected onto the slit forming member 23. Part of the illumination light projected onto the slit forming member 23, passes through the slit formed by the slit forming member 23 and becomes slit light. The slit light generated by the slit forming member 23 is refracted by the group of objective lenses 24 and 25, and then reflected by the beam splitter 47, and projected onto the anterior segment of the subject's eye E.

The left photography system 30L includes the reflector 31L, the imaging lens 32L, and the image sensor 33L. The reflector 31L and the imaging lens 32L direct, to the image sensor 33L, light coming from the anterior segment onto which the slit light is being projected by the illumination system 20 (i.e., light coming from the anterior segment and traveling in the direction of the left photography system 30L).

The light traveling in the direction of the left photography system 30L from the anterior segment corresponds to light that comes from the anterior segment onto which the slit light is being projected and that travels in the direction away from the illumination optical axis 20a. The reflector 31L is arranged to reflect the light toward a direction approaching the illumination optical axis 20a. The imaging lens 32L refracts the light reflected by the reflector 31L and forms an image on the light detecting plane 34L of the image sensor 33L. The image sensor 33L receives and detects the light by the light detecting plane 34L.

The left photography system 30L performs repetitive photography in parallel with movement of the illumination system 20, the left photography system 30L, and the right photography system 30R performed by the movement mechanism 6. This acquires a plurality of anterior segment images (i.e., a series of Scheimpflug images).

The subject plane along the illumination optical axis 20a, the optical system that includes the reflector 31L and the imaging lens 32L, and the light detecting plane 34L satisfy the Scheimpflug condition. More specifically, considering the deflection of the optical path of the photography system 30L by the reflector 31L, the YZ plane (including the subject plane) passing through the illumination optical axis 20a, the principal plane of the imaging lens 32L, and the light detecting plane 34L intersect on the same straight line. As a result, the left photography system 30L may perform photography with all positions in the subject plane (e.g., the area from the anterior corneal surface to the posterior crystalline lens surface) in focus.

The right photography system 30R includes the reflector 31R, the imaging lens 32R, and the image sensor 33R. The reflector 31R and the imaging lens 32R direct light coming from the anterior segment (light traveling in the direction of the right photography system 30R) onto which the slit light is being projected by the illumination system 20 to the image sensor 33R. The right photography system 30R acquires a plurality of anterior segment images (a series of Scheimpflug images) by performing repetitive photography in parallel with movement of the illumination system 20, the left photography system 30L, and the right photography system 30R performed by the movement mechanism 6. The subject plane along the illumination optical axis 20a, the optical system that includes the reflector 31R and the imaging lens 32R, and the light detecting plane 34R satisfy the Scheimpflug condition.

The Scheimpflug image collection performed by the left photography system 30L and the Scheimpflug image collection performed by the right photography system 30R are performed in parallel with each other. The combination (the set) of a series of Scheimpflug images collected by the left photography system 30L and a series of Scheimpflug images collected by the right photography system 30R, is an example of the combination (the set) of the first Scheimpflug image group and the second Scheimpflug image group.

The controller 7 may perform synchronization between the repetitive photography carried out by the left photography system 30L and the repetitive photography carried out by the right photography system 30R. With the synchronization, a correspondence may be obtained between the series of Scheimpflug images obtained by the left photography system 30L and the series of Scheimpflug images obtained by the right photography system 30R. This correspondence is a temporal correspondence (a correspondence in terms of time), and more specifically, a correspondence that establishes pairs of images, each pair of images being acquired at substantially the same time point by the left photography system 30L and the right photography system 30R.

Alternatively, the controller 7 or the data processor 8 may execute a process of determining a correspondence between the plurality of anterior segment images obtained by the left photography system 30L and the plurality of anterior segment images obtained by the right photography system 30R. For example, the controller 7 or the data processor 8 can determine pairs of images from the anterior segment images sequentially input from the left photography system 30L and the anterior segment images sequentially input from the right photography system 30R, on the basis of their input timings.

The moving image photography system 40 acquires a moving image of the anterior segment of the subject's eye E from a fixed position in parallel with the photography performed by the left photography system 30L and the photography performed by the right photography system 30R. Here, the moving image photography system 40 is not moved by the movement mechanism 6. While the moving image photography system 40 of the present example is arranged coaxially with the illumination system 20, the arrangement of a moving image photography system is not limited to this. A moving image photography system of some examples may be arranged non-coaxially with the illumination system 20.

The light transmitted through the beam splitter 47 is reflected by the reflector 48 and enters the moving image photography system 40. The light that has entered the moving image photography system 40 is refracted by the objective lens 41 and then forms an image on the light detecting plane of the image sensor 43 by the imaging lens 42. The image sensor 43 may be an area sensor.

The moving image photography system 40 may be used for monitoring of the movement of the subject's eye E, alignment, tracking, and other operations. Further, the moving image photography system 40 may be used for processing of a series of Scheimpflug images.

Returning now to the reference of FIG. 12, the movement mechanism 6 is configured to move the illumination system 2 and the photography system 3 together with each other in the X direction.

The controller 7 is configured to control each part of the slit lamp microscope system 1. For example, the controller 7 controls the elements of the illumination system 2 (e.g., the illumination light source, the slit forming member, the focusing mechanism, etc.), the elements of the photography system 3 (e.g., the focusing mechanism of the optical system 3A, the image sensor 3B, etc.), the elements of the moving image photography system 4 (e.g., the focusing mechanism, the image sensor, etc.), the movement mechanism 6, the data processor 8, the communication unit 9, the user interface 10, and other elements.

The controller 7 may be configured to execute control of the illumination system 2, the photography system 3, and the movement mechanism 6, and control of the moving image photography system 4 in parallel with each other. With the parallel controls (simultaneous controls), the slit scanning (the collection of a series of Scheimpflug images) performed by the first image collecting unit 1010 (2010) and the repetitive photography (the collection of a series of time series images) performed by the second image collecting unit 1020 (2020) can be executed in parallel with each other.

Further, the controller 7 may be configured to execute control of the illumination system 2, the photography system 3, and the movement mechanism 6, and control of the moving image photography system 4 in synchronization with each other. With this, it becomes possible to synchronize the slit scanning performed by the first image collecting unit 1010 (2010) and the repetitive photography performed by the second image collecting unit 1020 (2020) with each other.

In the aspect example in which the photography system 3 includes the left photography system 30L and the right photography system 30R, the controller 7 may be configured to execute the repetitive photography performed by the left photography system 30L (the collection of the first Scheimpflug image group) and the repetitive photography performed by the right photography system 30R (the collection of the second Scheimpflug image group) in synchronization with each other.

The controller 7 includes a processor, a primary storage device, a secondary storage device, and the like. The secondary storage device retains computer programs such as various kinds of control programs. These computer programs may be stored in a computer or a storage device accessible by the slit lamp microscope system 1. The function of the controller 7 is implemented by cooperation of software such as the control program and hardware such as the processor.

The controller 7 may be capable of applying the following controls to the illumination system 2, the photography system 3, and the movement mechanism 6 in order to scan a three dimensional region of the anterior segment of the subject's eye E with the slit light.

First, the controller 7 controls the movement mechanism 6 to place the illumination system 2 and the photography system 3 at a predetermined scan start position. This control is referred to as alignment control. The scan start position is, for example, a position corresponding to the edge position (first edge position) of the cornea C in the X direction, or a position further away from the axis of the subject's eye E than the first edge position. The reference character X0 shown in FIG. 14A denotes a scan start position corresponding to the first edge position of the cornea C in the X direction. Further, the reference character X0' shown in FIG. 14B denotes a scan start position further away from the axis EA of the subject's eye E than the position corresponding to the first edge position of the cornea C in the X direction.

The controller 7 controls the illumination system 2 to start the projection of the slit light onto the anterior segment of subject's eye E. This control is referred to as slit light projection control. Further, the controller 7 controls the photography system 3 to start moving image photography (moving image acquisition) of the anterior segment of the subject's eye E. This control is referred to as photography control. After having executed the alignment control, the slit light projection control, and the photography control, the controller 7 performs control of the movement mechanism 6 to start the movement of the illumination system 2 and the photography system 3. This control is referred to as movement control. The illumination system 2 and the photography system 3 are moved together by the movement control. In other words, the movement mechanism 6 moves the illumination system 2 and the photography system 3 while maintaining the relative positions (e.g., the angle θ) between the illumination system 2 and the photography system 3, that is, while maintaining the state in which the Scheimpflug condition is satisfied. The movement of the illumination system 2 and the photography system 3 is performed from the aforementioned scan start position to a predetermined scan end position. The scan end position is, for example, a position corresponding to the edge position (second edge position) of the cornea C on the opposite side of the first edge position in the X direction, or a position further away from the axis of the subject's eye E than the second edge position, as in the scan start position.

The slit scanning of the present example is applied to the area from the scan start position to the scan end position. This slit scanning can be implemented by performing the followings in parallel with one another (in synchronization with one another, in an interlocking manner): the projection of the slit light onto the anterior segment; the integrated movement of the illumination system 2 and the photography system 3 in the X direction; and the moving image photography carried out by the photography system 3. Here, the width direction of the slit light is oriented in the X direction and the longitudinal direction of the slit light is oriented in the Y direction. The length of the slit light (that is, the size, in the Y direction, of the cross section of the light beam used as the slit light) is set to be, for example, equal to or greater than the diameter of the cornea C on the surface of the subject's eye E. Further, the distance of the movement of the illumination system 2 and the photography system 3 carried out by the movement mechanism 6 is set to be equal to or greater than the corneal diameter in the X direction. As a result of setting the slit light length and the movement distance in these manners, the slit scanning can be applied to the three dimensional region including the entire cornea C.

Figure 15:
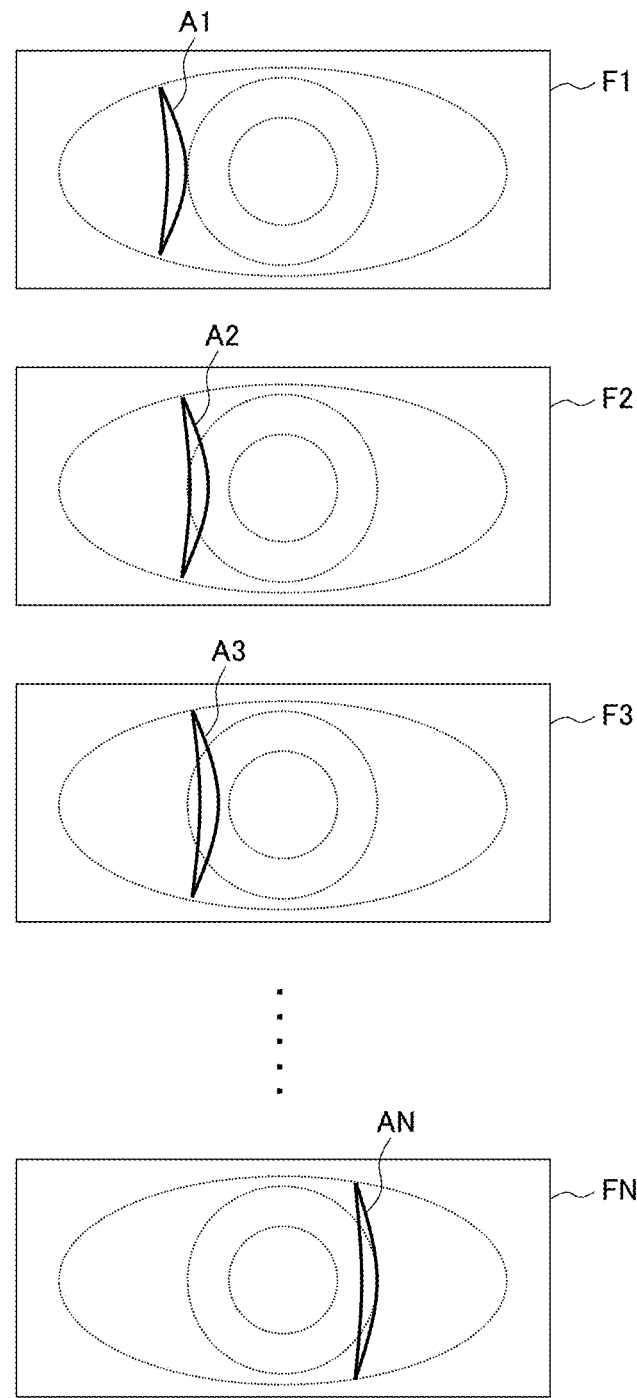
FIG. 15 is a diagram illustrating an operation executed by an ophthalmic imaging apparatus according to an aspect example.

With the slit scanning carried out in this way, a plurality of anterior segment images (a series of Scheimpflug images) corresponding to a plurality of mutually different slit light projection positions is acquired. In other words, a moving image is obtained in which the state (aspect) of the movement of the slit light projection position in the X direction is depicted. FIG. 15 shows an example of such a plurality of anterior segment images, that is, an example of such a group of frames (a frame group) composing a moving image.

FIG. 15 shows the plurality of anterior segment images (the frame group) F1, F2, F3, . . . , and FN. The subscripts "n" of the anterior segment images Fn (n=1, 2, . . . , N) represent a time series order. In other words, the n-th anterior segment image acquired is denoted by the reference character "Fn". The anterior segment image Fn includes the slit light image An. As shown in FIG. 15, the slit light images A1, A2, A3, . . . , and AN shift to the right in time series order. The scan start position and the scan end position in the example shown in FIG. 15 correspond to both edge positions of the cornea C in the X direction. A scan start position is not limited to that of the present example, and/or, a scan end position is not limited to that of the present example. In some examples, a scan start position may be a position further away from the axis of the subject's eye E than an edge position of the cornea, and/or, a scan end position may be a position further away from the axis of the subject's eye E than an edge position of the cornea. In addition, the direction of a scan, the number of scans, and any other scan conditions may be set in a freely selective manner.

The data processor 8 is configured to execute various kinds of data processing. Data to be processed may be either any data acquired by the slit lamp microscope system 1 or any data input from the outside.

The data processor 8 includes a processor, a primary storage device, a secondary storage device, and the like. The secondary storage device retains computer programs such as various kinds of data processing programs. These computer programs may be stored in a computer or a storage device accessible by the slit lamp microscope system 1. The function of the data processor 8 is implemented by cooperation of software such as the data processing program and hardware such as the processor.

Figure 16:
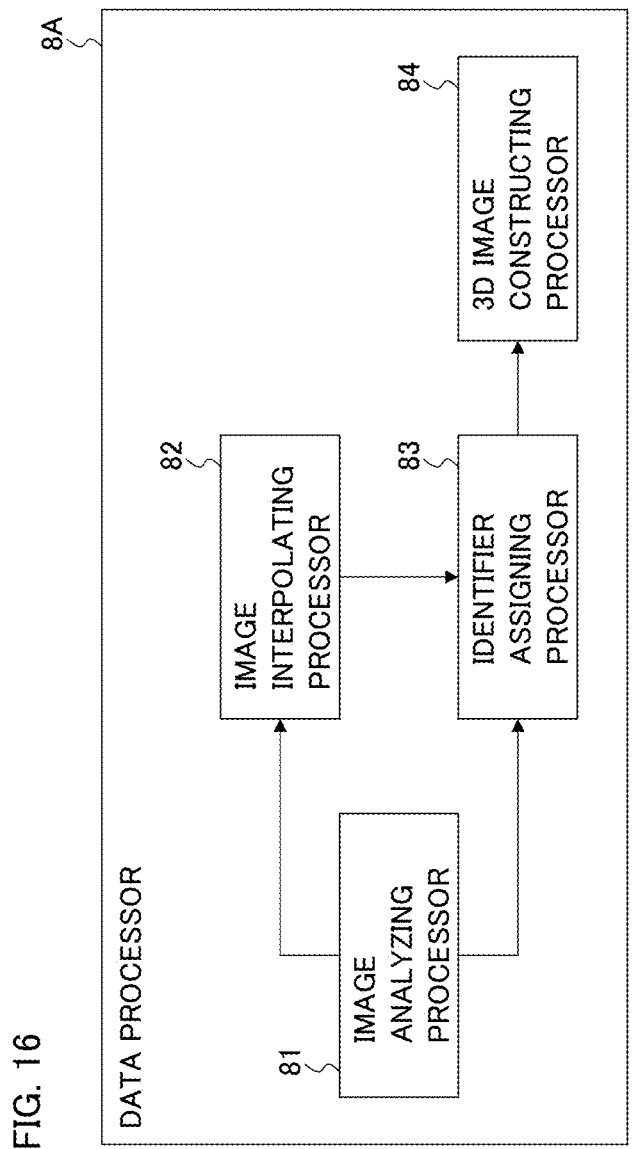
FIG. 16 is a diagram of a configuration of an ophthalmic imaging apparatus according to an aspect example.

FIG. 16 shows a configuration example of the data processor 8. The data processor 8A of the present example is capable of executing processing of a combination of spatial image interpolation and ocular tissue identifier assignment. The data processor 8A includes the image analyzing processor 81, the image interpolating processor 82, the identifier assigning processor 83, and the three dimensional image constructing processor 84.

The image analyzing processor 81 has any of the functions related to the first image analyzing unit 1030 of the first aspect example and any of the functions related to the second image analyzing unit 2030 of the second aspect example. The image analyzing processor 81 receives both an input of a plurality of anterior segment images (a series of Scheimpflug images) collected from a three dimensional region of the anterior segment of the subject's eye E by slit scanning, and an input of a moving image (a series of time series images) acquired by the moving image photography system 4 in parallel with the slit scanning.

In some examples, as described above, the image analyzing processor 81 analyzes the series of time series images collected by the moving image photography system 4 to detect a series of slit light images, and then calculates time series shifts of the slit light on the basis of the series of slit light images detected. A result of the detection of the slit light images is sent to the identifier assigning processor 83 while information on the time series shifts of the slit light is sent to the image interpolating processor 82.

The image interpolating processor 82 has any of the functions related to the image interpolating unit 1040 of the first aspect example. The image interpolating processor 82 performs interpolation of the series of Scheimpflug images collected by the slit scanning, based on the time series shifts of the slit light obtained by the image analyzing processor 81. A plurality of Scheimpflug images obtained by this interpolation process, which includes the series of Scheimpflug images collected and an image group added by this interpolation process, is sent to the identifier assigning processor 83.

The image interpolating processor 82 of some aspect examples may have the same or similar configuration as or to the image interpolating unit 1040A of FIG. 6A, and may be configured to perform spatial image interpolation using an inference model.

The image interpolating processor 82 of some aspect examples includes a configuration same as or similar to the image interpolating unit 1040B in FIG. 7 and/or a configuration same as or similar to the image interpolating unit 1040C in FIG. 8. The image interpolating processor 82 of some aspect examples may be capable of determining interpolation quantity on the basis of at least one of the following pieces of information: operation information of the first image collecting unit (the illumination system 2, the photography system 3, and the movement mechanism 6); information on the time series shifts of the slit light; and information on the time series shifts of the subject's eye. In addition to this, the image interpolating processor 82 may be configured to generate images of the determined interpolation quantity and then add the generated images to the series of Scheimpflug images collected.

The identifier assigning processor 83 has any of the functions related to the identifier assigning unit 2040 of the second aspect example. The identifier assigning processor 83 performs assignment of an ocular tissue identifier to each of the series of Scheimpflug images collected by the slit scanning, based on the series of slit light images detected from the series of time series images collected by the moving image photography system 4.

Furthermore, the identifier assigning processor 83 may be configured to be capable of performing assignment of an ocular tissue identifier to each of the image groups (to each supplementary image of the supplementary image group) added to the series of Scheimpflug images by the image interpolating processor 82. The process of assigning an ocular tissue identifier to each supplementary image may be any of the above-mentioned processes usable for assignment of an ocular tissue identifier to each Scheimpflug image (each collected image).

In some alternative examples, the identifier assigning processor 83 may be configured to perform assignment of ocular tissue identifiers to the supplementary image group based on the ocular tissue identifiers assigned to the series of Scheimpflug images. In some aspect examples, the identifier assigning processor 83 may be configured to assign, to each of supplementary images that are inserted between two adjacent Scheimpflug images (e.g., between the two anterior segment images Fn and F(n+1) in FIG. 15) to which identifiers representing the same ocular tissue are assigned, the same ocular tissue identifier as the ocular tissue identifiers assigned to these two Scheimpflug images. For example, in the case in which an identifier representing the cornea is assigned to both the two anterior segment images Fn and F(n+1) in FIG. 15, the identifier assigning processor 83 can assign an identifier representing the cornea to each image inserted between the anterior segment image Fn and the anterior segment image F(n+1) by the image interpolating processor 82.

In some aspect examples, the identifier assigning processor 83 may be configured to be capable of applying, to each supplementary image, processing that is the same as or similar to the processing for assigning ocular tissue identifiers to Scheimpflug images (the first ocular tissue identifier assignment process). This completes the processing for each supplementary image to which an ocular tissue identifier has been appropriately assigned by the first ocular tissue identifier assignment process. To each supplementary image to which the first ocular tissue identifier assignment process has not assigned an appropriate ocular tissue identifier, the identifier assigning processor 83 may assign an ocular tissue identifier determined based on the ocular tissue identifiers assigned to the series of Scheimpflug images (the second ocular tissue identifier assignment process). The order of the stepwise processes described above is not limited to the order of the present example. The order of the stepwise processes of some examples may be the reverse order of the present example. In some examples, any two or more different processes may be executed step by step.

In some aspect examples, in the case in which there exist one or more Scheimpflug images of the series of Scheimpflug images to each of which an ocular tissue identifier has not been appropriately assigned, the identifier assigning processor 83 may first execute selection of one or more supplementary images located in the vicinity of a corresponding Scheimpflug image, such as selection of one or more supplementary images adjacent to a corresponding Scheimpflug image. Then, the identifier assigning processor 83 may execute assignment of an ocular tissue identifier to each selected supplementary image by applying the same or similar processing as or to the processing performed for assigning an ocular tissue identifier to a Scheimpflug image. Subsequently, the identifier assigning processor 83 may execute assignment of an ocular tissue identifier to a target Scheimpflug image (that is, a Scheimpflug image to which an ocular tissue identifier has not been appropriately assigned), based at least on the one or more supplementary images to which the ocular tissue identifiers have been assigned.

The three dimensional image constructing processor 84 constructs a three dimensional image, based on a plurality of anterior segment images which includes the series of Scheimpflug images collected and the supplementary image group and to each of which an ocular tissue identifier is assigned by the identifier assigning processor 83. This three dimensional image is an image (image data) in which pixel positions are defined by a three dimensional coordinate system. Volume data (also referred to as voxel data) is an example of a three dimensional image. The three dimensional image constructing processor 84 is configured to execute any known three dimensional image construction technique such as computer graphics.

The slit lamp microscope system 1 of the present example is configured to execute both application of spatial image interpolation to a series of Scheimpflug images collected from a three dimensional region of subject's eye E, and assignment of an ocular tissue identifier to each of a plurality of images obtained through the interpolation (e.g., this plurality of images consists of the series of Scheimpflug images and a supplementary image group). The present example having such a configuration can produce both the advantageous effects of the first aspect example and the advantageous effects of the second aspect example. Further, since the present example is configured to be capable of linking the spatial image interpolation and the ocular tissue identifier assignment, it becomes possible to further improve the performance of ophthalmic imaging apparatuses configured to be capable of conducting slit scanning.

Figure 17:
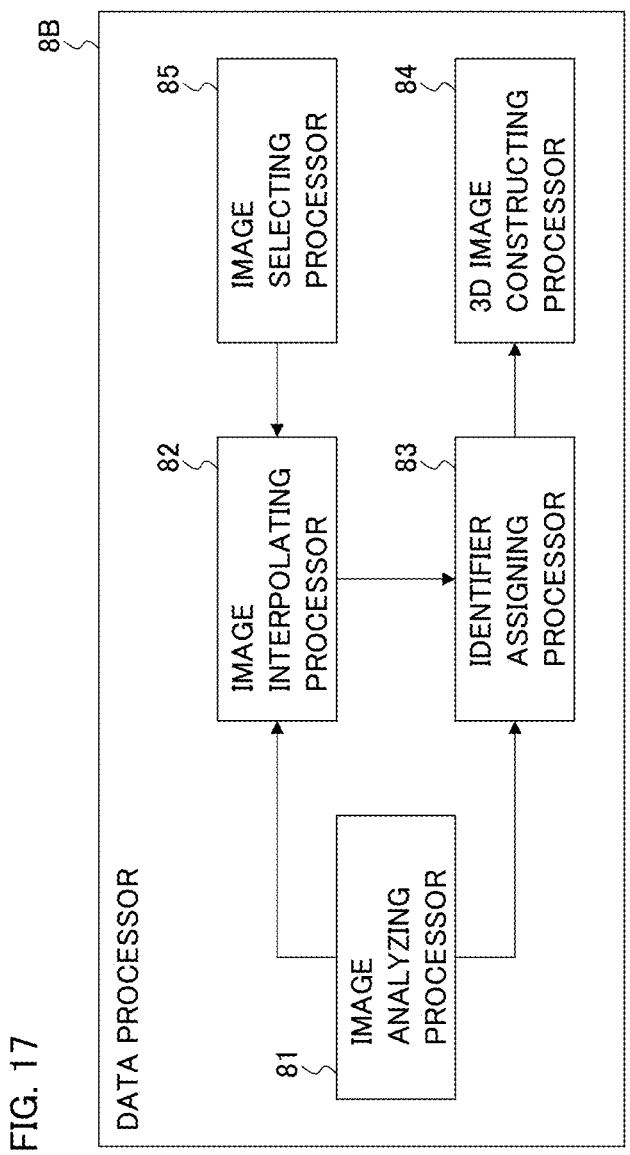
FIG. 17 is a diagram of a configuration of an ophthalmic imaging apparatus according to an aspect example.

FIG. 17 shows another configuration example of the data processor 8. As with the data processor 8A of FIG. 16, the data processor 8B of the present example includes the image analyzing processor 81, the image interpolating processor 82, the identifier assigning processor 83, and the three dimensional image constructing processor 84. In addition to these elements, the data processor 8B of the present example includes the image selecting processor 85. Descriptions of the same or similar elements as in the data processor 8A will be omitted.

The photography system 3 of the present example includes a first photography system and a second photography system such as the left photography system 30L and the right photography system 30R in FIG. 13. In the slit scanning of the present example, the collection of a series of Scheimpflug images performed by the left photography system 30L and the collection of a series of Scheimpflug images performed by the right photography system 30R are performed in parallel.

The image selecting processor 85 is configured to perform, based on a correspondence between a series of Scheimpflug images collected by the left photography system 30L and a series of Scheimpflug images collected by the right photography system 30R (that is, a correspondence between the first Scheimpflug image group and the second Scheimpflug image group), selection of another series of Scheimpflug images corresponding to the slit scanning from the first Scheimpflug image group and the second Scheimpflug image group. The image selecting processor 85 has any of the functions related to the image selecting unit 1050 of the first aspect example. The image interpolating processor 82 of the present example is configured to apply spatial image interpolation to the another series of Scheimpflug images formed by the image selecting processor 85.

The slit lamp microscope system 1 of the present example may include an illumination system such as the illumination system 20 of FIG. 13. The image selecting processor 85 may be configured to be capable of performing, based on the correspondence between the series of Scheimpflug images collected by the left photography system 30L and the series of Scheimpflug images collected by the right photography system 30R, selection of a plurality of Scheimpflug images containing no corneal reflection artifact from these two series of Scheimpflug images. The image interpolating processor 82 of the present example is configured to apply spatial image interpolation to the another series of Scheimpflug images containing no corneal reflection artifact formed in this way.

The slit lamp microscope system 1 of the present example is configured to perform the following processes: a process of applying spatial image interpolation to another series of Scheimpflug images constructed by performing selection from a group of Scheimpflug images including the series of Scheimpflug images collected by the left photography system 30L and the series of Scheimpflug images collected by the right photography system 30R; and a process of performing assignment of an ocular tissue identifier to each of a plurality of images obtained through the interpolation, such as the another series of Scheimpflug images and a supplementary image group. The present example having such a configuration also produces the advantageous effects of the aspect examples including the image selecting unit 1050 in addition to the advantageous effects of the first aspect example and the advantageous effects of the second aspect example. Furthermore, the present example is capable of executing Scheimpflug image selection, spatial image interpolation, and ocular tissue identifier assignment in an interlocking manner, thereby further improving the performance of ophthalmic imaging apparatuses configured to be capable of performing slit scanning.

The configuration of the data processor 8 is not limited to the above examples. The data processor 8 of some aspect examples may have one or both of the followings: any of the data processing functions of the first aspect example; and any of the data processing functions of the second aspect example. Further, the data processor 8 of some aspect examples may have any of the data processing functions related to the technique or technology disclosed by the applicant of the present application, such as any of the data processing functions disclosed in the following document relating to a patent application filed by the applicant of the present application: Japanese Unexamined Patent Application Publication No. 2019-213733 (PCT International Publication No. 2019/240149).

The communication unit 9 performs data communication between the slit lamp microscope system 1 and another apparatus. In other words, the communication unit 9 performs transmission of data to another apparatus and reception of data transmitted from another apparatus.

The system or method of the data communication executed by the communication unit 9 may be selected accordingly. For example, the communication unit 9 may include any one or more of various kinds of communication interfaces such as a communication interface conforming to the Internet, a communication interface conforming to a dedicated line, a communication interface conforming to a local area network (LAN), and a communication interface conforming to near field communication. The data communication may include any one or both of wireless communication and wired communication.

Data sent and received by the communication unit 9 may be encrypted. If this is the case, for example, any one or both of the controller 7 and the data processor 8 include(s) at least one of an encryptor and a decryptor. The encryptor is configured to encrypt data to be sent by the communication unit 9. The decryptor is configured to decrypt data having been received by the communication unit 9.

The user interface 10 includes one or more freely selected user interface devices such as one or more display devices and one or more operation devices. Users such as doctors, subjects, and assistants can conduct operations of the slit lamp microscope system 1 and input of information to the slit lamp microscope system 1 by using the user interface 10.

The display device is configured to display various kinds of information under the control of the controller 7. The display device may include a flat panel display such as a liquid crystal display (LCD). The operation device includes a device for operating the slit lamp microscope system 1 and/or a device for inputting information. The operation device includes, for example, a button, a switch, a lever, a dial, a handle, a knob, a mouse, a keyboard, a trackball, an operation panel, or the like. A device such as a touch screen may be employed in which a display device and an operation device are integrated.

At least part of the user interface for the slit lamp microscope system 1 may be disposed as a peripheral device(s) of the slit lamp microscope system 1.

The elements of the slit lamp microscope system 1 are not limited to those described above. The slit lamp microscope system 1 may include one or more freely selected elements that can be combined with or incorporated in a slit lamp microscope. More generally, the slit lamp microscope system 1 may include one or more freely selected elements that can be combined with or incorporated in an ophthalmic imaging apparatus. Further, the slit lamp microscope system 1 may include one or more freely selected elements for executing processing of data acquired from a subject's eye by using a slit lamp microscope. More generally, the slit lamp microscope system 1 may include one or more freely selected elements for executing processing of any ophthalmic data.

In some examples, the slit lamp microscope system 1 may be provided with a fixation system configured to output light for fixation of the subject's eye E (referred to as fixation light). The fixation system in some typical examples includes at least one visible light source (referred to as a fixation light source(s)) or a display device configured to display an image such as a landscape chart or a fixation target. The fixation system of some example aspects is arranged coaxially or non-coaxially with the illumination system 2 or the photography system 3.

Figure 18:
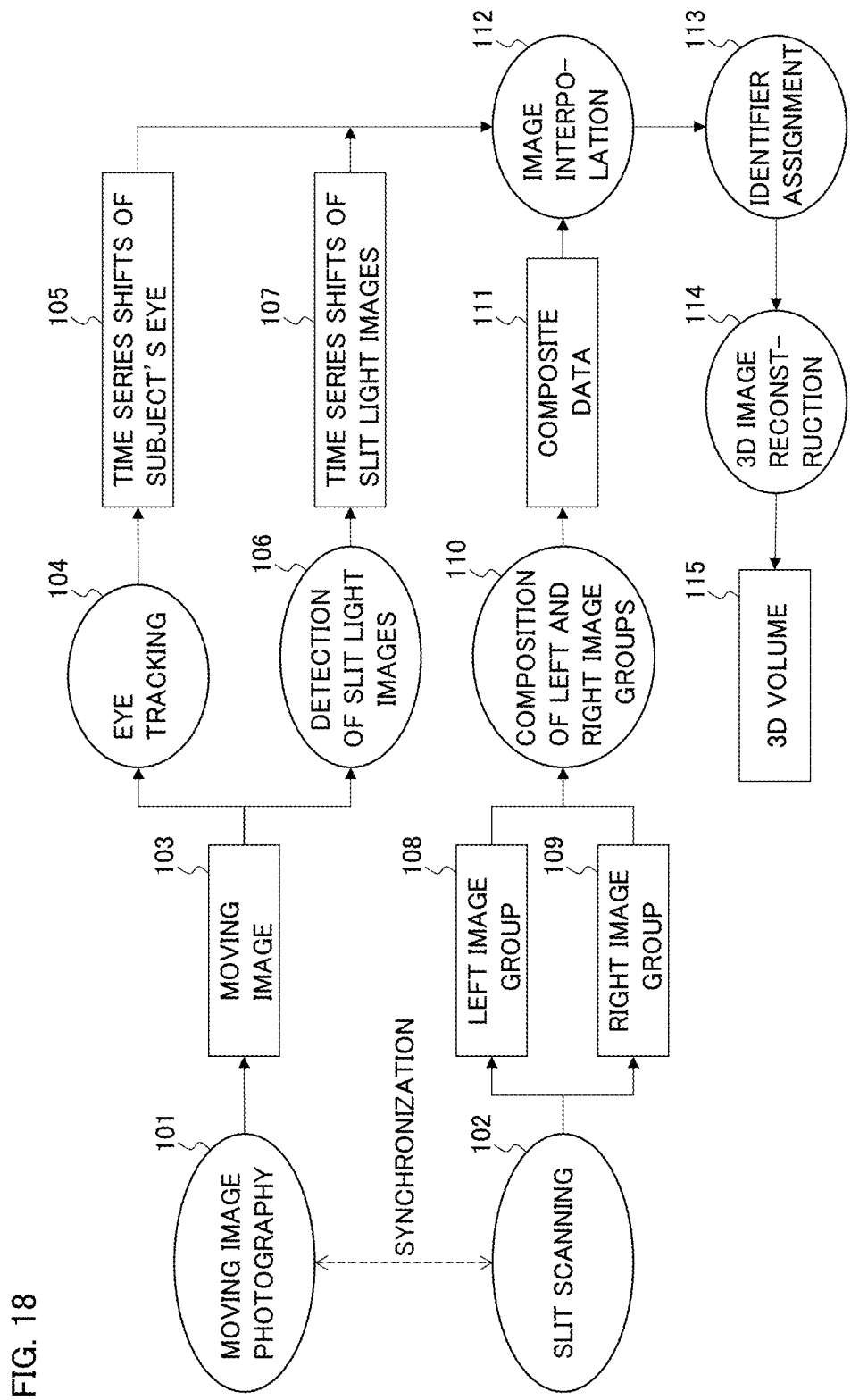
FIG. 18 is a data-flow diagram illustrating a usage mode of an ophthalmic imaging apparatus according to an aspect example.

An example of the usage mode of the slit lamp microscope system 1 of the present aspect example will now be described. FIG. 18 is a data-flow diagram showing the flow of the present example. Each ellipse in FIG. 18 represents processing (process) or operation, and each rectangle represents data.

To begin with, the slit lamp microscope system 1 performs the moving image photography 101 using the moving image photography system 4 and performs the slit scanning 102 using the illumination system 2, the photography system 3, and the movement mechanism 6. The controller 7 executes synchronization control for synchronizing the moving image photography 101 and the slit scanning 102 with each other.

A moving image (a series of time series images) 103 acquired by the moving image photography 101 is used for the eye tracking 104 and the detection of slit light images 106.

The eye tracking 104 includes at least a process of analyzing the moving image 103 to detect the movement of the subject's eye E. In other words, the eye tracking 104 includes at least a process of detecting the position of the subject's eye E at each of a plurality of time points. The eye tracking 104 may further include an operation of moving the optical system in real time on the basis of the detected movement of the subject's eye E. This operation is performed for making the optical system follow the movement of the subject's eye E. By the eye tracking 104 performed in this way, the time series shift of subject's eye E 105 is obtained.

The detection of slit light images 106 includes a process of analyzing the moving image 103 to detect a series of slit light images. By the detection of slit light images 106, the time series shift of slit light image 107 is obtained.

By the time series shift of subject's eye E 105 and the time series shift of slit light image 107, the slit lamp microscope system 1 can correct the artifacts caused by the eye movement of the subject's eye E and the artifacts caused by the nonconstancy of speed of the slit scanning. The image interpolating processor 82 receives an input of the time series shift of subject's eye E 105 and an input of the time series shift of slit light image 107.

On the other hand, the slit scanning 102 collects a series of Scheimpflug images from a three dimensional region of the anterior segment of the subject's eye E. The slit lamp microscope system 1 of the present example includes the left photography system 30L and the right photography system 30R shown in FIG. 13 (also in FIG. 4 and FIG. 5). In the slit scanning 102, the left photography system 30L collects a series of Scheimpflug images (the left image group 108) and the right photography system 30R collects a series of Scheimpflug images (the right image group 109). In the slit scanning 102, the controller 7 executes synchronization control for synchronizing the left photography system 30L and the right photography system 30R with each other. As a result, the controller 7 executes synchronization control for synchronizing the moving image photography system 40, the left photography system 30L, and the right photography system 30R with one another.

The left image group 108 and the right image group 109 collected by the slit scanning 102 are input to the image selecting processor 85. The image selecting processor 85 composes (synthesizes, combines) the left image group 108 and the right image group 109 (the composition of left and right image groups 110). The composition of left and right image groups 110 is a process of selecting another series of Scheimpflug images corresponding to the slit scanning 102 from the left image group 108 and the right image group 109 based on a correspondence between the left image group 108 and the right image group 109.

The composition of left and right image groups 110 can remove artifacts such as corneal reflection artifacts. In other words, the composition of left and right image groups 110 generates a new series of Scheimpflug images (the composite data 111) that contains no artifacts such as corneal reflex artifacts. The composite data 111 is input to the image interpolating processor 82.

To the image interpolating processor 82, the time series shift of subject's eye E 105, the time series shift of slit light image 107, and the composite data 111 are input. In the image interpolation 112, the image interpolating processor 82 first determines a condition for the spatial image interpolation based on the time series shift of subject's eye E 105 and the time series shift of slit light image 107. The condition of the spatial image interpolation may include, for example, at least one of interpolation quantity, interpolation position, and interpolation interval. The image interpolating processor 82 may be configured to determine the condition of the spatial image interpolation based on at least one of the condition of the slit scanning 102 (the operation information of the first image collecting unit 1010 described above), the time series shift of subject's eye E 105, and the time series shift of slit light image 107.

In the image interpolation 112, the image interpolating processor 82 further applies the spatial image interpolation to the composite data 111 based on the condition determined in the previous step. This spatial image interpolation can be performed without changing the intervals between a plurality of images constituting the composite data 111.

It should be noted that, in the spatial image interpolation of some aspect examples, fine adjustment (fine tuning) of the intervals between the plurality of images constituting the composite data 111 may be conducted. This fine adjustment can be performed without substantially changing the aspect ratio, in the XY plane, of the three dimensional region represented by the composite data 111 (the left image group 108, the right image group 109).

A plurality of images (including the composite data 111 and a supplementary image group) obtained by the image interpolation 112 is input to the identifier assigning processor 83.

The identifier assigning processor 83 assigns an ocular tissue identifier to each of the plurality of images (including the composite data 111 and the supplementary image group) obtained by the image interpolation 112 (the identifier assignment 113). The plurality of images with ocular tissue identifiers assigned are input to the three dimensional image constructing processor 84.

The three dimensional image constructing processor 84 constructs a three dimensional image based on the plurality of images (including the composite data 111 and the supplementary image group) input from the identifier assigning processor 83 (the three dimensional image reconstruction 114). As a result of the three dimensional image reconstruction 114, the three dimensional volume 115 representing the three dimensional region (the three dimensional region to which the slit scanning 102 is applied) of the anterior segment of the subject's eye E is obtained. The three dimensional volume 115 may be used for a post-stage processing such as rendering and image analysis.

By performing the image interpolation 112, the slit lamp microscope system 1 is capable of making the aspect ratio of a three dimensional volume and the aspect ratio of its rendered image the same as or similar to the actual morphology of the subject's eye E (the actual morphology of the three dimensional region to which the slit scanning 102 is applied).

Further, in the image interpolation 112, the slit lamp microscope system 1 may change the interpolation quantity for each interval of the array of the plurality of images constituting the composite data 111, based on the time series shift of subject's eye E 105 and/or the time series shift of slit light image 107. This makes the slit lamp microscope system 1 capable of correcting artifacts such as an artifact caused by the eye movement of the subject's eye E occurred during the application of the slit scanning 102 to the subject's eye E, an artifact caused by the nonconstancy of speed of the slit scanning 102, and the like.

Furthermore, by constructing the composite data 111, the slit lamp microscope system 1 is capable of removing an artifact caused by corneal reflection of the slit light.

As described thus far, according to the present example, the slit lamp microscope system 1 is capable of generating a three dimensional image not only that has an aspect ratio corresponding to the actual morphology of the anterior eye segment and but also that does not contain various kinds of artifacts such as an artifact caused by corneal reflection, an artifact caused by eye movement, and an artifact caused by nonconstancy of speed of the slit scanning. Further, from such a three dimensional image, the slit lamp microscope system 1 is capable of creating a rendered image not only that has an aspect ratio corresponding to the actual morphology of the anterior eye segment and but also that does not contain various kinds of artifacts. In addition, the slit lamp microscope system 1 is capable of performing image analysis of the subject's eye E using a three dimensional image or a rendered image not only that has an aspect ratio corresponding to the actual morphology of the anterior eye segment and but also that does not contain various kinds of artifacts. In this way, the present example is capable of improving the performance of slit scanning of a three dimensional region of the subject's eye.

Further, according to the present example, the slit lamp microscope system 1 is capable of performing assignment of an ocular tissue identifier to each image constituting the composite data 111. Therefore, the user can easily and correctly perceive the type of an ocular tissue depicted in an image used in tasks such as medical observation and medical diagnosis and data processing such as data analysis. In addition, analysis of Scheimpflug images can be conducted in a more appropriate manner than before.

The usage mode of the slit lamp microscope system 1 of the present aspect example is not limited to the present example described in detail above. For example, some usage mode examples may include any matters and items of the first aspect example and/or any matters and items of the second aspect example.

Non-Limiting Fourth Aspect Example

The first to third aspect examples described thus far relate to an ophthalmic imaging apparatus that has the function of collecting a series of Scheimpflug images and the function of collecting a series of time series images. On the other hand, the fourth aspect example relates to an ophthalmic image processing apparatus (computer, information processing apparatus) that receives images of a subject's eye from the outside.

The ophthalmic image processing apparatus of some aspect examples includes a receiver, a first image analyzing unit, and an image interpolating unit.

The receiver receives both a series of images acquired by performing scanning of a three dimensional region of a subject's eye with scan light and a series of time series images collected by performing repetitive photography of the subject's eye in parallel with the scanning of the three dimensional region. The receiver of some examples includes a communication device and/or a media drive. The communication device may be, for example, the communication unit 9 of the third aspect example, and receives data stored in an external storage device. The media drive reads out data recorded on a recording medium.

The series of images acquired by performing the scanning of the three dimensional region of the subject's eye with the scan light may be either of the followings, for example: a series of Scheimpflug images collected by slit scanning; or another series of Scheimpflug images constructed from the first Scheimpflug image group and the second Scheimpflug image group collected by the first photography system and the second photography system, respectively. In some alternative examples, the series of images acquired by performing the scanning of the three dimensional region of the subject's eye with the scan light may include images acquired by a modality other than a slit lamp microscope. For example, the series of images acquired by performing the scanning of the three dimensional region of the subject's eye with the scan light may include a series of images collected by any ophthalmic scanning modality such as OCT and SLO.

The first image analyzing unit of the ophthalmic image processing apparatus is configured to analyze the series of time series images received by the receiver, thereby determining time series shifts of the scan light. The first image analyzing unit may be, for example, either of the first image analyzing unit 1030 of the first aspect example or the image analyzing processor 81 of the third aspect example.

The image interpolating unit of the ophthalmic image processing apparatus is configured to perform interpolation of the series of images acquired by performing the scanning with the scan light, based on the time series shifts of the scan light determined by the first image analyzing unit. The image interpolating unit may be, for example, either of the image interpolating unit 1040 of the first aspect example or the image interpolating processor 82 of the third aspect example.

With the configuration described above, the ophthalmic image processing apparatus of the present aspect example is capable of generating a plurality of images disposed in accordance with an aspect ratio corresponding to the actual morphology of the subject's eye, and hence constructing a three dimensional image and a rendered image with an aspect ratio corresponding to the actual morphology of the subject's eye. Any matters and items of the present disclosure can be combined with or incorporated in the ophthalmic image processing apparatus of the present aspect example.

The ophthalmic image processing apparatus of some aspect examples includes a receiver, a second image analyzing unit, and an identifier assigning unit.

The receiver receives both a series of images acquired by performing scanning of a three dimensional region of a subject's eye with scan light and a series of time series images collected by performing repetitive photography of the subject's eye in parallel with the scanning of the three dimensional region. The receiver of the ophthalmic image processing apparatus of the present aspect example may be the same as the receiver of the ophthalmic image processing apparatus of the above-mentioned aspect example.

The second image analyzing unit of the ophthalmic image processing apparatus of the present aspect example is configured to analyze the series of time series images received by the receiver, thereby detecting a series of images of the scan light. The second image analyzing unit may be, for example, either of the second image analyzing unit 2030 of the second aspect example or the image analyzing processor 81 of the third aspect example.

The identifier assigning unit of the ophthalmic image processing apparatus of the present aspect example is configured to perform assignment of an identifier to each of the series of images acquired by performing the scanning of the three dimensional region of the subject's eye with the scan light, based on the series of images of the scan light detected by the second image analyzing unit. Here, an identifier assigned to an image represents an ocular tissue onto which the scan light is being projected at the time point when this image is acquired. The identifier assigning unit may be, for example, either of the identifier assigning unit 2040 of the second aspect example or the identifier assigning processor 83 of the third aspect example.

With the configuration described above, the ophthalmic image processing apparatus of the present aspect example is capable of performing assignment of an ocular tissue identifier to each of the series of images acquired by performing the scanning of the three dimensional region of the subject's eye with the scan light. Therefore, the user can easily and correctly perceive the type of an ocular tissue depicted in an image used in tasks such as medical observation and medical diagnosis and data processing such as data analysis. In addition, In addition, analysis of Scheimpflug images can be conducted in a more appropriate manner than before.

The ophthalmic image processing apparatus of aspect examples is not limited to the above example. In some examples, an ophthalmic image processing apparatus may be configured with any of the matters and items in the present disclosure.

Other Matters and Items

The present disclosure presents several aspect examples of embodiments. These aspect examples are merely examples of the present invention. Therefore, any modification (e.g., omission, substitution, replacement, addition, etc.) may be made within the scope of the present invention to the aspect examples described in present disclosure.

It is possible to configure a program that causes a computer to execute any one or more of the processes described in the present disclosure. It is also possible to create a recording medium that retains such a program. The recording medium is a computer-readable non-transitory recording medium. The non-transitory recording medium may be in any form, and examples of the non-transitory recording medium include a magnetic disk, an optical disk, a magneto-optical disk, and a semiconductor memory.

The present invention may include a method including any one or more steps described in the present disclosure. For example, a method of some aspect examples may be configured to perform the following steps: a step of performing scanning of a three dimensional region of a subject's eye with slit light to collect a series of Scheimpflug images; a step of performing repetitive photography of the subject's eye in parallel with the scanning of the three dimensional region to collect a series of time series images; a step of analyzing the series of time series images to determine time series shifts of the slit light during the scanning; and a step of performing interpolation of the series of Scheimpflug images based on the time series shifts of the slit light. One or more steps based on any matters and items in the present disclosure may be combined with or incorporated in the method of the present aspect example. Note that instead of the step of collecting images, a step of receiving images from the outside may be provided.

A method according to some aspect examples is configured to perform the following steps: a step of performing scanning of a three dimensional region of a subject's eye with slit light to collect a series of Scheimpflug images; a step of performing repetitive photography of the subject's eye in parallel with the scanning of the three dimensional region to collect a series of time series images; a step of analyzing the series of time series images to detect a series of images of the slit light; and a step of performing assignment of an identifier to each of the Scheimpflug images based on the series of images of the slit light detected from the series of time series images. Here, an identifier assigned to a Scheimpflug image represents an ocular tissue onto which the slit light is being projected at the time point when this corresponding Scheimpflug image is acquired. One or more steps based on any matters and items in the present disclosure may be combined with or incorporated in the method of the present aspect example. Note that instead of the step of collecting images, a step of receiving images from the outside may be provided.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic imaging apparatus comprising:
   a first image collecting unit configured to collect a series of Scheimpflug images by performing scanning of a three dimensional region of a subject's eye with slit light;
   a second image collecting unit configured to collect a series of time series images by performing repetitive photography of the subject's eye in parallel with the scanning of the three dimensional region performed by the first image collecting unit;
   processor circuitry configured as a first image analyzing unit configured to analyze the series of time series images to determine time series shifts of the slit light during the scanning of the three dimensional region; and
   the processor circuitry further configured as an image interpolating unit configured to perform interpolation of the series of Scheimpflug images based on the time series shifts of the slit light.

2. The ophthalmic imaging apparatus of claim 1, wherein the first image analyzing unit is further configured to analyze the series of time series images to detect a series of images of the slit light, and determine the time series shifts of the slit light based on the series of images of the slit light.

3. The ophthalmic imaging apparatus of claim 1, wherein the scanning of the three dimensional region performed by the first image collecting unit and the repetitive photography of the subject's eye performed by the second image collecting unit are performed in synchronization with each other, and the image interpolating unit is further configured to perform the interpolation of the series of Scheimpflug images based further on a correspondence between the series of Scheimpflug images and the series of time series images, the correspondence being determined based on the synchronization between the scanning of the three dimensional region and the repetitive photography of the subject's eye.

4. The ophthalmic imaging apparatus of claim 1, wherein the first image collecting unit includes a first photography system and a second photography system that are configured to perform photography of the subject's eye from mutually different directions for the scanning of the three dimensional region, wherein
   the first photography system is configured to collect a first Scheimpflug image group, and
   the second photography system is configured to collect a second Scheimpflug image group, and
   wherein the series of Scheimpflug images includes the first Scheimpflug image group and the second Scheimpflug image group.

5. The ophthalmic imaging apparatus of claim 4, wherein photography performed by the first photography system and photography performed by the second photography system are performed in synchronization with each other.

6. The ophthalmic imaging apparatus of claim 5, wherein the processor circuitry is further configured as an image selecting unit configured to perform selection of another series of Scheimpflug images corresponding to the scanning of the three dimensional region from the first Scheimpflug image group and the second Scheimpflug image group based on a correspondence between the first Scheimpflug image group and the second Scheimpflug image group, the correspondence being determined based on the synchronization between the photography performed by the first photography system and the photography performed by the second photography system,
   wherein the image interpolating unit is further configured to perform interpolation of the another series of Scheimpflug images.

7. The ophthalmic imaging apparatus of claim 6, wherein the first image collecting unit further includes an illumination system configured to project the slit light onto the three dimensional region, wherein
   an optical axis of the first photography system and an optical axis of the second photography system are arranged in an oblique manner in mutually opposite directions relative to an optical axis of the illumination system, and
   the image selecting unit is further configured to perform the selection of the another series of Scheimpflug images by selecting a plurality of Scheimpflug images containing no corneal reflection artifact from the first Scheimpflug image group and the second Scheimpflug image group based on the correspondence between the first Scheimpflug image group and the second Scheimpflug image group.

8. The ophthalmic imaging apparatus of claim 1, wherein the image interpolating unit is further configured to perform the interpolation of the series of Scheimpflug images using an optical flow that represents a shift of the subject's eye depicted in the series of Scheimpflug images as a vector.

9. The ophthalmic imaging apparatus of claim 1, wherein the image interpolating unit is further configured to perform the interpolation of the series of Scheimpflug images using an inference model constructed in advance, wherein the inference model is constructed in advance by applying machine learning with training data including at least a Scheimpflug image of an eye to a neural network, and is configured to receive an input of two or more Scheimpflug images representing two or more different locations of a same eye and to generate an output of a spatially interpolated image of the two or more Scheimpflug images.

10. The ophthalmic imaging apparatus of claim 1, wherein the image interpolating unit includes a first interpolation quantity determining unit configured to determine an interpolation quantity based on one or both of operation information of the first image collecting unit and the time series shifts of the slit light, and
   wherein the image interpolating unit is further configured to perform the interpolation of the series of Scheimpflug images with images of the interpolation quantity.

11. The ophthalmic imaging apparatus of claim 1, wherein
   the first image analyzing unit is further configured to analyze the series of time series images collected by the second image collecting unit to determine time series shifts of the subject's eye, and
   the image interpolating unit further includes a second interpolation quantity determining unit configured to determine an interpolation quantity based on one or both of operation information of the first image collecting unit and the time series shifts of the subject's eye, and
   wherein the image interpolating unit is further configured to perform the interpolation of the series of Scheimpflug images with images of the interpolation quantity.

12. An ophthalmic imaging apparatus comprising:
   a first image collecting unit configured to collect a series of Scheimpflug images by performing scanning of a three dimensional region of a subject's eye with slit light;
   a second image collecting unit configured to collect a series of time series images by performing repetitive photography of the subject's eye in parallel with the scanning of the three dimensional region performed by the first image collecting unit;
   processor circuitry configured as a second image analyzing unit configured to analyze the series of time series images to detect a series of images of the slit light; and
   the processor circuitry further configured as an identifier assigning unit configured to perform assignment of an identifier to each of the series of Scheimpflug images based on the series of images of the slit light detected from the series of time series images, the identifier representing an ocular tissue onto which the slit light is being projected when a corresponding Scheimpflug image is acquired.

13. The ophthalmic imaging apparatus of claim 12, wherein
   the scanning of the three dimensional region performed by the first image collecting unit and the repetitive photography of the subject's eye performed by the second image collecting unit are performed in synchronization with each other, and
   the identifier assigning unit is further configured to perform the assignment of the identifier based further on a correspondence between the series of Scheimpflug images and the series of time series images, the correspondence being determined based on the synchronization between the scanning of the three dimensional region and the repetitive photography of the subject's eye.

14. The ophthalmic imaging apparatus of claim 13, wherein the identifier assigning unit is further configured to perform assignment of a series of identifiers to the series of time series images based on the series of images of the slit light, and to perform the assignment of the identifier to each of the series of Scheimpflug images based on the series of identifiers assigned to the series of time series images and the correspondence.

15. The ophthalmic imaging apparatus of claim 12, wherein
   the second image analyzing unit is further configured to analyze the series of Scheimpflug images to detect a series of images of the slit light, and
   the identifier assigning unit is further configured to perform the assignment of the identifier based on the series of images of the slit light detected from the series of Scheimpflug images.

16. The ophthalmic imaging apparatus of claim 12, wherein
   the second image analyzing unit is further configured to analyze the series of Scheimpflug images to detect an image of a site of interest of the subject's eye, and
   the identifier assigning unit is further configured to perform assignment of an identifier representing the site of interest to one or more of the series of time series images collected by the second image collecting unit based on a detection result of the image of the site of interest from the series of Scheimpflug images.

17. The ophthalmic imaging apparatus of claim 12, wherein the identifier assigning unit is further configured to assign the identifier to a partial region of a Scheimpflug image corresponding to the ocular tissue.

18. The ophthalmic imaging apparatus of claim 12, wherein the first image collecting unit includes a first photography system and a second photography system that are configured to perform photography of the subject's eye from mutually different directions for the scanning of the three dimensional region, wherein
   the first photography system is configured to collect a first Scheimpflug image group, and
   the second photography system is configured to collect a second Scheimpflug image group, and
   wherein the series of Scheimpflug images includes the first Scheimpflug image group and the second Scheimpflug image group.

19. The ophthalmic imaging apparatus of claim 18, wherein photography performed by the first photography system and photography performed by the second photography system are performed in synchronization with each other.

20. The ophthalmic imaging apparatus of claim 19, wherein the processor circuitry is further configured as an image selecting unit configured to perform selection of another series of Scheimpflug images corresponding to the scanning of the three dimensional region from the first Scheimpflug image group and the second Scheimpflug image group based on a correspondence between the first Scheimpflug image group and the second Scheimpflug image group, the correspondence being determined based on the synchronization between the photography performed by the first photography system and the photography performed by the second photography system,
   wherein the image assigning unit is further configured to perform assignment of the identifier to each of the another series of Scheimpflug images.

21. The ophthalmic imaging apparatus of claim 20, wherein the first image collecting unit further includes an illumination system configured to project the slit light onto the three dimensional region, wherein an optical axis of the first photography system and an optical axis of the second photography system are arranged in an oblique manner in mutually opposite directions relative to an optical axis of the illumination system, and the image selecting unit is further configured to perform the selection of the another series of Scheimpflug images by selecting a plurality of Scheimpflug images containing no corneal reflection artifact from the first Scheimpflug image group and the second Scheimpflug image group based on the correspondence between the first Scheimpflug image group and the second Scheimpflug image group.

22. The ophthalmic imaging apparatus of claim 1, wherein the first image collecting unit performs the scanning of the three dimensional region by performing translation of the slit light in a direction perpendicular to a longitudinal direction of the slit light.

23. The ophthalmic imaging apparatus of claim 22, wherein the longitudinal direction of the slit light is oriented to coincide with a body axis direction of a subject.

24. The ophthalmic imaging apparatus of claim 23, wherein a size of the slit light in the longitudinal direction is equal to or greater than a corneal diameter in the body axis direction, and a distance of the translation of the slit light performed by the first image collecting unit is equal to or greater than a corneal diameter in a direction perpendicular to the body axis direction.

25. The ophthalmic imaging apparatus of claim 12, wherein the first image collecting unit performs the scanning of the three dimensional region by performing translation of the slit light in a direction perpendicular to a longitudinal direction of the slit light.

26. The ophthalmic imaging apparatus of claim 25, wherein the longitudinal direction of the slit light is oriented to coincide with a body axis direction of a subject.

27. The ophthalmic imaging apparatus of claim 26, wherein a size of the slit light in the longitudinal direction is equal to or greater than a corneal diameter in the body axis direction, and a distance of the translation of the slit light performed by the first image collecting unit is equal to or greater than a corneal diameter in a direction perpendicular to the body axis direction.

28. An ophthalmic image processing apparatus comprising:

a receiver including a communication device or a media drive that receives a series of images acquired by performing scanning of a three dimensional region of a subject's eye with scan light and a series of time series images collected by performing repetitive photography of the subject's eye in parallel with the scanning of the three dimensional region;

processor circuitry configured as a first image analyzing unit configured to analyze the series of time series images to determine time series shifts of the scan light; and the processor circuitry further configured as an image interpolating unit configured to perform interpolation of the series of images based on the time series shifts of the scan light.

29. An ophthalmic image processing apparatus comprising:

a receiver including a communication device or a media drive that receives a series of images acquired by performing scanning of a three dimensional region of a subject's eye with scan light and a series of time series images collected by performing repetitive photography of the subject's eye in parallel with the scanning of the three dimensional region;

processor circuitry configured as a second image analyzing unit configured to analyze the series of time series images to detect a series of images of the scan light; and the processor circuitry further configured as an identifier assigning unit configured to perform assignment of an identifier to each of the series of images acquired by performing the scanning of the three dimensional region with the scan light based on the series of images of the scan light detected from the series of time series images, the identifier representing an ocular tissue onto which the scan light is being projected when a corresponding image is acquired.

* * * * *